United States Patent
Levitt et al.

(10) Patent No.: US 7,384,767 B2
(45) Date of Patent: Jun. 10, 2008

(54) NUCLEIC ACID ENCODING AN INTERLEUKIN-9 RECEPTOR VARIANT

(75) Inventors: Roy Clifford Levitt, Ambler, PA (US); Luigi Grasso, Philadelphia, PA (US); Nicholas C. Nicolaides, Boothwyn, PA (US); Kenneth J. Holroyd, Collegeville, PA (US)

(73) Assignee: Genaera Corporation, Plymouth Meeting, PA (US)

( * ) Notice: Subject to any disclaimer, the term of this patent is extended or adjusted under 35 U.S.C. 154(b) by 0 days.

(21) Appl. No.: 11/700,260

(22) Filed: Jan. 31, 2007

(65) Prior Publication Data

US 2007/0190609 A1    Aug. 16, 2007

Related U.S. Application Data

(62) Division of application No. 11/371,157, filed on Mar. 9, 2006, now Pat. No. 7,208,292, which is a division of application No. 10/320,646, filed on Dec. 17, 2002, now Pat. No. 7,056,698, which is a division of application No. 09/596,377, filed on Jun. 16, 2000, now Pat. No. 6,602,850, which is a division of application No. 08/980,872, filed on Dec. 1, 1997, now abandoned.

(60) Provisional application No. 60/032,224, filed on Dec. 2, 1996.

(51) Int. Cl.
*C12N 5/10* (2006.01)
*C12N 15/12* (2006.01)
*C12N 15/63* (2006.01)

(52) U.S. Cl. ............. 435/69.1; 435/325; 435/320.1; 435/71.1; 536/23.5

(58) Field of Classification Search ............ None
See application file for complete search history.

(56) References Cited

U.S. PATENT DOCUMENTS

| | | | |
|---|---|---|---|
| 4,761,375 A | 8/1988 | Clark | 435/365.1 |
| 5,116,951 A | 5/1992 | Druez et al. | 530/395 |
| 5,132,109 A | 7/1992 | Dugas et al. | 424/85.2 |
| 5,157,112 A | 10/1992 | van Snick et al. | 530/387.9 |
| 5,164,317 A | 11/1992 | Hültner et al. | 435/386 |
| 5,180,678 A | 1/1993 | Druez et al. | 436/510 |
| 5,208,218 A | 5/1993 | van Snick et al. | 514/8 |
| 5,246,701 A | 9/1993 | Dugas et al. | 424/158.1 |
| 5,414,071 A | 5/1995 | Yang et al. | 530/351 |

FOREIGN PATENT DOCUMENTS

| | | |
|---|---|---|
| EP | A2-0361284 | 4/1990 |
| WO | WO 90/14432 | 11/1990 |
| WO | WO 91/10738 | 7/1991 |
| WO | WO 91/14767 | 10/1991 |
| WO | WO 92/05698 | 4/1992 |
| WO | WO 16/18049 | 9/1993 |

OTHER PUBLICATIONS

Aggarwal et al. (1996) Human Cytokines: Handbook for Basic and Clinical Research, Blackwell Scientific Publications, pp. 1-18.
Baker et al. (1996) Allergy and Immunology, J. Am. Med. Assoc. 275:1794-1795.
Borish et al. (1996) Continuing Medical Education: Update on Cytokines, J. Allergy Clin. Immunol. 97:719-734.
Borish et al. (1994) Polymorphisms in the Chromosome 5 Gene Cluster, J. Allergy Clin. Immunol. 93:345.
Busse et al. (1995) Mechanisms of Persistent Airway Inflammation in Asthma, Am. J. Respir. Crit. Care Med. 152:388-393.
Collete et al. (1996) Specific Th1 Cytokine Down-Regulation Associated with Primary Clinically Derived Human Immunodeficiency Virus Type 1 *Nef* Gene-Induced Expression, J. Immunol. 156:360-370.
De Vita et al. (1995) Local Cytokine Expression in the Progression Toward B Cell Malignancy in Sjögren's Syndrome, J. Rheumatol. 22:1674-1680.
Di Santo et al. (1995) Common Cytokine Receptor γ chain (γc)-Dependent Cytokines: Understanding in vivo Functions by Gene Targeting, Immunological Review 148:19-34.
Doull et al. (1996) Allelic Association of Gene Markers on Chromosomes 5q and 11q with Atopy and Bronchial Hyperresponsiveness, Am. J. Respir. Crit. Care Med. 153:1280-1284.
Fairman et al. (1995) Physical Mapping of the Minimal Region of Loss in 5q-chromosome, Proc. Natl. Acad. Sci. USA 92:7406-7410.
Finbloom et al. (1995) Induction of Early Response Genes by Interferons, Interleukins, and Growth Factors by the Tyrosine Phosphorylation of Latent Transcription Factors, Arthritis Rheum. 38:877-889.
Finnerty et al. (1996) Effects of Theophylline on Inflammatory Cells and Cytokines in Asthmatic Subjects: A Placebo-Controlled Parallel Group Study, Eur. Respir. J. 9:1672-1677.

(Continued)

*Primary Examiner*—Prema Mertz
(74) *Attorney, Agent, or Firm*—Morgan, Lewis & Bockius LLP

(57) ABSTRACT

This invention relates to the diagnosis, treatment and methods for discovery of new therapeutics for atopic asthma and related disorders based on variants of Asthma Associated Factor 2. One embodiment of the invention is a variant of AAF2 wherein codon 173 is deleted resulting in the loss of glutamine 173 from the mature protein precursor. This single amino acid deletion results in a non-functional AAF2 protein and therefore the presence of this phenotype should be associated with less evidence of atopic asthma. Correspondingly, the lack of susceptibility to an asthmatic, atopic phenotype is characterized by the loss of glutamine at codon 171 The invention includes isolated DNA molecules which are variants of the wild type sequence as well as the proteins encoded by such DNA and the use of such DNA molecules and expressed protein in the diagnosis and treatment of atopic asthma.

18 Claims, 24 Drawing Sheets

OTHER PUBLICATIONS

Fishman et al. (1996) Molecular Biology of Cytokines in Allergic Diseases and Asthma, Immunol. Allergy Clin. North Am. 16:613-642.

Gotoh et al. (1996) Steel Factor Induces Serine Phosphorylation of Stat3 in Human Growth Factor-Dependent Myeloid Cell Lines, Blood 88:138-145.

Grove et al. (1995) Bronchodilator Subsensitivity to Salbutamol After Twice Daily Salmeterol in Athmatic Patients, Lancent North Am. Ed. 346:201-206.

Gruss et al. (1996) Human Fibroblasts Express Functional IL-Receptors Formed by the IL-2R α- and β-Chain Subunits, J. Immunol. 157:851-857.

Hill et al. (1996) Nitric Oxide Production by the Rat Insulinoma Cell Line, RINm5F Is Specific for IL-1: A Spectrophotometric IL-1 Bioassay, Anal. Biochem. 236:14-19.

Holgate et al. (1995) Genetic and Environmental Influences on Airway Inflammation in Asthma, Int. Arch. Allergy Immunol. 107:29-33.

Horrigan et al. (1996) Polymerase Chain Reaction-Based Diagnosis of Del(5q) in Acute Myeloid Leukemia and Myelodyspistic Syndrome Identifies a Minimal Deletion Interval, Blood 88:2665-2670.

Kang et al. (1995) Activation of junB and c-myc Primary Response Genes by Interleukin 9 in a Human Factor-Dependent Cell Line, J. Cell. Physiol. 163:623-630.

Kermouni et al. (1995) The IL-9 receptor Gene (IL9R): Genomic Structure, Chromosomal Localization in the Pseudoautosomal Region of the Long Arm of the Sex Chromosomes, and Identification of IL9R Pseudogenes at 9qter, 10pter, 16pter, and 18pter, Genomics 29:371-382.

Klimka (1996) A Deletion Mutant of *Pseudomonas* Exotoxin-A Fused to Recombinant Human Interleukin-9 (rhIL-9-ETA) Shows Specific Cytotoxicity Against IL-9-Receptor-Expressing Cell Lines, Cytokines Mol. Ther. 2:139-146.

Krishna et al. (1996) Molecular Mediators of Asthma: Current Insights, Hosp. Pract. 31:115-130.

Lemoli et al. (1995) Interleukin-11 (IL-11) and IL-9 Counteract the Inhibitory Activity of Transforming Growth Factor β3 (TGF-β3) on Human Primitive Hematopoietic Progenitor Cells, Haematologica 80:5-12.

Levitt et al. (1988) Expression of airway hyperactivity to acetylcholine as a simple autosomal recessive trait in mice, FASEB 2:2605-2608.

Levitt et al. (1994) A Locas Regulating Bronchial Hyperresponsiveness Maps to Chromosome 5q., Am. J. Hum. Genet. 55:1120.

Liles et al. (1995) Review: Nomenclature and Biologic Significance of Cytokines Involved in Inflammation and the Host Immune Response, J. Infect. Dis. 172:1573-1580.

Lopez-Valpuesta et al. (1995) Cytokines and Thermoregulation: Interleukin-9 Injected in Preoptic Area Fails to Evoke Fever in Rats, Brain Res. Bull. 36:181-184.

Macchi et al. (1995) Mutations of Jak-3 Gene in Patients with Autosomal Severe Combined Immune Deficiency (SCID), Nature 337:65-68.

Meyers et al. (1994) Evidence for a Locus Regulating Total Serum IgE Levels Mapping to Chromosome 5, Genomics 23:464-470.

Mossman et al. (1995) Advances in Molecular Genetics, Transgenic Models, and Gene Therapy for the Study of Pulmonary Diseases, Am. J. Respir. Crit. Care Med. 151:2065-2069.

Murahashi et al. (1995) Roles of Stem Cell Factor in the In Vitro Growth of Blast Clonogenic Cells from Patients with Acute Myeloblastic Leukemia, J. Interferon Cytokine Res. 15:829-835.

Postma et al. (1995) Genetic Susceptibility to Asthma-Bronchial Hyperresponsiveness Coinherited with a Major Gene for Atopy, N. Engl. J. Med. 333:894-900.

Reinecker et al. (1995) Human Intestinal Epithelial Cells Express Functional Cytokine Receptors Sharing the Common γc Chain of the Interleukin 2 Receptor, Proc. Natl. Acad. Sci. USA 92:8353-8357.

Remick (1995) Cytokines: A Primer for Platic Surgeons, Ann. Plast. Surg. 35:549-559.

Renauld (1995) Interleukin-9: Structural Characteristics and Biologic Properties, Cytokines: Interleukins and Their Receptors, 80:287-303.

Renauld et al. (1995) Interleukin-9 and its Receptor: Involvement In Mast Cell Differentiation and T cell Oncogenesis, J. Leukoc. Biol. 57:353-360.

Renauld et al. (1990) Expression in Activated $CD4^+T$ cells, Genomic Organization, and Comparison with Mouse Gene, J. Immunol. 144:4235-4241.

Renauld et al. (1992) Expression Cloning of the Murine and Human Interleukin-9 Receptor cDNAs, Proc. Natl. Acad. Sci. USA 89:5690-5694.

Rosenwasser et al. (1995) Transcriptional Regulation of the Human IL-4 Gene in Atopy and Asthma, J. Invest. Med. 43:326.

Rosenwasser et al. (1994) Transcriptional Regulation of Human IL-4, J. Allergy Clin. Immunol. 93:599.

Rusten et al. (1996) The RAR-RXR as Well as the RXR-RXR Pathway is Involved in Signaling Growth Inhibition of Human CD34+Erythroid Progenitor Cells, Blood 87:1728-1736.

Schumann et al. (1996) Transcript Synthesis and Surface Expression of the Interleukin-2 Reception (α-, β-, and γ- chain) by Normal and Malignant Myeloid Cells, Blood 87:2419-2427.

Sun et al. (1995) Role of IRS-2 in Insulin and Cytokine Signalling, Nature 377:173-177.

Vermeesche et al. (1995) The IL-9 Receptor Gene is Located in the Pseudoautosomal Region of the Long Arm of the Sex Chromosomes, Is Expressed from the X and Y Chromosome and it Murine Homologue is Located on an Autosome, Chromosome Res. 3:105.

Wolf et al. (1996) Activation of CD4+T Lymphocytes from Interleukin 2-Deficient Mice by Costimulatory b7 Molecules, Proc. Natl. Acad. Sci. USA 93:2903-2908.

Yamaoka et al. (1995) Expression of Cytokine mRNA in Gastric Mucosa with *Helicobacter pylori* Infection, Scand. J. Gastroenterol. 30:1153-1159.

Yanagida et al. (1995) Effects of T-Helper 2-Type Cytokines, Interleukin-3 (IL-3), IL-4, IL-5, and IL-6 on the Survival of Cultured Human Mast Cells, Blood 86:3705-3714.

Yin et al. (1994) JAK1 Kinase Form Complexes with Interleukin-4 Receptor and 4PS/Insulin Receptor Substrate-1-like Protein and Is Activated by Interleukin-4 and Interleukin-9 in T Lymphocytes, J. Biol. Chem. 269:26614-26617.

Yin et al. (1995) Interleukin-9 Induces Tyrosine Phosphorylation of Insulin Receptor Substrate-1 via JAK Tyrosine Kinases, J. of Biol. Chem. 270:20497-20502.

Yin et al. (1995) Tyrosine Phosphorylation and Activation of JAK Family Tyrosine Kinases by Interleukin-9 in MO7E Cells, Blood 85:3101-3106.

Zhou et al. (1995) A Distinct Pattern of Cytokine Gene Expression by Human $CD83^+$ Blood Dendritic Cells, Blood 86:3295-3301.

Zhu et al. (1996) Multiple Transcription Factors Are Required for Activation of Human Interleukin-9 Gene in T Cells, J. Biol. Chem. 271:15815-15822.

Zhu et al. (1995) Identification of Critical Regulatory Regions in Human Interleukin-9 Gene Promoter, Blood 86: 2150.

Zola et al. (1996) Reduced Expression of the Interleukin-2-Receptor γ Chain on Cord Blood Lymphocytes: Relationship to Functional Immaturity of the Neonatal Immune Response, Immunology 87:86-91.

SEQUENCE RANGE: 243 TO 1944

```
         250         260         270         280         290         300         310         320         330         340         350         360         370         380
          *           *           *           *           *           *           *           *           *           *           *           *           *           *
ATGGGCAC CTGGCTCCTG GCTGCATCT GCATCTGCAC CTGTGCTGC TTGTCACAGG GGAAGGACAA GGGCCAAGGT CTAGAACCTT CACCTGCCTC ACCAACAACA TTCTCAGGAT CGATTGCCAC
 M  G  T  W  L  L   A  C  I   C  I  C  T   C  V  C   L  G  V   S  V  T  G   E  G  Q   G  P  R   S  R  T  F   T  C  L   T  N  N   I  L  R  I   D  C  H >

390         400         410         420         430         440         450         460         470         480         490         500         510         520
          *           *           *           *           *           *           *           *           *           *           *           *           *           *
TGGTCTGCCC CAGAGCTGGG ACAGGGCTCC AGCCCCTGGC TCCTCTTCAC CAGGAACCTC AGCAACCAGG GCTCCCTGGCG GCACACATAA GCACAGCAGT GTGCATCCTG CGTGGGCAGT CCTGAGGCAG TGTCCGTGCC
 W  S  A  P  E  L  G   Q  G  S   S  P  W   L  L  F  T   S  N  Q   A  P  G   G  T  H  K   C  I  L   R  G  S   E  C  T  V   V  L  P   P  E  A   V  L  V  P >

530         540         550         560         570         580         590         600         610         620         630         640         650         660
          *           *           *           *           *           *           *           *           *           *           *           *           *           *
ATCCTGACAAT TTCCACCACA CTTTCACACA CTGCATGTCT GGGAGGGAGC AGTCCAGGAG CCCGAGACAA CGTTAAGCTG GACCCGCCCT CTGACTTGCA GAGCAACATC AGTTCTGGCC
 S  D  N   F  T  I  T   F  H  H   C  M  S   G  R  E   Q  V  S  L   V  D  P   P  R  Y  L   P  R  R  H   V  K  L   D  P  P   S  D  L  Q   S  N  I   S  S  G >

670         680         690         700         710         720         730         740         750         760         770         780         790         800
          *           *           *           *           *           *           *           *           *           *           *           *           *           *
ACTGCATCCT GACTGGGAGC ATCAGTCCTG CCCTGGAGCC AATGACCACA CTTCTCAGCT CATGAGCTGG CTTCAAGAAG CAGGAAGAAG CCTGGGAGCA GGCCCAGGAG AGGGATCACA TTGTCGGGGT GACTTGGCTT
 H  C  I  L   T  W  S   I  S  P   A  L  E  P   M  T  T   L  L  S   Y  E  L  A   F  K  K   Q  E  E   A  W  E  Q   A  Q  H   I  V  G  V   T  W  L >

810         820         830         840         850         860         870         880         890         900         910         920         930         940
          *           *           *           *           *           *           *           *           *           *           *           *           *           *
ATACTTGAAG CCCTTGAGCT GGACCCTGGC TTTATCCATG AGGCCAGGT GGGTCCCAG ATGGCCACAC TGGAGGATGA TGTGGTAGAG GTGGAGTGAG ATACAGGCCA TGGAGAGCCT TGTGTGCTT
 I  L  E   A  F  E  L   D  P  G   F  I  H   E  A  R  L   R  V  Q   M  A  T   L  E  D  D   V  V  E   E  R  Y  T  G  Q   W  S  E  W   S  Q   P  V  C  P >

950         960         970         980         990        1000        1010        1020        1030        1040        1050        1060        1070        1080
          *           *           *           *           *           *           *           *           *           *           *           *           *           *
CCAGGCTCCC CAGAGACAAG GCCCCTTGGA CCCACCCTGG GGTGGCCAG GAAACACCCT TGTGCTGTG TCCATCTTTC TCCTGCTGAC TGGCCCCTGT TACTTCCTGT TCAAGCTGTC GCCCAGGGTG AAGAGAATCT
 Q  A  P   Q  R  Q   G  P  L  I   P  P  W   G  W  P   G  N  T  L   V  A  V   S  I  F   L  L  L  T   G  P  T   Y  L  L   F  K  L  S   P  R  V   K  R  D >
```

FIG. 2-1

```
          1090       1100       1110       1120       1130       1140       1150       1160       1170       1180       1190       1200       1210       1220
            *          *          *          *          *          *          *          *          *          *          *          *          *          *
       TCTACCAGAAT CGTGCCCTCT CCAGGGATGT TCTTCCAGCC CCTCTACAGT GTACACAATG GAACTTCCA GACTTGGATG GGGCCCACA GGGCCGGTGT GCTCGTTGAC CAGGACTGTG CTGGCACCCC ACAGGGAGCC
        F  Y  Q  N   V  P  S   P  A  M   F  F  Q  P   L  Y  S   V  H  N   G  N  F  Q   T  W  M   G  A  H   R  A  G  V   L  L  S    Q  D  C    A  G  T  P    Q  G  A>
           1230       1240       1250       1260       1270       1280       1290       1300       1310       1320       1330       1340       1350       1360
            *          *          *          *          *          *          *          *          *          *          *          *          *          *
       TTGGAGCCCT GGGTCCAGGA GGCCACTGCA CTGCTCACTT GTGGCCCAGC GGCGTCCTTGG AAATCTGTGG CCCTGGAGGA GGAACAGGAG GGCCCTGGGA CCAGGCTCCC GGGAACCTG AGCTCAGAGG ATGTGCTGCC
        L  E  P   C  V  Q  E   A  T  A   L  L  T  C   G  P  A   R  P  W    K  S  V    A  L  E  E   E  Q  E   G  P  G   T  R  L  P   G  N  L   S  S  E   D  V  L  P>
           1370       1380       1390       1400       1410       1420       1430       1440       1450       1460       1470       1480       1490       1500
            *          *          *          *          *          *          *          *          *          *          *          *          *          *
       AGCAGGGTGT ACGGAGTGGA GGGTACAGAG GCTTGCCTAT CTGCCACAGG AGGACTGGGC CCCCAGTCC CTGACTAGGC AGACTCAGAG CCCCCAGCCT GGCAGCAGGA GCAGCACAG AGCAACAACA
        A  G  C   T  E  W    R  V  Q  T   L  A  Y  L   P  Q    E  D  W  A  P  T  S   L  T  R   P  A  P  P   D  S  E   G  S  R    S  S  S  S    S  N  N>
           1510       1520       1530       1540       1550       1560       1570       1580       1590       1600       1610       1620       1630       1640
            *          *          *          *          *          *          *          *          *          *          *          *          *          *
       ACACTACTG TGCCTGGGGC TGCTATGGGG GATGGCACCT CTCAGCCCTC CCAGGAAAACA CACAGAGCTC CCAGGAGCTC CCTGTGCCT TTCTTGTGAC CCTGTGCCT CAGCAGGCC TGGAGACCTA GCAAGGAGTT
         N  Y  C   A  L  G   C  Y  G    G  W  H  L   S  A  L   P  G  N   T  Q  S  S    G  P  I    P  A  L    A  C  G  L   S  C  D   H  Q  G   L  E  T  Q    Q  G  V>
           1650       1660       1670       1680       1690       1700       1710       1720       1730       1740       1750       1760       1770       1780
            *          *          *          *          *          *          *          *          *          *          *          *          *          *
       GCCTGGGTGC TGGCTGGTCA CTGCCAGAGG CCTGGGCTGC ATGAGGACCT CCAGGGGCAG TGCTCCCTT CTGGTCCTCG CAAGGGCTTC TCCTGGACAT TCTAGGTCC TGACTCCCA GATGCATCAT GTCCATTTTG
        A  W  V   L  A  G  H   C  Q  R   P  G  L    H  E  D  L   Q  G  M    L  L  P    S  V  L  S   K  A  R   S  W  T   F  *   V  P   D  S  P   D  A  S   C  P  F  W>
           1790       1800       1810       1820       1830       1840       1850       1860       1870       1880       1890       1900       1910       1920
            *          *          *          *          *          *          *          *          *          *          *          *          *          *
       GGAAAATGGA CTGAAGTTTC TGGAGCCCCT GTCTGAGACT GAACCTCCTG AGAGGGGGCC CCTAGCAGCG GTCAGAGGTC CCTGTCCAGCC GGAGGCTGGA GGAGGGAGCC TCAACCCCTC TGCTCAGTGC CTGTGGGAG
         E  N  G   L  K  F   L  E  P   L  S  E  T   E  P  P    E  P  P   E  K  G  P   L  A  A    V  R  G    P  V  W  M   E  A  G   G  S  P   L  N  P  S   A  Q  C   L  W  G>
           1930       1940
            *          *
       CAGCCCCTAC CCTTCAGCATC CTGG
        A  A  S   T  L  S  I   L>
```

SEQUENCE RANGE: 243 TO 1103

```
        250        260        270        280        290        300        310        320        330        340        350        360        370        380
         *          *          *          *          *          *          *          *          *          *          *          *          *          *
ATGGGCAC CTGGCTCCTG GCCTGCATCT GCATCTGCAC CGATCTGCAC CTGTGTCTGC TTGGGAGTCT CTGTCGTCAG SVTGGAGACAA GGGCCAAGGT CTAGAACCTT CACCTGCCTC ACCAACAACA TTCTCAGGAT CGATTGCCAC
 M  G  T   W  L  L   A  C  I   C  I  C  T   D  L  H   L  C  V  C   L  G  V   S  V  T  G   E  G  Q   G  P  R  S   R  T  F   T  C  L   T  N  N   I  L  R  I   D  C  H >
        390        400        410        420        430        440        450        460        470        480        490        500        510        520

530        540        550        560        570        580        590        600        610        620        630        640        650        660
         *          *          *          *          *          *          *          *          *          *          *          *          *          *
TGTCTCTGCC CAGAGCTGGG ACAGGGCTCC AGCCCCTGGC TCCTCTTCAC CAGCAACCAG GCTCCCTGGCG GCACACATAA GCACATCCTG CGGGGCAGTG AGTGCACCGT CGTGCTGCCA CCTGAGGCAG TGCTCGTGCC
 W  S  A   P  E  L  G   Q  G  S   S  P  W   L  L  F  T   S  N  Q   A  P  G   G  T  H  K   C  I  L   R  G  S   E  C  T  V   V  L  P   P  E  A   V  L  V  P >
        670        680        690        700        710        720        730        740        750        760        770        780        790        800

810        820        830        840        850        860        870        880        890        900        910        920        930        940
         *          *          *          *          *          *          *          *          *          *          *          *          *          *
ATCTGACAAT TTCACCATCA CTTTCCACCA CTGCATGAGC GGGAGGGAGC AGGTCAGCCT GGTGGACCCT GAGTACCTGC CCCGGAGACA CGTTAAGCTG GACCCGCCCC CTGACTTGCA GAGCAACATC AGTTCGGGCC
 S  D  N   F  T  I   T  F  H  H   C  M  S   G  R  E  Q   Q  V  S  L   V  D  P   E  Y  L   P  R  R  H   V  K  L   D  P  P   P  S  D  L   Q  S  N  I   S  S  G >
        950        960        970        980        990       1000       1010       1020       1030       1040       1050       1060       1070       1080

ACTGAGAAG GACCTGGAAG ATCAGTCCTG CCTTGAGCAC AATGACCACA CTTCCAGCT ATGAGCTAGC CTTCAAGAAG CAGGAAGAAG CCTGGGAGCA GGCCCAGCAC AGGGATCACA TTGTCGGGGT GACCTGGCTT
 H  C  I  L   T  W  S   I  S  P   A  L  E  P   M  T  T   L  L  S   Y  E  L  A   F  K  K   Q  E  E   A  W  E  Q   A  Q  H   R  D  H   I  V  G  V   T  W  L >
                                                                    870         880         890         900         910         920         930         940

ATACTTCAAG CCCTTGTGAC GGACCCTGAT GGACCCCTGGC TTTATCCATG AGGCCAGGCT CGTTGTCCAG GGGTGCCACAC TGGAGGATGA TGTGGTAGAG GAGGAGCGTT ATACAGGCCA TGGAGCCAAG GTGGAGTTGG SCCAGAGAGAAG GACCTCCTGT TGGACCTGCTT
 I  L  E   A  F  E  L   D  P  G   F  I  H   E  A  R  L   R  V  Q   M  A  T   L  E  D  D   V  V  E   E  E  R   Y  T  G  Q   W  S  E   W  S  Q   P  V  C  F >
        950         960         970         980         990        1000        1010        1020        1030        1040        1050        1060        1070        1080

CCAGGCTCCC CAGAGACAAG GCCCCCCTGG CCCACCCTGG GGGTGGGCCAG GCAACACCCT GTGTTGCTGTG TCCATCTTTC TCCTGCTGAC TGGCCCGACC TACCTCCTGT TCAAGCTTTCA GCCCAGACTTC GGATGGGGGC
                     Q  A  P   P  Q  R  Q   G  P  L  I   P  P  W   G  W  P   G  N  T  L   V  A  V   S  I  F   L  L  L  T   G  P  T   Y  L  L   F  K  L  S   P  R  L   G  W  G >
                                 1090        1100

CCACAGGCGC GGTGTGCTGT TGA
                                  P  T  G  P   P  V  C  C   * >
```

FIG. 4

SEQUENCE RANGE: 243 TO 1944

```
          250        260        270        280        290        300        310        320        330        340        350        360        370        380
           *          *          *          *          *          *          *          *          *          *          *          *          *          *
ATGGGCAC CTGGCTCCTG GCCTGCATCT GCATCTGCAC CTTGTCTCTGC TTGGAGTCT CTGTCACAGG GGAAGGACAA GGGCCAAGGT CTAGAACCTT CACCTGCCTC ACCAACACA TTCTCAGGAT CGATTGCCAC
 M  G  T   W  L  L    A  C  I    C  I  C  T   C  V  C    L  G  V  S    V  T  G  E    G  Q  G  P    R  S  R  T    F  T  C  L    T  N  N  I    L  R  I  D   C  H >
          390        400        410        420        430        440        450        460        470        480        490        500        510        520
           *          *          *          *          *          *          *          *          *          *          *          *          *          *
TGGTCTGCCC CAGAGCTGGG ACAGGGCTCC AGCCCCTGGC TCCTCTTCAC CAGCAACCAG GCTCCCTGGG GCACACATAA GTGCATCTTG CGGGGCAGTG AGTGCACCGT CCTGCTGCCA CCTGAGGCAG TGCTCGTGCC
 W  S  A   P  E  L  G   Q  G  S    S  P  W    L  L  F  T    S  N  Q    A  P  G  G    T  H  K  C    I  L  R  G    S  E  C  T    V  L  L  P    P  E  A  V   L  V  P >
          530        540        550        560        570        580        590        600        610        620        630        640        650        660
           *          *          *          *          *          *          *          *          *          *          *          *          *          *
ATCTGACAAT TTCACCATCA CTTTCCACCA CTGCATGTCT GGAGGGAGC CTGGATGTCAGCCT GGGAGGGAGC AGGTCAGGCT GGTGACCTG GACTGCCCG GAGTGACCTG CGTTAAGCTG GACCCCGCCT GACTTGCA GACCAACATC AGTTCTGGCC
 S  D  N   F  T  I    T  F  H  H   C  M  S    G  R  E  Q    V  S  L  V    D  P  E  Y    L  P  R  R    H  V  K  L    D  P  P  S    D  L  Q  S    N  I  S   S  G >
          670        680        690        700        710        720        730        740        750        760        770        780        790        800
           *          *          *          *          *          *          *          *          *          *          *          *          *          *
ACTGCATCCT GACCTGGAGC ATCAGTCCTG CCTTGGAGCC AATGACCACA CTTCTCAGCT ATGAGCTGGC CTTCAAGAAG CAGGAGGAGG CCTGGGAGGC GATCACATTG TCGGGGTGAC CTGGCTTATA
 H  C  I  L   T  W  S    I  S  P   A  L  E  P    M  T  T    L  L  S  Y    E  L  A  F    K  K  Q  E    E  A  W  E    A  Q  H  R    D  H  I  L    V  G  V  T   W  L  I >
          810        820        830        840        850        860        870        880        890        900        910        920        930        940
           *          *          *          *          *          *          *          *          *          *          *          *          *          *
CTTGAAGCCT TTGAATTTGA CCCCTGGCTTT ATCCATGAGG CCAGGCTGCG CGTCCAGATG GCCACACTGG AGGATGATGT GGTAGAGGAG GAGGGTTATA CAGGCCAGTG AGCCCAGCCTG TGTGTGCCA
 L  E  A   F  E  L  D   P  G  F   I  H  E   A  R  L  R    V  Q  M  A    T  L  E  D    D  V  E  E    E  R  Y  T    G  Q  W  S    E  W  S  Q   P  V  C  F  Q >
          950        960        970        980        990       1000       1010       1020       1030       1040       1050       1060       1070       1080
           *          *          *          *          *          *          *          *          *          *          *          *          *          *
GGCTCCCCAG AGACAAGGCC CTCTGATCCC ACCCTGGGGG TGGCCAGGCA ACACCCTTGT TGCTGTGTCC ATCTTTCTCC TGCTGCTGCC CCCGACTAC AGCTGTGCC CAGGGTGAAG AGAATCTTCT
 A  P  Q   R  Q  G    P  L  I  P   P  W  G   W  P  G   N  T  L  V    A  V  S  I    F  L  L  L    T  G  P  T    Y  L  L  F    K  L  S  P    R  V  K  R   I  F >
```

```
210         220         230         240         250         260         270         280         290         300         310         320         330
GCT GGACCCTTGGA GAGTGAGGCC CTGAGGCGAG ACATGGGCAC CTGAGGTCCTG GCCTGCATCT GCATTGCAC CTGTGTCTGC TTGGGAGTCT CTGTCACAGG GGAAGGACAA GGGCCAAGGT
                                        M   G   T   W   L   L   A   C   I   C   I   C   T   C   V   C   L   G   V   S   V   T   G   E   G   Q   G   P   R>
    340         350         360         370         380         390         400         410         420         430         440         450         460
CTAGAACCTT CACCTGCCTC ACCAACAACA TTCTCAGGAT CGATTGCCAC TGGTCTGCCC CAGAGCTGGG ACAGGGCTCC AGCCCCTGGC TCCTCTTCAC CAGCAACCAG GCTCCTGGCG GCACACATAA
 S   R   T   F   T   C   L   T   N   N   I   L   R   I   D   C   H   W   S   A   P   E   L   G   Q   G   S   P   W   L   L   F   T   S   N   Q   A   P   G   G   T   H   K>
    470         480         490         500         510         520         530         540         550         560         570         580         590
GTGCATCTTG CGGGGCAGTG AGTGCACCGT CGTGCTGCCA CCCTGAGGCC GTGCTCGTGCC CCTGAGGCAG TGCTCGTGCC ATCTGACAAT TTCACCATCA CTTTCCACCA CTGCATGTCT GGGAGGGAGC AGTCAGCCCT GGTGGACCCG
 C   I   L   R   G   S   E   C   T   V   V   L   P   P   E   A   V   L   V   P   S   D   N   F   T   I   T   F   H   H   C   M   S   G   R   E   Q   V   S   L   V   D   P>
    600         610         620         630         640         650         660         670         680         690         700         710         720
GAGTACCTGC CCCGGAGACA CGCTGGACCC GCCCTTCTGA CCCAGAGCA TTGCAGAGCA ACATCAGTTC GGCCACTGC ATCCTGACCT GGAGCATCAG TCCTGCCTTG GAGCCAATGA CCACACTTCT CAGCTATGAG
 E   Y   L   P   R   R   H   A   G   P   A   L>
```

FIG. 6

```
210        220        230        240        250        260        270        280        290        300        310        320        330
GCT GGACCTTGGA GAGTGAGGCC CTGAGGCCAG ACATGGGCAC CTGGCTCCTG GCCTGCATCT GCACTTGCAC CTGTGTCTGC TTGGAGTCT CTGTCACAGG GGAAGGACAA GGGCCAAGGT
                                     M  G  T  W  L  L  A  C  I  C  T  C  V  C  L  G  V  S  V  T  G  E  G  Q  G  P  R>
       340        350        360        370        380        390        400        410        420        430        440        450        460
CTAGAACCTT CACCTGCCTC ACCAACAACA TTCTCAGGAT CGATTGCCAC TGGTCTGCC CAGAGCTGGG ACAGGGCTCC AGCCCCTTGG TCCTCTTCAC CAGCAACCAG GCTCCTGGCG GCACACATAA
 S  R  T  F  T  C  L  T  N  N  I  L  R  I  D  C  H  W  S  A  P  E  L  G  Q  G  S  P  W  L  L  F  T  S  N  Q  A  P  G  G  T  H  K>
       470        480        490        500        510        520        530        540        550        560        570        580        590
GTGCCATCTTG CGGGGCCAGTG AGTGCACCGT CGTGCTGCCA CCTGAGGCAG TGCTCGTGCC ATCTGACAAT TTCACCATCA CTTTCCACCA CTGCATGTCT GGGAGGGAGC AGTCAGCCT GGTGGACCCG
 C  I  L  R  G  S  E  C  T  V  V  L  P  P  E  A  V  L  V  P  S  D  N  F  T  I  T  F  H  H  C  M  S  G  R  E  Q  V  S  L  V  D  P>
       600        610        620        630        640        650        660        670        680        690        700        710        720
GAGTACCTGC CCCGAGACA CGAGCAACAT CAGTTCTGGC CACTTGCATCC TGACCTGGAG CATCAGTCCT GCCTTGGAGC CAATGACCAC ACTTCTCAGC TATGAGCTGG CCTTCAAGAA GCAGGAAGAG
 E  Y  L  P  R  R  H  E  Q  H  Q  F  W  P  L  H  P  D  L  E  H  Q  S  C  L  G  A  N  D  H  T  S  Q  L>
```

FIG. 7

SEQUENCE RANGE: 243 TO 437

```
        250       260       270       280       290       300
          *         *         *         *         *         *
ATGGGCAC CTGGCTCCTG GCCTGCATCT GCATCTGCAC CTGTGTCTGC TTGGGAGTCT
 M  G  T  W  L  L  A  C  I  C  I  C  T  C  V  C  L  G  V
        310       320       330       340       350       360
          *         *         *         *         *         *
CTGTCACAGG GGAAGGACAA GGGCCAAGGT CTAGAACCTT CACCTGCCTC ACCAACAACA
 S  V  T  G  E  G  Q  G  P  R  S  R  T  F  T  C  L  T  N  N
        370       380
          *         *
TTCTCAGGAT CGATTGCCAC
 I  L  R  I  D  C  H>
        390       400       410       420       430
          *         *         *         *         *
TGGTCTGCCC CAGAGCTGGG ACAGGGCTCC AGCCCCTGGC TCCTCTTCAC CAGTTAA
 W  S  A  P  E  L  G  Q  G  S  S  P  W  L  L  F  T  S  *>
```

FIG. 8

INTERLEUKIN-9 RECEPTOR VARIANTS

| | | GENOTYPE | |
|---|---|---|---|
| PHENOTYPE | ARG/ARG | ARG/HIS | HIS/HIS |
| ALLERGIC | 1/18 | 8/18* | 1/18* |
| NONALLERGIC | 7/18 | 1/18 | 0/18 |

FISHER EXACT TEST P=0.002**

\* INCLUDES ASTHMATICS
\*\* ASSUMES ALLERGY IS AUTOSOMAL DOMINANT TRAIT

FIG. 9

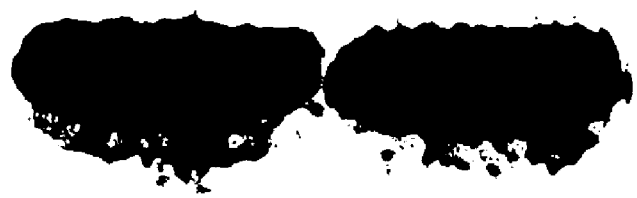
IL-9 RECEPTOR
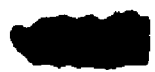
FIG. 11

INTRON 5 POLYMORPHISM OF THE HUMAN IL-9 RECEPTOR

```
         90         100        110        120        130       ↓140        150
AAGTGTGATG AGTGTGAAAG TGTTCCTGTA GACATGTTTG CCTGTGTGTG CACATGTGTA TTTGTGGGCA⟩    WT HUMAN IL-9 RECEPTOR SEQUENCE
|||||||||| |||||||||| |||||||||| |||||||||| |||||||||| |||||||||| ||||||||||
AAGTGTGATG AGTGTGAAAG TGTTCCTGTA GACATGTTTG CCTGTGTGTG CATATGTGTA TTTGTGGGCA 90         100        110        120        130       ↓140        150
AAGTGTGATG AGTGTGAAAG TGTTCCTGTA GACATGTTTG CCTGTGTGTG CACATGTGTA TTTGTGGGCA⟩    MUTANT IL-9 RECEPTOR SEQUENCE
|||||||||| |||||||||| |||||||||| |||||||||| ||| |||||| |||||||||| ||||||||||
AAGTGTGATG AGTGTGAAAG TGTTCCTGTA GACATGTTTG CCTGTGTGTG CATATGTGTA TTTGTGGGCA
```

FIG. 17

SEQUENCE LISTING (1) GENERAL INFORMATION:

(iii) NUMBER OF SEQUENCES: 36

(2) INFORMATION FOR SEQ ID NO: 1:

(i) SEQUENCE CHARACTERISTICS:
        (A) LENGTH: 1947 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 1:

```
AGCAGCTCTG TAATGCGCTT GTGGTTTCAG ATGTGGGCGG CCTGTGTGAA CCTGTCGTGC    60

AAAGCTCACG TCACCAACTG CTGCAGTTAT CTCCTGAATC AGGCTGAGGG TCTTTGCTGT   120

GCACCCAGAG ATAGTTGGGT GACAAATCAC CTCCAGGTTG GGGATGCCTC AGACTTGTGA   180

TGGGACTGGG CAGATGCATC TGGGAAGGCT GGACCTTGGA GAGTGAGGCC CTGAGGCGAG   240

ACATGGGCAC CTGGCTCCTG GCCTGCATCT GCATCTGCAC CTGTGTCTGC TTGGGAGTCT   300

CTGTCACAGG GGAAGGACAA GGGCCAAGGT CTAGAACCTT CACCTGCCTC ACCAACAACA   360

TTCTCAGGAT CGATTGCCAC TGGTCTGCCC CAGAGCTGGG ACAGGGCTCC AGCCCCTGGC   420

TCCTCTTCAC CAGCAACCAG GCTCCTGGCG GCACACATAA GTGCATCTTG CGGGGCAGTG   480

AGTGCACCGT CGTGCTGCCA CCTGAGGCAG TGCTCGTGCC ATCTGACAAT TTCACCATCA   540

CTTTCCACCA CTGCATGTCT GGGAGGGAGC AGGTCAGCCT GGTGGACCCG GAGTACCTGC   600

CCCGGAGACA CGTTAAGCTG GACCCGCCCT CTGACTTGCA GAGCAACATC AGTTCTGGCC   660

ACTGCATCCT GACCTGGAGC ATCAGTCCTG CCTTGGAGCC AATGACCACA CTTCTCAGCT   720

ATGAGCTGGC CTTCAAGAAG CAGGAAGAGG CCTGGGAGCA GGCCCAGCAC AGGGATCACA   780

TTGTCGGGGT GACCTGGCTT ATACTTGAAG CCTTTGAGCT GGACCCTGGC TTTATCCATG   840

AGGCCAGGCT GCGTGTCCAG ATGGCCACAC TGGAGGATGA TGTGGTAGAG GAGGAGCGTT   900

ATACAGGCCA GTGGAGTGAG TGGAGCCAGC CTGTGTGCTT CCAGGCTCCC CAGAGACAAG   960

GCCCTCTGAT CCCACCCTGG GGGTGGCCAG GCAACACCCT TGTTGCTGTG TCCATCTTTC  1020

TCCTGCTGAC TGGCCCGACC TACCTCCTGT TCAAGCTGTC GCCCAGGGTG AAGAGAATCT  1080

TCTACCAGAA CGTGCCCTCT CCAGCGATGT TCTTCCAGCC CCTCTACAGT GTACACAATG  1140

GGAACTTCCA GACTTGGATG GGGGCCCACA GGGCCGGTGT GCTGTTGAGC CAGGACTGTG  1200
```

```
CTGGCACCCC ACAGGGAGCC TTGGAGCCCT GCGTCCAGGA GGCCACTGCA CTGCTCACTT   1260

GTGGCCCAGC GCGTCCTTGG AAATCTGTGG CCCTGGAGGA GGAACAGGAG GGCCCTGGGA   1320

CCAGGCTCCC GGGGAACCTG AGCTCAGAGG ATGTGCTGCC AGCAGGGTGT ACGGAGTGGA   1380

GGGTACAGAC GCTTGCCTAT CTGCCACAGG AGGACTGGGC CCCCACGTCC CTGACTAGGC   1440

CGGCTCCCCC AGACTCAGAG GGCAGCAGGA GCAGCAGCAG CAGCAGCAGC AGCAGCAACA   1500

ACAACAACTA CTGTGCCTTG GGCTGCTATG GGGGATGGCA CCTCTCAGCC CTCCCAGGA    1560

ACACACAGAG CTCTGGGCCC ATCCCAGCCC TGGCCTGTGG CCTTTCTTGT GACCATCAGG   1620

GCCTGGAGAC CCAGCAAGGA GTTGCCTGGG TGCTGGCTGG TCACTGCCAG AGGCCTGGGC   1680

TGCATGAGGA CCTCCAGGGC ATGTTGCTCC CTTCTGTCCT CAGCAAGGCT CGGTCCTGGA   1740

CATTCTAGGT CCCTGACTCG CCAGATGCAT CATGTCCATT TTGGGAAAAT GGACTGAAGT   1800

TTCTGGAGCC CTTGTCTGAG ACTGAACCTC CTGAGAAGGG GCCCCTAGCA GCGGTCAGAG   1860

GTCCTGTCTG GATGGAGGCT GGAGGCTCCC CCCTCAACCC CTCTGCTCAG TGCCTGTGGG   1920

GAGCAGCCTC TACCCTCAGC ATCCTGG                                      1947

(2) INFORMATION FOR SEQ ID NO: 2:

(i) SEQUENCE CHARACTERISTICS:
        (A) LENGTH: 1947 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 2:

AGCAGCTCTG TAATGCGCTT GTGGTTTCAG ATGTGGGCGG CCTGTGTGAA CCTGTCGTGC     60

AAAGCTCACG TCACCAACTG CTGCAGTTAT CTCCTGAATC AGGCTGAGGG TCTTTGCTGT    120

GCACCCAGAG ATAGTTGGGT GACAAATCAC CTCCAGGTTG GGGATGCCTC AGACTTGTGA    180

TGGGACTGGG CAGATGCATC TGGGAAGGCT GGACCTTGGA GAGTGAGGCC CTGAGGCGAG    240

ACATGGGCAC CTGGCTCCTG GCCTGCATCT GCATCTGCAC CTGTGTCTGC TTGGGAGTCT    300

CTGTCACAGG GGAAGGACAA GGGCCAAGGT CTAGAACCTT CACCTGCCTC ACCAACAACA    360

TTCTCAGGAT CGATTGCCAC TGGTCTGCCC CAGAGCTGGG ACAGGGCTCC AGCCCCTGGC    420

TCCTCTTCAC CAGCAACCAG GCTCCTGGCG GCACACATAA GTGCATCTTG CGGGGCAGTG    480

AGTGCACCGT CGTGCTGCCA CCTGAGGCAG TGCTCGTGCC ATCTGACAAT TCACCATCA     540

CTTTCCACCA CTGCATGTCT GGGAGGGAGC AGGTCAGCCT GGTGGACCCG GAGTACCTGC    600

CCCGGAGACA CGTTAAGCTG GACCCGCCCT CTGACTTGCA GAGCAACATC AGTTCTGGCC    660

ACTGCATCCT GACCTGGAGC ATCAGTCCTG CCTTGGAGCC AATGACCACA CTTCTCAGCT    720

ATGAGCTGGC CTTCAAGAAG CAGGAAGAGG CCTGGGAGCA GGCCCAGCAC AGGGATCACA    780

TTGTCGGGGT GACCTGGCTT ATACTTGAAG CCTTTGAGCT GGACCCTGGC TTTATCCATG    840

AGGCCAGGCT GCGTGTCCAG ATGGCCACAC TGGAGGATGA TGTGGTAGAG GAGGAGCGTT    900

ATACAGGCCA GTGGAGTGAG TGGAGCCAGC CTGTGTGCTT CCAGGCTCCC AGAGACAAG    960

GCCCTCTGAT CCCACCCTGG GGGTGGCCAG GCAACACCCT TGTTGCTGTG TCCATCTTTC   1020

TCCTGCTGAC TGGCCCGACC TACCTCCTGT TCAAGCTGTC GCCCAGGGTG AAGAGAATCT   1080

TCTACCAGAA CGTGCCCTCT CCAGCGATGT TCTTCCAGCC CCTCTACAGT GTACACAATG   1140

GGAACTTCCA GACTTGGATG GGGGCCCACA GGGCCGGTGT GCTGTTGAGC CAGGACTGTG   1200
```

```
CTGGCACCCC ACAGGGAGCC TTGGAGCCCT GCGTCCAGGA GGCCACTGCA CTGCTCACTT    1260

GTGGCCCAGC GCATCCTTGG AAATCTGTGG CCCTGGAGGA GGAACAGGAG GGCCCTGGGA    1320

CCAGGCTCCC GGGGAACCTG AGCTCAGAGG ATGTGCTGCC AGCAGGGTGT ACGGAGTGGA    1380

GGGTACAGAC GCTTGCCTAT CTGCCACAGG AGGACTGGGC CCCCACGTCC CTGACTAGGC    1440

CGGCTCCCCC AGACTCAGAG GGCAGCAGGA GCAGCAGCAG CAGCAGCAGC AGCAGCAACA    1500

ACAACAACTA CTGTGCCTTG GGCTGCTATG GGGGATGGCA CCTCTCAGCC CTCCCAGGAA    1560

ACACACAGAG CTCTGGGCCC ATCCCAGCCC TGGCCTGTGG CCTTTCTTGT GACCATCAGG    1620

GCCTGGAGAC CCAGCAAGGA GTTGCCTGGG TGCTGGCTGG TCACTGCCAG AGGCCTGGGC    1680

TGCATGAGGA CCTCCAGGGC ATGTTGCTCC CTTCTGTCCT CAGCAAGGCT CGGTCCTGGA    1740

CATTCTAGGT CCCTGACTCG CCAGATGCAT CATGTCCATT TTGGGAAAAT GGACTGAAGT    1800

TTCTGGAGCC CTTGTCTGAG ACTGAACCTC CTGAGAAGGG GCCCCTAGCA GCGGTCAGAG    1860

GTCCTGTCTG GATGGAGGCT GGAGGCTCCC CCCTCAACCC CTCTGCTCAG TGCCTGTGGG    1920

GAGCAGCCTC TACCCTCAGC ATCCTGG                                        1947

(2) INFORMATION FOR SEQ ID NO: 3:

(i) SEQUENCE CHARACTERISTICS:
        (A) LENGTH: 1944 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 3:

AGCAGCTCTG TAATGCGCTT GTGGTTTCAG ATGTGGGCGG CCTGTGTGAA CCTGTCGTGC      60

AAAGCTCACG TCACCAACTG CTGCAGTTAT CTCCTGAATC AGGCTGAGGG TCTTTGCTGT     120

GCACCCAGAG ATAGTTGGGT GACAAATCAC CTCCAGGTTG GGGATGCCTC AGACTTGTGA     180

TGGGACTGGG CAGATGCATC TGGGAAGGCT GGACCTTGGA GAGTGAGGCC CTGAGGCGAG     240

ACATGGGCAC CTGGCTCCTG GCCTGCATCT GCATCTGCAC CTGTGTCTGC TTGGGAGTCT     300

CTGTCACAGG GGAAGGACAA GGGCCAAGGT CTAGAACCTT CACCTGCCTC ACCAACAACA     360

TTCTCAGGAT CGATTGCCAC TGGTCTGCCC CAGAGCTGGG ACAGGGCTCC AGCCCCTGGC     420

TCCTCTTCAC CAGCAACCAG GCTCCTGGCG GCACACATAA GTGCATCTTG CGGGGCAGTG     480

AGTGCACCGT CGTGCTGCCA CCTGAGGCAG TGCTCGTGCC ATCTGACAAT TCACCATCA     540

CTTTCCACCA CTGCATGTCT GGGAGGGAGC AGGTCAGCCT GGTGGACCCG GAGTACCTGC     600

CCCGGAGACA CGTTAAGCTG GACCCGCCCT CTGACTTGCA GAGCAACATC AGTTCTGGCC     660

ACTGCATCCT GACCTGGAGC ATCAGTCCTG CCTTGGAGCC AATGACCACA CTTCTCAGCT     720

ATGAGCTGGC CTTCAAGAAG CAGGAAGAGG CCTGGGAGGC CAGCACAGG GATCACATTG      780

TCGGGGTGAC CTGGCTTATA CTTGAAGCCT TGAGCTGGA CCCTGGCTTT ATCCATGAGG      840

CCAGGCTGCG TGTCCAGATG GCCACACTGG AGGATGATGT GGTAGAGGAG GAGCGTTATA     900

CAGGCCAGTG GAGTGAGTGG AGCCAGCCTG TGTGCTTCCA GGCTCCCCAG AGACAAGGCC     960

CTCTGATCCC ACCCTGGGGG TGGCCAGGCA ACACCCTTGT TGCTGTGTCC ATCTTTCTCC    1020

TGCTGACTGG CCCGACCTAC CTCCTGTTCA AGCTGTCGCC CAGGGTGAAG AGAATCTTCT    1080

ACCAGAACGT GCCCCTCTCA GCGATGTTCT TCCAGCCCCT CTACAGTGTA CACAATGGGA    1140

ACTTCCAGAC TTGGATGGGG GCCCACAGGG CCGGTGTGCT GTTGAGCCAG GACTGTGCTG    1200
```

```
GCACCCCACA GGGAGCCTTG GAGCCCTGCG TCCAGGAGGC CACTGCACTG CTCACTTGTG    1260

GCCCAGCGCG TCCTTGGAAA TCTGTGGCCC TGGAGGAGGA ACAGGAGGGC CCTGGGACCA    1320

GGCTCCCGGG GAACCTGAGC TCAGAGGATG TGCTGCCAGC AGGGTGTACG GAGTGGAGGG    1380

TACAGACGCT TGCCTATCTG CCACAGGAGG ACTGGGCCCC CACGTCCCTG ACTAGGCCGG    1440

CTCCCCCAGA CTCAGAGGGC AGCAGGAGCA GCAGCAGCAG CAGCAGCAGC AGCAACAACA    1500

ACAACTACTG TGCCTTGGGC TGCTATGGGG GATGGCACCT CTCAGCCCTC CCAGGAAACA    1560

CACAGAGCTC TGGGCCCATC CCAGCCCTGG CCTGTGGCCT TTCTTGTGAC CATCAGGGCC    1620

TGGAGACCCA GCAAGGAGTT GCCTGGGTGC TGGCTGGTCA CTGCCAGAGG CCTGGGCTGC    1680

ATGAGGACCT CCAGGGCATG TTGCTCCCTT CTGTCCTCAG CAAGGCTCGG TCCTGGACAT    1740

TCTAGGTCCC TGACTCGCCA GATGCATCAT GTCCATTTTG GGAAAATGGA CTGAAGTTTC    1800

TGGAGCCCTT GTCTGAGACT GAACCTCCTG AGAAGGGGCC CCTAGCAGCG GTCAGAGGTC    1860

CTGTCTGGAT GGAGGCTGGA GGCTCCCCCC TCAACCCCTC TGCTCAGTGC CTGTGGGGAG    1920

CAGCCTCTAC CCTCAGCATC CTGG                                          1944

(2) INFORMATION FOR SEQ ID NO: 4:

(i) SEQUENCE CHARACTERISTICS:
        (A) LENGTH: 1862 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 4:

AGCAGCTCTG TAATGCGCTT GTGGTTTCAG ATGTGGGCGG CCTGTGTGAA CCTGTCGTGC      60

AAAGCTCACG TCACCAACTG CTGCAGTTAT CTCCTGAATC AGGCTGAGGG TCTTTGCTGT     120

GCACCCAGAG ATAGTTGGGT GACAAATCAC CTCCAGGTTG GGGATGCCTC AGACTTGTGA     180

TGGGACTGGG CAGATGCATC TGGGAAGGCT GGACCTTGGA GAGTGAGGCC CTGAGGCGAG     240

ACATGGGCAC CTGGCTCCTG GCCTGCATCT GCATCTGCAC CTGTGTCTGC TTGGGAGTCT     300

CTGTCACAGG GGAAGGACAA GGGCCAAGGT CTAGAACCTT CACCTGCCTC ACCAACAACA     360

TTCTCAGGAT CGATTGCCAC TGGTCTGCCC CAGAGCTGGG ACAGGGCTCC AGCCCCTGGC     420

TCCTCTTCAC CAGCAACCAG GCTCCTGGCG GCACACATAA GTGCATCTTG CGGGGCAGTG     480

AGTGCACCGT CGTGCTGCCA CCTGAGGCAG TGCTCGTGCC ATCTGACAAT TCACCATCA      540

CTTTCCACCA CTGCATGTCT GGGAGGGAGC AGGTCAGCCT GGTGGACCCG GAGTACCTGC     600

CCCGGAGACA CGTTAAGCTG GACCCGCCCT CTGACTTGCA GAGCAACATC AGTTCTGGCC     660

ACTGCATCCT GACCTGGAGC ATCAGTCCTG CCTTGGAGCC AATGACCACA CTTCTCAGCT     720

ATGAGCTGGC CTTCAAGAAG CAGGAAGAGG CCTGGGAGCA GGCCCAGCAC AGGGATCACA     780

TTGTCGGGGT GACCTGGCTT ATACTTGAAG CCTTTGAGCT GGACCCTGGC TTTATCCATG     840

AGGCCAGGCT GCGTGTCCAG ATGGCCACAC TGGAGGATGA TGTGGTAGAG GAGGAGCGTT     900

ATACAGGCCA GTGGAGTGAG TGGAGCCAGC CTGTGTGCTT CCAGGCTCCC AGAGACAAG     960

GCCCTCTGAT CCCACCCTGG GGGTGGCCAG GCAACACCCT TGTTGCTGTG TCCATCTTTC    1020

TCCTGCTGAC TGGCCCGACC TACCTCCTGT TCAAGCTGTC GCCCAGACTT GGATGGGGGC    1080

CCACAGGGC GGTGTGCTGT TGAGCCAGGA CTGTGCTGGC ACCCCACAGG GAGCCTTGGA    1140

GCCCTGCGTC CAGGAGGCCA CTGCACTGCT CACTTGTGGC CCAGCGCGTC CTTGGAAATC    1200
```

```
TGTGGCCCTG GAGGAGGAAC AGGAGGGCCC TGGGACCAGG CTCCCGGGGA ACCTGAGCTC    1260

AGAGGATGTG CTGCCAGCAG GGTGTACGGA GTGGAGGGTA CAGACGCTTG CCTATCTGCC    1320

ACAGGAGGAC TGGGCCCCCA CGTCCCTGAC TAGGCCGGCT CCCCCAGACT CAGAGGGCAG    1380

CAGGAGCAGC AGCAGCAGCA GCAGCAGCAG CAACAACAAC AACTACTGTG CCTTGGGCTG    1440

CTATGGGGGA TGGCACCTCT CAGCCCTCCC AGGAAACACA CAGAGCTCTG GGCCCATCCC    1500

AGCCCTGGCC TGTGGCCTTT CTTGTGACCA TCAGGGCCTG GAGACCCAGC AAGGAGTTGC    1560

CTGGGTGCTG GCTGGTCACT GCCAGAGGCC TGGGCTGCAT GAGGACCTCC AGGGCATGTT    1620

GCTCCCTTCT GTCCTCAGCA AGGCTCGGTC CTGGACATTC TAGGTCCCTG ACTCGCCAGA    1680

TGCATCATGT CCATTTTGGG AAAATGGACT GAAGTTTCTG GAGCCCTTGT CTGAGACTGA    1740

ACCTCCTGAG AAGGGGCCCC TAGCAGCGGT CAGAGGTCCT GTCTGGATGG AGGCTGGAGG    1800

CTCCCCCCTC AACCCCTCTG CTCAGTGCCT GTGGGGAGCA GCCTCTACCC TCAGCATCCT    1860

GG                                                                  1862

(2) INFORMATION FOR SEQ ID NO: 5:

(i) SEQUENCE CHARACTERISTICS:
        (A) LENGTH: 195 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..195
        (D) OTHER INFORMATION: /note= "Base no. 1 corresponds to base
            no. 243 of Fig. 8.  The numbering in Fig. 8 matches
            SEQ ID NO:1."

(xi) SEQUENCE DESCRIPTION: SEQ ID NO: 5:

ATGGGCACCT GGCTCCTGGC CTGCATCTGC ATCTGCACCT GTGTCTGCTT GGGAGTCTCT     60

GTCACAGGGG AAGGACAAGG GCCAAGGTCT AGAACCTTCA CCTGCCTCAC CAACAACATT    120

CTCAGGATCG ATTGCCACTG GTCTGCCCCA GAGCTGGGAC AGGGCTCCAG CCCCTGGCTC    180

CTCTTCACCA GTTAA                                                    195

(2) INFORMATION FOR SEQ ID NO: 6:

(i) SEQUENCE CHARACTERISTICS:
        (A) LENGTH: 513 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..513
        (D) OTHER INFORMATION: /note= "Base no. 1 corresponds to base
            no. 208 of Fig. 6.  The numbering in Fig. 6 matches
            SEQ ID NO:1."

(xi) SEQUENCE DESCRIPTION: SEQ ID NO: 6:

GCTGGACCTT GGAGAGTGAG GCCCTGAGGC GAGACATGGG CACCTGGCTC CTGGCCTGCA     60

TCTGCATCTG CACCTGTGTC TGCTTGGGAG TCTCTGTCAC AGGGGAAGGA CAAGGGCCAA    120

GGTCTAGAAC CTTCACCTGC CTCACCAACA ACATTCTCAG GATCGATTGC CACTGGTCTG    180
```

```
CCCCAGAGCT GGGACAGGGC TCCAGCCCCT GGCTCCTCTT CACCAGCAAC CAGGCTCCTG      240

GCGGCACACA TAAGTGCATC TTGCGGGGCA GTGAGTGCAC CGTCGTGCTG CCACCTGAGG      300

CAGTGCTCGT GCCATCTGAC AATTTCACCA TCACTTTCCA CCACTGCATG TCTGGGAGGGG     360

AGCAGGTCAG CCTGGTGGAC CCGGAGTACC TGCCCCGGAG ACACGCTGGA CCCGCCCTCT     420

GACTTGCAGA GCAACATCAG TTCTGGCCAC TGCATCCTGA CCTGGAGCAT CAGTCCTGCC     480

TTGGAGCCAA TGACCACACT TCTCAGCTAT GAG                                  513
```

(2) INFORMATION FOR SEQ ID NO: 7:

(i) SEQUENCE CHARACTERISTICS:
        (A) LENGTH: 513 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..513
        (D) OTHER INFORMATION: /note= "Base no. 1 corresponds to base
            no. 208 of Fig. 7. The numbering in Fig. 7 matches
            SEQ ID NO:1."

(xi) SEQUENCE DESCRIPTION: SEQ ID NO: 7:

```
GCTGGACCTT GGAGAGTGAG GCCCTGAGGC GAGACATGGG CACCTGGCTC CTGGCCTGCA       60

TCTGCATCTG CACCTGTGTC TGCTTGGGAG TCTCTGTCAC AGGGGAAGGA CAAGGGCCAA      120

GGTCTAGAAC CTTCACCTGC CTCACCAACA ACATTCTCAG GATCGATTGC CACTGGTCTG      180

CCCCAGAGCT GGGACAGGGC TCCAGCCCCT GGCTCCTCTT CACCAGCAAC CAGGCTCCTG      240

GCGGCACACA TAAGTGCATC TTGCGGGGCA GTGAGTGCAC CGTCGTGCTG CCACCTGAGG      300

CAGTGCTCGT GCCATCTGAC AATTTCACCA TCACTTTCCA CCACTGCATG TCTGGGAGGG      360

AGCAGGTCAG CCTGGTGGAC CCGGAGTACC TGCCCCGGAG ACACGAGCAA CATCAGTTCT     420

GGCCACTGCA TCCTGACCTG GAGCATCAGT CCTGCCTTGG AGCCAATGAC CACACTTCTC     480

AGCTATGAGC TGGCCTTCAA GAAGCAGGAA GAG                                  513
```

(2) INFORMATION FOR SEQ ID NO: 8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 8:

```
GCAGGTGGGG ACCCATG                                                     17
```

(2) INFORMATION FOR SEQ ID NO: 9:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 9:

```
AGGCTTGACA TCGGACAAC                                                   19
```

(2) INFORMATION FOR SEQ ID NO: 10:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 10:

CTGGCCTGAA GTACTTACC                                     19

(2) INFORMATION FOR SEQ ID NO: 11:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 11:

CTGCTTCAAT CCTGGGGAA                                     19

(2) INFORMATION FOR SEQ ID NO: 12:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 12:

GTGAGTTCCC CAGGATTGA                                     19

(2) INFORMATION FOR SEQ ID NO: 13:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 13:

CAAGGCCCTG CTCCAAA                                       17

(2) INFORMATION FOR SEQ ID NO: 14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 14:

TGGGGCTTCA GCCTCACATG                                   20

(2) INFORMATION FOR SEQ ID NO: 15:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO: 15:

TATGTAGAGT GGGGAGTCTA                                                         20

(2) INFORMATION FOR SEQ ID NO: 16:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO: 16:

TGTATTCTCG AGGGCTGAG                                                          19

(2) INFORMATION FOR SEQ ID NO: 17:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO: 17:

TGAGGTGAAC AGGGGAGAA                                                          19

(2) INFORMATION FOR SEQ ID NO: 18:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO: 18:

CCCTGGGCCC TTCATGT                                                            17

(2) INFORMATION FOR SEQ ID NO: 19:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO: 19:

ACAAGGGCGG CCTTTGAT                                                           18

(2) INFORMATION FOR SEQ ID NO: 20:

(i) SEQUENCE CHARACTERISTICS:
            (A) LENGTH: 19 base pairs
            (B) TYPE: nucleic acid
            (C) STRANDEDNESS: single (D) TOPOLOGY: linear (ii) MOLECULE TYPE: other nucleic acid (xi) SEQUENCE DESCRIPTION: SEQ ID NO: 20:

AGGGACGAGG TGGGCGGAC                                                  19

(2) INFORMATION FOR SEQ ID NO: 21:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 21:

CCTGCCCCCC ATGTTCTT                                                   18

(2) INFORMATION FOR SEQ ID NO: 22:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 22:

ATGCTACCTG AGCCCTTCC                                                  19

(2) INFORMATION FOR SEQ ID NO: 23:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 23:

GGACATGATG CATCTGGCG                                                  19

(2) INFORMATION FOR SEQ ID NO: 24:

(i) SEQUENCE CHARACTERISTICS:
        (A) LENGTH: 1944 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: mutation
        (B) LOCATION: 1506..1508
        (D) OTHER INFORMATION: /note= "This codon in the wild type is
            deleted."

(xi) SEQUENCE DESCRIPTION: SEQ ID NO: 24:

AGCAGCTCTG TAATGCGCTT GTGGTTTCAG ATGTGGGCGG CCTGTGTGAA CCTGTCGTGC     60

AAAGCTCACG TCACCAACTG CTGCAGTTAT CTCCTGAATC AGGCTGAGGG TCTTTGCTGT    120

GCACCCAGAG ATAGTTGGGT GACAAATCAC CTCCAGGTTG GGGATGCCTC AGACTTGTGA    180

TGGGACTGGG CAGATGCATC TGGGAAGGCT GGACCTTGGA GAGTGAGGCC CTGAGGCGAG    240

```
ACATGGGCAC CTGGCTCCTG GCCTGCATCT GCATCTGCAC CTGTGTCTGC TTGGGAGTCT    300

CTGTCACAGG GGAAGGACAA GGGCCAAGGT CTAGAACCTT CACCTGCCTC ACCAACAACA    360

TTCTCAGGAT CGATTGCCAC TGGTCTGCCC CAGAGCTGGG ACAGGGCTCC AGCCCCTGGC    420

TCCTCTTCAC CAGCAACCAG GCTCCTGGCG GCACACATAA GTGCATCTTG CGGGGCAGTG    480

AGTGCACCGT CGTGCTGCCA CCTGAGGCAG TGCTCGTGCC ATCTGACAAT TTCACCATCA    540

CTTTCCACCA CTGCATGTCT GGGAGGGAGC AGGTCAGCCT GGTGGACCCG GAGTACCTGC    600

CCCGGAGACA CGTTAAGCTG GACCCGCCCT CTGACTTGCA GAGCAACATC AGTTCTGGCC    660

ACTGCATCCT GACCTGGAGC ATCAGTCCTG CCTTGGAGCC AATGACCACA CTTCTCAGCT    720

ATGAGCTGGC CTTCAAGAAG CAGGAAGAGG CCTGGGAGCA GGCCCAGCAC AGGGATCACA    780

TTGTCGGGGT GACCTGGCTT ATACTTGAAG CCTTTGAGCT GGACCCTGGC TTTATCCATG    840

AGGCCAGGCT GCGTGTCCAG ATGGCCACAC TGGAGGATGA TGTGGTAGAG GAGGAGCGTT    900

ATACAGGCCA GTGGAGTGAG TGGAGCCAGC CTGTGTGCTT CCAGGCTCCC CAGAGACAAG    960

GCCCTCTGAT CCCACCCTGG GGGTGGCCAG GCAACACCCT TGTTGCTGTG TCCATCTTTC   1020

TCCTGCTGAC TGGCCCGACC TACCTCCTGT TCAAGCTGTC GCCCAGGGTG AAGAGAATCT   1080

TCTACCAGAA CGTGCCCTCT CCAGCGATGT TCTTCCAGCC CCTCTACAGT GTACACAATG   1140

GGAACTTCCA GACTTGGATG GGGGCCCACA GGGCCGGTGT GCTGTTGAGC CAGGACTGTG   1200

CTGGCACCCC ACAGGGAGCC TTGGAGCCCT GCGTCCAGGA GGCCACTGCA CTGCTCACTT   1260

GTGGCCCAGC GCGTCCTTGG AAATCTGTGG CCCTGGAGGA GGAACAGGAG GGCCCTGGGA   1320

CCAGGCTCCC GGGGAACCTG AGCTCAGAGG ATGTGCTGCC AGCAGGGTGT ACGGACTGGA   1380

GGGTACAGAC GCTTGCCTAT CTGCCACAGG AGGACTGGGC CCCCACGTCC CTGACTAGGC   1440

CGGCTCCCCC AGACTCAGAG GGCAGCAGGA GCAGCAGCAG CAGCAGCAGC AGCAGCAACA   1500

ACAACTACTG TGCCTTGGGC TGCTATGGGG GATGGCACCT CTCAGCCCTC CCAGGAAACA   1560

CACAGAGCTC TGGGCCCATC CCAGCCCTGG CCTGTGGCCT TTCTTGTGAC CATCAGGGCC   1620

TGGAGACCCA GCAAGGAGTT GCCTGGGTGC TGGCTGGTCA CTGCCAGAGG CCTGGGCTGC   1680

ATGAGGACCT CCAGGGCATG TTGCTCCCTT CTGTCCTCAG CAAGGCTCGG TCCTGGACAT   1740

TCTAGGTCCC TGACTCGCCA GATGCATCAT GTCCATTTTG GGAAAATGGA CTGAAGTTTC   1800

TGGAGCCCTT GTCTGAGACT GAACCTCCTG AGAAGGGGCC CCTAGCAGCG GTCAGAGGTC   1860

CTGTCTGGAT GGAGGCTGGA GGCTCCCCCC TCAACCCCTC TGCTCAGTGC CTGTGGGGAG   1920

CAGCCTCTAC CCTCAGCATC CTGG                                         1944
```

(2) INFORMATION FOR SEQ ID NO: 25:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 25:

```
GCTGGACCTT GGAGAGTG                                                   18
```

(2) INFORMATION FOR SEQ ID NO: 26:

(i) SEQUENCE CHARACTERISTICS:
        (A) LENGTH: 20 base pairs

-continued

```
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 26:

GTCTCAGACA AGGGCTCCAG                                                   20

(2) INFORMATION FOR SEQ ID NO: 27:

(i) SEQUENCE CHARACTERISTICS:
        (A) LENGTH: 501 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 27:

Met Gly Thr Trp Leu Leu Ala Cys Ile Cys Ile Cys Thr Cys Val
1               5                   10                  15

Leu Gly Val Ser Val Thr Gly Glu Gly Gln Gly Pro Arg Ser Arg
            20                  25                  30

Phe Thr Cys Leu Thr Asn Asn Ile Leu Arg Ile Asp Cys His Trp
        35                  40                  45

Ala Pro Glu Leu Gly Gln Gly Ser Ser Pro Trp Leu Leu Phe Thr
    50                  55                  60

Asn Gln Ala Pro Gly Gly Thr His Lys Cys Ile Leu Arg Gly Ser
65                  70                  75                  80

Cys Thr Val Val Leu Pro Pro Glu Ala Val Leu Val Pro Ser Asp
                85                  90                  95

Phe Thr Ile Thr Phe His His Cys Met Ser Gly Arg Glu Gln Val
            100                 105                 110

Leu Val Asp Pro Glu Tyr Leu Pro Arg Arg His Val Lys Leu Asp
        115                 120                 125

Pro Ser Asp Leu Gln Ser Asn Ile Ser Ser Gly His Cys Ile Leu
    130                 135                 140

Trp Ser Ile Ser Pro Ala Leu Glu Pro Met Thr Thr Leu Leu Ser
145                 150                 155                 160

Glu Leu Ala Phe Lys Lys Gln Glu Glu Ala Trp Glu Gln Ala Gln
                165                 170                 175

Arg Asp His Ile Val Gly Val Thr Trp Leu Ile Leu Glu Ala Phe
            180                 185                 190

Leu Asp Pro Gly Phe Ile His Glu Ala Arg Leu Arg Val Gln Met
        195                 200                 205

Thr Leu Glu Asp Asp Val Val Glu Glu Glu Arg Tyr Thr Gly Gln
    210                 215                 220

Ser Glu Trp Ser Gln Pro Val Cys Phe Gln Ala Pro Gln Arg Gln
225                 230                 235                 240

Pro Leu Ile Pro Pro Trp Gly Trp Pro Gly Asn Thr Leu Val Ala
                245                 250                 255

Ser Ile Phe Leu Leu Leu Thr Gly Pro Thr Tyr Leu Leu Phe Lys
            260                 265                 270

Ser Pro Arg Val Lys Arg Ile Phe Tyr Gln Asn Val Pro Ser Pro
        275                 280                 285

Met Phe Phe Gln Pro Leu Tyr Ser Val His Asn Gly Asn Phe Gln
    290                 295                 300
```

```
Trp Met Gly Ala His Arg Ala Gly Val Leu Leu Ser Gln Asp Cys
305                 310                 315                 320

Gly Thr Pro Gln Gly Ala Leu Glu Pro Cys Val Gln Glu Ala Thr
                325                 330                 335

Leu Leu Thr Cys Gly Pro Ala Arg Pro Trp Lys Ser Val Ala Leu
            340                 345                 350

Glu Glu Gln Glu Gly Pro Gly Thr Arg Leu Pro Gly Asn Leu Ser
        355                 360                 365

Glu Asp Val Leu Pro Ala Gly Cys Thr Glu Trp Arg Val Gln Thr
370                 375                 380

Ala Tyr Leu Pro Gln Glu Asp Trp Ala Pro Thr Ser Leu Thr Arg
385                 390                 395                 400

Ala Pro Pro Asp Ser Glu Gly Ser Arg Ser Ser Ser Ser Ser Ser
                405                 410                 415

Ser Ser Asn Asn Asn Asn Tyr Cys Ala Leu Gly Cys Tyr Gly Gly
                420                 425                 430

His Leu Ser Ala Leu Pro Gly Asn Thr Gln Ser Ser Gly Pro Ile
            435                 440                 445

Ala Leu Ala Cys Gly Leu Ser Cys Asp His Gln Gly Leu Glu Thr
450                 455                 460

Gln Gly Val Ala Trp Val Leu Ala Gly His Cys Gln Arg Pro Gly
465                 470                 475                 480

His Glu Asp Leu Gln Gly Met Leu Leu Pro Ser Val Leu Ser Lys
                485                 490                 495

Arg Ser Trp Thr Phe
            500

(2) INFORMATION FOR SEQ ID NO: 28:

(i) SEQUENCE CHARACTERISTICS:
        (A) LENGTH: 501 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 28:

Met Gly Thr Trp Leu Ala Cys Ile Cys Ile Cys Thr Cys Val
1               5                   10                  15

Leu Gly Val Ser Val Thr Gly Glu Gly Gln Pro Arg Ser Arg
            20                  25                  30

Phe Thr Cys Leu Thr Asn Asn Ile Leu Arg Ile Asp Cys His Trp
            35                  40                  45

Ala Pro Glu Leu Gly Gln Gly Ser Ser Pro Trp Leu Leu Phe Thr
50                  55                  60

Asn Gln Ala Pro Gly Gly Thr His Lys Cys Ile Leu Arg Gly Ser
65                  70                  75                  80

Cys Thr Val Val Leu Pro Pro Glu Ala Val Leu Val Pro Ser Asp
                85                  90                  95

Phe Thr Ile Thr Phe His His Cys Met Ser Gly Arg Glu Gln Val
                100                 105                 110

Leu Val Asp Pro Glu Tyr Leu Pro Arg Arg His Val Lys Leu Asp
            115                 120                 125

Pro Ser Asp Leu Gln Ser Asn Ile Ser Ser Gly His Cys Ile Leu
            130                 135                 140
```

```
Trp Ser Ile Ser Pro Ala Leu Glu Pro Met Thr Thr Leu Leu Ser
145                 150                 155                 160

Glu Leu Ala Phe Lys Lys Gln Glu Glu Ala Trp Gln Ala Gln
        165                 170                 175

Arg Asp His Ile Val Gly Val Thr Trp Leu Ile Leu Glu Ala Phe
            180                 185                 190

Leu Asp Pro Gly Phe Ile His Glu Ala Arg Leu Arg Val Gln Met
            195                 200                 205

Thr Leu Glu Asp Asp Val Val Glu Glu Arg Tyr Thr Gly Gln
    210                 215                 220

Ser Glu Trp Ser Gln Pro Val Cys Phe Gln Ala Pro Gln Arg Gln
225                 230                 235                 240

Pro Leu Ile Pro Pro Trp Gly Trp Pro Gly Asn Thr Leu Val Ala
                245                 250                 255

Ser Ile Phe Leu Leu Leu Thr Gly Pro Thr Tyr Leu Leu Phe Lys
            260                 265                 270

Ser Pro Arg Val Lys Arg Ile Phe Tyr Gln Asn Val Pro Ser Pro
    275                 280                 285

Met Phe Phe Gln Pro Leu Tyr Ser Val His Asn Gly Asn Phe Gln
    290                 295                 300

Trp Met Gly Ala His Arg Ala Gly Val Leu Leu Ser Gln Asp Cys
305                 310                 315                 320

Gly Thr Pro Gln Gly Ala Leu Glu Pro Cys Val Gln Glu Ala Thr
                325                 330                 335

Leu Leu Thr Cys Gly Pro Ala His Pro Trp Lys Ser Val Ala Leu
            340                 345                 350

Glu Glu Gln Glu Gly Pro Gly Thr Arg Leu Pro Gly Asn Leu Ser
            355                 360                 365

Glu Asp Val Leu Pro Ala Gly Cys Thr Glu Trp Arg Val Gln Thr
    370                 375                 380

Ala Tyr Leu Pro Gln Glu Asp Trp Ala Pro Thr Ser Leu Thr Arg
385                 390                 395                 400

Ala Pro Pro Asp Ser Glu Gly Ser Arg Ser Ser Ser Ser Ser
            405                 410                 415

Ser Ser Asn Asn Asn Asn Tyr Cys Ala Leu Gly Cys Tyr Gly Gly
            420                 425                 430

His Leu Ser Ala Leu Pro Gly Asn Thr Gln Ser Ser Gly Pro Ile
        435                 440                 445

Ala Leu Ala Cys Gly Leu Ser Cys Asp His Gln Gly Leu Glu Thr
        450                 455                 460

Gln Gly Val Ala Trp Val Leu Ala Gly His Cys Gln Arg Pro Gly
465                 470                 475                 480

His Glu Asp Leu Gln Gly Met Leu Leu Pro Ser Val Leu Ser Lys
            485                 490                 495

Arg Ser Trp Thr Phe
            500

(2) INFORMATION FOR SEQ ID NO: 29:

(i) SEQUENCE CHARACTERISTICS:
        (A) LENGTH: 500 amino acids
        (B) TYPE: amino acid
        (C) STRANDEDNESS: single
        (D) TOPOLOGY: linear
```

(ii) MOLECULE TYPE: peptide (xi) SEQUENCE DESCRIPTION: SEQ ID NO: 29:

```
Met Gly Thr Trp Leu Leu Ala Cys Ile Cys Ile Cys Thr Cys Val
1               5                   10                  15

Leu Gly Val Ser Val Thr Gly Glu Gly Gln Gly Pro Arg Ser Arg
                20                  25                  30

Phe Thr Cys Leu Thr Asn Asn Ile Leu Arg Ile Asp Cys His Trp
                35                  40                  45

Ala Pro Glu Leu Gly Gln Gly Ser Ser Pro Trp Leu Leu Phe Thr
50                  55                      60

Asn Gln Ala Pro Gly Gly Thr His Lys Cys Ile Leu Arg Gly Ser
65                  70                  75                  80

Cys Thr Val Val Leu Pro Pro Glu Ala Val Leu Val Pro Ser Asp
                85                  90                  95

Phe Thr Ile Thr Phe His His Cys Met Ser Gly Arg Glu Gln Val
                100                 105                 110

Leu Val Asp Pro Glu Tyr Leu Pro Arg Arg His Val Lys Leu Asp
                115                 120                 125

Pro Ser Asp Leu Gln Ser Asn Ile Ser Ser Gly His Cys Ile Leu
130                 135                     140

Trp Ser Ile Ser Pro Ala Leu Glu Pro Met Thr Thr Leu Leu Ser
145                 150                 155                 160

Glu Leu Ala Phe Lys Lys Gln Glu Glu Ala Trp Glu Ala Gln His
                165                 170                 175

Asp His Ile Val Gly Val Thr Trp Leu Ile Leu Glu Ala Phe Glu
                180                 185                 190

Asp Pro Gly Phe Ile His Glu Ala Arg Leu Arg Val Gln Met Ala
                195                 200                 205

Leu Glu Asp Asp Val Val Glu Glu Glu Arg Tyr Thr Gly Gln Trp
210                 215                     220

Glu Trp Ser Gln Pro Val Cys Phe Gln Ala Pro Gln Arg Gln Gly
225                 230                 235                 240

Leu Ile Pro Pro Trp Gly Trp Pro Gly Asn Thr Leu Val Ala Val
                245                 250                 255

Ile Phe Leu Leu Leu Thr Gly Pro Thr Tyr Leu Leu Phe Lys Leu
                260                 265                 270

Pro Arg Val Lys Arg Ile Phe Tyr Gln Asn Val Pro Ser Pro Ala
                275                 280                 285

Phe Phe Gln Pro Leu Tyr Ser Val His Asn Gly Asn Phe Gln Thr
290                 295                     300

Met Gly Ala His Arg Ala Gly Val Leu Leu Ser Gln Asp Cys Ala
305                 310                 315                 320

Thr Pro Gln Gly Ala Leu Glu Pro Cys Val Gln Glu Ala Thr Ala
                325                 330                 335

Leu Thr Cys Gly Pro Ala Arg Pro Trp Lys Ser Val Ala Leu Glu
                340                 345                 350

Glu Gln Glu Gly Pro Gly Thr Arg Leu Pro Gly Asn Leu Ser Ser
                355                 360                 365

Asp Val Leu Pro Ala Gly Cys Thr Glu Trp Arg Val Gln Thr Leu
                370                 375                 380

Tyr Leu Pro Gln Glu Asp Trp Ala Pro Thr Ser Leu Thr Arg Pro
385                 390                 395                 400
```

```
Pro Pro Asp Ser Glu Gly Ser Arg Ser Ser Ser Ser Ser
            405                 410                 415

Ser Asn Asn Asn Asn Tyr Cys Ala Leu Gly Cys Tyr Gly Gly Trp
                420                 425                 430

Leu Ser Ala Leu Pro Gly Asn Thr Gln Ser Ser Gly Pro Ile Pro
            435                 440                 445

Leu Ala Cys Gly Leu Ser Cys Asp His Gln Gly Leu Glu Thr Gln
            450                 455                 460

Gly Val Ala Trp Val Leu Ala Gly His Cys Gln Arg Pro Gly Leu
465                 470                 475                 480

Glu Asp Leu Gln Gly Met Leu Leu Pro Ser Val Leu Ser Lys Ala
                485                 490                 495

Ser Trp Thr Phe
            500

(2) INFORMATION FOR SEQ ID NO: 30:

(i) SEQUENCE CHARACTERISTICS:
        (A) LENGTH: 286 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 30:

Met Gly Thr Trp Leu Leu Ala Cys Ile Cys Ile Cys Thr Cys Val
1               5                   10                  15

Leu Gly Val Ser Val Thr Gly Glu Gly Gln Gly Pro Arg Ser Arg
                20                  25                  30

Phe Thr Cys Leu Thr Asn Asn Ile Leu Arg Ile Asp Cys His Trp
            35                  40                  45

Ala Pro Glu Leu Gly Gln Gly Ser Ser Pro Trp Leu Leu Phe Thr
        50                  55                  60

Asn Gln Ala Pro Gly Gly Thr His Lys Cys Ile Leu Arg Gly Ser
65              70                  75                  80

Cys Thr Val Val Leu Pro Pro Glu Ala Val Leu Val Pro Ser Asp
                85                  90                  95

Phe Thr Ile Thr Phe His His Cys Met Ser Gly Arg Glu Gln Val
            100                 105                 110

Leu Val Asp Pro Glu Tyr Leu Pro Arg Arg His Val Lys Leu Asp
            115                 120                 125

Pro Ser Asp Leu Gln Ser Asn Ile Ser Ser Gly His Cys Ile Leu
            130                 135                 140

Trp Ser Ile Ser Pro Ala Leu Glu Pro Met Thr Thr Leu Leu Ser
145                 150                 155                 160

Glu Leu Ala Phe Lys Lys Gln Glu Glu Ala Trp Glu Gln Ala Gln
                165                 170                 175

Arg Asp His Ile Val Gly Val Thr Trp Leu Ile Leu Glu Ala Phe
            180                 185                 190

Leu Asp Pro Gly Phe Ile His Glu Ala Arg Leu Arg Val Gln Met
            195                 200                 205

Thr Leu Glu Asp Asp Val Val Glu Glu Arg Tyr Thr Gly Gln
            210                 215                 220

Ser Glu Trp Ser Gln Pro Val Cys Phe Gln Ala Pro Gln Arg Gln
225                 230                 235                 240
```

```
Pro Leu Ile Pro Pro Trp Gly Trp Pro Gly Asn Thr Leu Val Ala
            245                 250                 255

Ser Ile Phe Leu Leu Leu Thr Gly Pro Thr Tyr Leu Leu Phe Lys
            260                 265                 270

Ser Pro Arg Leu Gly Trp Gly Pro Thr Gly Pro Val Cys Cys
            275                 280                 285
```

(2) INFORMATION FOR SEQ ID NO: 31:

(i) SEQUENCE CHARACTERISTICS:
        (A) LENGTH: 64 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 31:

```
Met Gly Thr Trp Leu Leu Ala Cys Ile Cys Ile Cys Thr Cys Val
1               5                   10                  15

Leu Gly Val Ser Val Thr Gly Glu Gly Gln Gly Pro Arg Ser Arg
            20                  25                  30

Phe Thr Cys Leu Thr Asn Asn Ile Leu Arg Ile Asp Cys His Trp
            35                  40                  45

Ala Pro Glu Leu Gly Gln Gly Ser Ser Pro Trp Leu Leu Phe Thr
50                  55                  60
```

(2) INFORMATION FOR SEQ ID NO: 32:

(i) SEQUENCE CHARACTERISTICS:
        (A) LENGTH: 128 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 32:

```
Met Gly Thr Trp Leu Leu Ala Cys Ile Cys Ile Cys Thr Cys Val
1               5                   10                  15

Leu Gly Val Ser Val Thr Gly Glu Gly Gln Gly Pro Arg Ser Arg
            20                  25                  30

Phe Thr Cys Leu Thr Asn Asn Ile Leu Arg Ile Asp Cys His Trp
            35                  40                  45

Ala Pro Glu Leu Gly Gln Gly Ser Ser Pro Trp Leu Leu Phe Thr
50                  55                  60

Asn Gln Ala Pro Gly Gly Thr His Lys Cys Ile Leu Arg Gly Ser
65                  70                  75                  80

Cys Thr Val Val Leu Pro Pro Glu Ala Val Leu Val Pro Ser Asp
            85                  90                  95

Phe Thr Ile Thr Phe His His Cys Met Ser Gly Arg Glu Gln Val
            100                 105                 110

Leu Val Asp Pro Glu Tyr Leu Pro Arg Arg His Ala Gly Pro Ala
            115                 120                 125
```

(2) INFORMATION FOR SEQ ID NO: 33:

(i) SEQUENCE CHARACTERISTICS:
        (A) LENGTH: 150 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 33:

Met Gly Thr Trp Leu Leu Ala Cys Ile Cys Ile Cys Thr Cys Val
1               5                   10                  15

Leu Gly Val Ser Val Thr Gly Glu Gly Gln Gly Pro Arg Ser Arg
                20                  25                  30

Phe Thr Cys Leu Thr Asn Asn Ile Leu Arg Ile Asp Cys His Trp
                35                  40                  45

Ala Pro Glu Leu Gly Gln Gly Ser Ser Pro Trp Leu Leu Phe Thr
50                  55                  60

Asn Gln Ala Pro Gly Gly Thr His Lys Cys Ile Leu Arg Gly Ser
65                  70                  75                  80

Cys Thr Val Val Leu Pro Pro Glu Ala Val Leu Val Pro Ser Asp
                85                  90                  95

Phe Thr Ile Thr Phe His His Cys Met Ser Gly Arg Glu Gln Val
                100                 105                 110

Leu Val Asp Pro Glu Tyr Leu Pro Arg Arg His Glu Gln His Gln
                115                 120                 125

Trp Pro Leu His Pro Asp Leu Glu His Gln Ser Cys Leu Gly Ala
                130                 135                 140

Asp His Thr Ser Gln Leu
145                 150

(2) INFORMATION FOR SEQ ID NO: 34:

(i) SEQUENCE CHARACTERISTICS:
        (A) LENGTH: 500 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: MUTATION
        (B) LOCATION: 422
        (D) OTHER INFORMATION: /note= "Asn at this position in
            the wild type is deleted."

(xi) SEQUENCE DESCRIPTION: SEQ ID NO: 34:

Met Gly Thr Trp Leu Leu Ala Cys Ile Cys Ile Cys Thr Cys Val Cys
1               5                   10                  15

Leu Gly Val Ser Val Thr Gly Glu Gly Gln Gly Pro Arg Ser Arg Thr
                20                  25                  30

Phe Thr Cys Leu Thr Asn Asn Ile Leu Arg Ile Asp Cys His Trp Ser
                35                  40                  45

Ala Pro Glu Leu Gly Gln Gly Ser Ser Pro Trp Leu Leu Phe Thr Ser
50                  55                  60

Asn Gln Ala Pro Gly Gly Thr His Lys Cys Ile Leu Arg Gly Ser Glu
65                  70                  75                  80

Cys Thr Val Val Leu Pro Pro Glu Ala Val Leu Val Pro Ser Asp Asn
                85                  90                  95

Phe Thr Ile Thr Phe His His Cys Met Ser Gly Arg Glu Gln Val Ser
                100                 105                 110

Leu Val Asp Pro Glu Tyr Leu Pro Arg Arg His Val Lys Leu Asp Pro
                115                 120                 125

Pro Ser Asp Leu Gln Ser Asn Ile Ser Ser Gly His Cys Ile Leu Thr

```
            130             135             140
Trp Ser Ile Ser Pro Ala Leu Glu Pro Met Thr Thr Leu Leu Ser Tyr
145             150             155             160

Glu Leu Ala Phe Lys Lys Gln Glu Glu Ala Trp Glu Gln Ala Gln His
                165             170             175

Arg Asp His Ile Val Gly Val Thr Trp Leu Ile Leu Glu Ala Phe Glu
            180             185             190

Leu Asp Pro Gly Phe Ile His Glu Ala Arg Leu Arg Val Gln Met Ala
            195             200             205

Thr Leu Glu Asp Asp Val Val Glu Glu Glu Arg Tyr Thr Gly Gln Trp
210             215             220

Ser Glu Trp Ser Gln Pro Val Cys Phe Gln Ala Pro Gln Arg Gln Gly
225             230             235             240

Pro Leu Ile Pro Pro Trp Gly Trp Pro Gly Asn Thr Leu Val Ala Val
            245             250             255

Ser Ile Phe Leu Leu Leu Thr Gly Pro Thr Tyr Leu Leu Phe Lys Leu
            260             265             270

Ser Pro Arg Val Lys Arg Ile Phe Tyr Gln Asn Val Pro Ser Pro Ala
            275             280             285

Met Phe Phe Gln Pro Leu Tyr Ser Val His Asn Gly Asn Phe Gln Thr
            290             295             300

Trp Met Gly Ala His Arg Ala Gly Val Leu Leu Ser Gln Asp Cys Ala
305             310             315             320

Gly Thr Pro Gln Gly Ala Leu Glu Pro Cys Val Gln Glu Ala Thr Ala
            325             330             335

Leu Leu Thr Cys Gly Pro Ala Arg Pro Trp Lys Ser Val Ala Leu Glu
            340             345             350

Glu Glu Gln Glu Gly Pro Gly Thr Arg Leu Pro Gly Asn Leu Ser Ser
            355             360             365

Glu Asp Val Leu Pro Ala Gly Cys Thr Glu Trp Arg Val Gln Thr Leu
            370             375             380

Ala Tyr Leu Pro Gln Glu Asp Trp Ala Pro Thr Ser Leu Thr Arg Pro
385             390             395             400

Ala Pro Pro Asp Ser Glu Gly Ser Arg Ser Ser Ser Ser Ser Ser Ser
            405             410             415

Ser Ser Asn Asn Asn Tyr Cys Ala Leu Gly Cys Tyr Gly Gly Trp His
            420             425             430

Leu Ser Ala Leu Pro Gly Asn Thr Gln Ser Ser Gly Pro Ile Pro Ala
            435             440             445

Leu Ala Cys Gly Leu Ser Cys Asp His Gln Gly Leu Glu Thr Gln Gln
450             455             460

Gly Val Ala Trp Val Leu Ala Gly His Cys Gln Arg Pro Gly Leu His
465             470             475             480

Glu Asp Leu Gln Gly Met Leu Leu Pro Ser Val Leu Ser Lys Ala Arg
            485             490             495

Ser Trp Thr Phe
            500

(2) INFORMATION FOR SEQ ID NO: 35:

(i) SEQUENCE CHARACTERISTICS:
        (A) LENGTH: 70 base pairs
        (B) TYPE: nucleic acid
        (C) STRANDEDNESS: single
        (D) TOPOLOGY: linear
```

-continued

```
        (ii) MOLECULE TYPE: cDNA (ix) FEATURE:
             (A) NAME/KEY: misc_feature
             (B) LOCATION: 1..70
             (D) OTHER INFORMATION: /note= "Base no. 1 corresponds to
                 base no. 81 of intron 5."

(xi) SEQUENCE DESCRIPTION: SEQ ID NO: 35:

AAGTGTGATG AGTGTGAAAG TGTTCCTGTA GACATGTTTG CCTGTGTGTG CATATGTGTA      60

TTTGTGGGCA                                                             70

(2) INFORMATION FOR SEQ ID NO: 36:

(i) SEQUENCE CHARACTERISTICS:
             (A) LENGTH: 70 base pairs
             (B) TYPE: nucleic acid
             (C) STRANDEDNESS: single
             (D) TOPOLOGY: linear (ii) MOLECULE TYPE: cDNA (ix) FEATURE:
             (A) NAME/KEY: misc_feature
             (B) LOCATION: 1..70
             (D) OTHER INFORMATION: /note= "Base no. 1 corresponds to base
                 no. 81 of intron 5."

(ix) FEATURE:
             (A) NAME/KEY: mutation
             (B) LOCATION: 133
             (D) OTHER INFORMATION: /note= "T to C substitution in intron
                 5."

(xi) SEQUENCE DESCRIPTION: SEQ ID NO: 36:

AAGTGTGATG AGTGTGAAAG TGTTCCTGTA GACATGTTTG CCTGTGTGTG CACATGTGTA      60

TTTGTGGGCA                                                             70
```

NUCLEIC ACID ENCODING AN INTERLEUKIN-9 RECEPTOR VARIANT

CROSS-REFERENCE TO RELATED APPLICATION

This is a divisional application of application Ser. No. 11/371,157 (filed Mar. 9, 2006; now U.S. Pat. No. 7,208,292, issued Apr. 24, 2007) which is divisional of application Ser. No. 10/320,646 (filed Dec. 17, 2002; now U.S. Pat. No. 7,056,698, issued Jun. 6, 2006) which is a divisional of application Ser. No. 09/596,377 (filed Jun. 16, 2000; now U.S. Pat. No. 6,602,850, issued Aug. 5, 2003) which is a divisional of application Ser. No. 08/980,872 (filed Dec. 1, 1997; now abandoned) which claims the benefit of Provisional Application No. 60/032,224 (filed Dec. 2, 1996) all of which are incorporated herein by reference in their entirety.

FIELD OF THE INVENTION

This invention describes biologic variability in the IL-9 receptor (Asthma Associated Factor 2) (SEQ ID NO: 1) and relates these sequence variants to susceptibility to asthma, atopic allergy, and related disorders. This invention also teaches methods that utilize these IL-9 receptor sequence variants for the diagnosis of susceptibility or resistance to asthma and atopic allergy. In addition, methods are described that use variant IL-9 receptors in the development of pharmaceuticals for asthma which depend on the regulation of IL-9 activity.

BACKGROUND OF THE INVENTION

Inflammation is a complex process in which the body's defense system combats foreign entities. While the battle against foreign entities may be necessary for the body's survival, some defense systems improperly respond to foreign entities, even innocuous ones, as dangerous and thereby damage surrounding tissue in the ensuing battle.

Atopic allergy is a disorder where genetic background dictates the response to environmental stimuli. The disorder is generally characterized by an increased ability of lymphocytes to produce IgE antibodies in response to ubiquitous antigens. Activation of the immune system by these antigens also leads to allergic inflammation which may occur after their ingestion, penetration through the skin, or after inhalation. When this immune activation occurs and pulmonary inflammation ensues, this disorder is broadly characterized as asthma. Certain cells are important in this inflammatory reaction in the airways and they include T cells and antigen presenting cells, B cells that produce IgE, and mast cells/basophils that store inflammatory mediators and bind IgE, and eosinophils that release additional mediators. These inflammatory cells accumulate at the site of allergic inflammation, and the toxic products they release contribute to the tissue destruction related to the disorder.

While asthma is generally defined as an inflammatory disorder of the airways, clinical symptoms arise from intermittent airflow obstruction. It is a chronic, disabling disorder that appears to be increasing in prevalence and severity.[1] It is estimated that 30-40% of the population suffer with atopic allergy, and 15% of children and 5% of adults in the population suffer from asthma.[1] Thus, an enormous burden is placed on our health-care resources in the treatment of these disorders.

Both the diagnosis and treatment of asthma and related disorders are problematic.[1] In particular, the assessment of inflamed lung tissue is often difficult, and frequently the cause of the inflammation cannot be determined. Although atopic asthma is an ecogenetic disorder, knowledge about the particular variant genes has only recently been discovered. Methods to detect these genetic variations and their role in inflammation, diagnosis and prognosis remain to be determined. What is needed in the art is the development of technology to expedite the diagnosis of atopic asthma that specifically relates to variation in genes responsible for susceptibility/resistance to this atopic disease.

Current treatments suffer their own set of disadvantages. The main therapeutic agents, β-agonists, reduce the symptoms, i.e., transiently improve pulmonary functions, but do not affect the underlying inflammation so that lung tissue remains in jeopardy. In addition, constant use of β-agonists results in desensitization which reduces their efficacy and safety.[2] The agents that can diminish the underlying inflammation, the anti-inflammatory steroids, have their own known list of side effects that range from immunosuppression to bone loss.[2]

Because of the problems associated with conventional therapies, alternative treatment strategies have been evaluated.[36-39] Glycophorin A,[37] cyclosporin,[38] and a nona peptide fragment of IL-2,[38] all inhibit interleukin-2 dependent T lymphocyte proliferation.[28] They are, however, known to have many other effects.[2] For example, cyclosporin is used as a immunosuppressant after organ transplantation. While these agents may represent alternatives to steroids in the treatment of asthmatics,[36-39] they inhibit interleukin-2 dependent T lymphocyte proliferation and potentially critical immune functions associated with homeostasis. What is needed in the art is technology to expedite the development of therapeutics that are specifically designed to treat the cause, and not the symptoms, of atopic asthma. These therapies represent the most likely way to avoid toxicity associated with nonspecific treatment. The therapies would selectively target a pathway, which is downstream from immune functions, such as IL-2 mediated T lymphocyte activation, that is necessary for the development of asthma and which would explain the episodic nature of the disorder and its close association with allergy. Nature demonstrates that a pathway is the appropriate target for asthma therapy when biologic variability normally exists in the pathway and individuals demonstrating the variability are not immunocompromised or illt except for their symptoms of atopic asthma.

Because of the difficulties related to the diagnosis and treatment of atopic allergies including asthma, the complex pathophysiology of these disorders is under intensive study. While these disorders are heterogeneous and may be difficult to define because they can take many forms, certain features are found in common among asthmatics. Examples of such features include abnormal skin test response to allergen challenge eosinophilia in the lung bronchial hyperresponsiveness (BHR), bronchodilator reversibility, and airflow obstruction.[3-10] These expressions of asthma related traits may be studied by quantitative or qualitative measures.

In many cases, elevated IgE levels are correlated with BHR, a heightened bronchoconstrictor response to a variety of stimuli.[4,6,8,9] BHR is believed to reflect the presence of airway inflammation," and is considered a risk factor for asthma.[11-12] BHR is accompanied by bronchial inflammation, including eosinophil infiltration into the lung and an allergic diathesis in asthmatic individuals.[6,8,13-18]

A number of studies document a heritable component to atopic asthma.[4,10] Family studies, however, have been difficult to interpret since these disorders are significantly influenced by age and gender, as well as many environmental factors such as allergens, viral infections, and pollutants.[19-21] Moreover, because there is no known biochemical defect associated with susceptibility to these disorders, the mutant genes and their abnormal gene products can only be recognized by the anomalous phenotypes they produce.

The functions of IL-9 and the IL-9 receptor (the IL-9 pathway) now extend well beyond those originally recognized. While the IL-9 pathway serves as a stimulator of T cell growth, this cytokine is also known to mediate the growth of erythroid progenitors, B cells, mast cells, and fetal thymocytes.[22,23] The IL-9 pathway acts synergistically with IL-3 in causing mast cell activation and proliferation.[24] The IL-9 pathway also potentiates the IL-4 induced production of IgE, IgG, and IgM by normal human B lymphocytes,[25] and the IL-4 induced release of IgE and IgG by murine B lymphocytes.[26] A role for the IL-9 pathway in the mucosal inflammatory response to parasitic infection has also been demonstrated.[27,28]

Nevertheless, it is not known how the sequence of the IL-9 receptor specifically correlates with atopic asthma and bronchial hyperresponsiveness. It is known that IL-9 binds to a specific receptor expressed on the surface of target cells.[23,29,30] The receptor actually consists of two protein 'chains: one protein chain, known as the IL-9 receptor, binds specifically with IL-9; the other protein chain is shared in common with the IL-2 receptor.[23] In addition, a cDNA encoding the human IL-9 receptor has been cloned and sequenced[23,29,30] This cDNA codes for a 522 amino acid protein which exhibits significant homology to the murine IL-9 receptor. The extracellular region of the receptor is highly conserved, with 67% homology existing between the murine and human proteins. The cytoplasmic region of the receptor is less highly conserved. The human cytoplasmic domain is much larger than the corresponding region of the murine receptor.[23]

The IL-9 receptor gene has also been characterized.[30] It is thought to exist as a single copy in the mouse genome and is composed of nine exons and eight introns.[30] The human genome contains at least four IL-9 receptor pseudogenes. The human IL-9 receptor gene has been mapped to the 320 kb subtelomeric region of the sex chromosomes X and Y.[23]

In spite of these studies, no variants of the IL-9 receptor gene have been discovered. There is, therefore, a specific need for genetic information on atopic allergy, asthma, bronchial hyperresponsiveness, and for elucidation of the role of IL-9 receptor in the etiology of these disorders. This information can be used to diagnose atopic allergy and related disorders using methods that identify genetic variants of this gene that are associated with these disorders. Furthermore, there is a need for methods utilizing the IL-9 receptor variants to develop therapeutics to treat these disorders.

SUMMARY OF THE INVENTION

Applicants have discovered natural variants of the human IL-9 receptor (also known as Asthma Associated Factor 2 or AAF2) and have linked these variants to the pathogenesis of asthma and related disorders. These discoveries have led to the development of diagnostic methods, and methods to discover pharmaceuticals for the treatment of therapeutics for atopic asthma. In addition, applicants have determined that the IL-9 receptor is critical to a number of antigen-induced responses in mice, including bronchial hyperresponsiveness, eosinophilia and elevated cell counts in bronchial lavage, and elevated serum total IgE. These findings typify atopic asthma and the associated allergic inflammation.

Furthermore, applicants have determined that a G to A nucleic acid variant occurs at position 1273 of the cDNA (SEQ ID NO: 2) which produces the predicted amino acid substitution of a histidine for an arginine at codon 344 of the human IL-9 receptor precursor protein. When the arginine residue occurs in both alleles in one individual, it is associated with less evidence of atopic asthma. Thus, applicants have identified the existence of a non-asthmatic phenotype characterized by arginine at codon 344 when it occurs in both IL-9 receptor gene products in one individual. As an additional significant corollary, applicants have identified the existence of susceptibility to an asthmatic, atopic phenotype characterized by a histidine at codon 344. Thus, the invention includes purified and isolated DNA molecules having such a sequence as well as the proteins encoded by such DNA.

Applicants have also determined that a splice variant of the IL-9R exists wherein the glutamine residue at position 173 of the IL-9R precursor protein has been deleted (SEQ ID NO: 3) (FIG. 5). Applicants have further shown that this variant is not able to transcribe a signal through the Jak-Stat pathway (FIG. 15) and is unable to induce cellular proliferation upon stimulation with 1L-9 (FIG. 16); therefore, individuals with this allele would be less susceptible to atopic asthma and related disorders.

Applicants have further determined that a variant of the IL-9R genomic DNA exists wherein nt-213, a thymine residue in intron 5 (213 nt upstream from exon 6), has been converted to a cytosine nucleotide. It is likely that such a variation can cause an increase in the frequency of the splice variant which removes the glutamine residue at the start of exon 6.

In addition, applicants have discovered a variant of IL-9R wherein exon 8 has been deleted (SEQ ID NO: 4) which results in a change in reading frame and a premature stop codon in exon 9. Such a variant would most likely be prevented from transmitting a signal through the Jak-Stat pathway and, therefore, individuals with this allele would also be less susceptible to atopic asthma and related disorders.

The biological activity of IL-9 results from its binding to the IL-9 receptor and the consequent propagation of a regulatory signal in specific cells; therefore, IL-9 functions can be interrupted by the interaction of IL-9 antagonists with IL-9 or its receptor. Down regulation, i.e., reduction of the functions controlled by IL-9, is achieved in a number of ways. Administering antagonists that can interrupt the binding of IL-9 to its receptor is one key mechanism, and such antagonists are within the claimed invention. Examples include administration of polypeptide products encoded by the DNA sequences of a naturally occurring soluble form of the IL-9 receptor, wherein the DNA sequences code for a polypeptide comprising exons 2 and 3 (SEQ ID NO: 5): Two other variations can produce soluble forms of the IL-9R receptor which comprise exons 2, 3 and 4 and In one case four amino acids from a different reading frame in exon 5 (SEQ ID NO: 6) (FIG. 6) and in the other case there are 27 amino acids from a different reading frame in exon 5 (SEQ ID NO: 7) (FIG. 7).

Methods to identify agonists and antagonists of the IL-9 receptor pathway can be identified by assessing receptor-ligand interactions which are well described in the literature. These methods can be adapted to high throughput automated assays that facilitate chemical screenings and potential therapeutic identification. Agonists are recognized by identifying a specific interaction with the IL-9 receptor. Loss of binding for a putative ligand which is labeled when a 100- to 1000-fold excess of unlabeled ligand is used is generally accepted as evidence of specific receptor binding. Many labels and detection schemes can be used during these experiments. A similar loss of binding when increasing concentrations of test compound are added to a known ligand and receptor is also evidence for an antagonist.

Knowledge of the variant receptors provides the means to construct expression vectors that can be used to make soluble receptor for receptor binding assays. Mutagenesis of these soluble receptors can be used to determine which amino acid residues are critical to bind ligand and aid in the structure-based design of antagonists. Cells lacking human IL-9 receptor can be transiently or stably transfected with expression vectors containing a variant receptor and used to assay for IL-9 pathway activity. These activities may be cellular proliferation, or prevention of apoptosis which have both been ascribed to the IL-9 pathway. These cells can be used to identify receptor agonists and antagonists as described above.

The methods discussed above represent various effective methods utilizing the variant forms of IL-9 receptor to develop therapeutics for atopic asthma and other related disorders.

A number of techniques have been described that may be used to diagnose atopic asthma that recognize single nucleotide variants in the IL-9 receptor including DNA sequencing, restriction fragment length polymorphisms (RFLPs), allele specific oligonucleotide analyses (ASO), ligation chain reaction (LCR), chemical cleavage, and single stranded conformational polymorphism analyses (SSCP). A skilled artisan will recognize that the use of one or more of these techniques, as well as others in the literature, may be used to detect one or more variations in the IL-9 receptor gene or mRNA transcript and are within the scope of the present invention.

Still other techniques may be used to detect amino acid variants in the IL-9 receptor including ELISAs, immunoprecipitations, Westerns, and immunoblotting. Thus, polyclonal and monoclonal antibodies which recognize specifically the structure of the various forms of the IL-9 receptor are also within the scope of this Invention and are useful diagnostic methods for describing susceptibility or resistance to atopic asthma and related disorders.

The methods discussed above represent various effective methods for diagnosing atopic asthma and other related disorders.

Thus, applicants have provided methods that use the IL-9 receptor to identify antagonists that are capable of regulating the interaction between IL-9 and its receptor. More specifically, applicants provide a method for assaying the functions of the IL-9 receptor to identify compounds or agents that may be administered in an amount sufficient to down-regulate either the expression or functions of the IL-9 pathway.

Having identified the role of the IL-9 pathway in atopic allergy, bronchial hyperresponsiveness and asthma, applicants also provide a method for the diagnosis of susceptibility and resistance to atopic allergy, asthma, and related disorders.

The accompanying figures, which are incorporated in and constitute a part of this specification, illustrate several embodiments of the invention and, together with the description, serve to explain the principle of the invention.

BRIEF DESCRIPTION OF THE DRAWINGS

FIG. 3: Translated cDNA sequence of the IL-9R precursor protein with the His allele at codon 344 (nucleotides 1272-1274) and the 9 Ser/4 Asn repeats starting at codon 410 (nucleotides 1470-1472). The corresponding peptide (SEQ ID NO: 28) is also shown.

FIG. 4: Translated cDNA sequence of IL-9R precursor protein with the deletion of exon 8 causing the frame shift in exon 9, the production of 11 non-wild type amino acids and a premature stop codon. The corresponding peptide (SEQ ID NO: 30) is also shown.

FIG. 5: Translated cDNA sequence of IL-9R precursor protein with the deletion of Glutamine at codon 173. The corresponding peptide (SEQ ID NO: 29) is also shown.

FIG. 6: Translated cDNA sequence of IL-9R precursor protein with an alternate splice in exon 5 resulting in a premature stop codon and the production of 27 non-wild type amino acids. The corresponding peptide (SEQ ID NO: 32) is also shown.

FIG. 7: Translated cDNA sequence of IL-9R precursor protein with an alternate splice in exon 5 resulting in a premature stop codon and the production of 4 non-wild type amino acids. The corresponding peptide (SEQ ID NO: 33) is also shown.

FIG. 8: Translated cDNA sequence of IL-9R precursor protein with the deletion of exon 4 producing a stop codon as the first codon of exon 5. The corresponding peptide (SEQ ID NO: 31) is also shown.

FIG. 9: Table showing the association between the IL-9 receptor genotype and atopic allergy. The Arg/Arg individuals are homozygous for the Arg allele with the 8 Ser/4 Asn repeats. The Arg/His individuals are heterozygous for the Arg allele with the 8 Ser/4 Asn repeats and the His allele with the 9 Ser/4 Asn repeats, 9 Ser/3Asn repeats, and 10 Ser/2 Asn repeats in exon 9. The His/His individuals are homozygous for the His allele with the 9 Ser/4 Asn repeats, 9 Ser/3 Asn repeats, and 10 Ser/2 Asn repeats in exon 9. The Arg/Arg individuals are protected from atopic allergy. The Arg/His and His/His individuals are susceptible to atopic allergy (P=0.002).

FIG. 11: Western blot of recombinant IL-9 receptor proteins (left: Arg allele with the 8 Ser/4 Asn repeats; right: His allele with the 9 Ser/4 Asn repeats) using C terminal antibody probe in TK transfected cell line.

Figure 13:
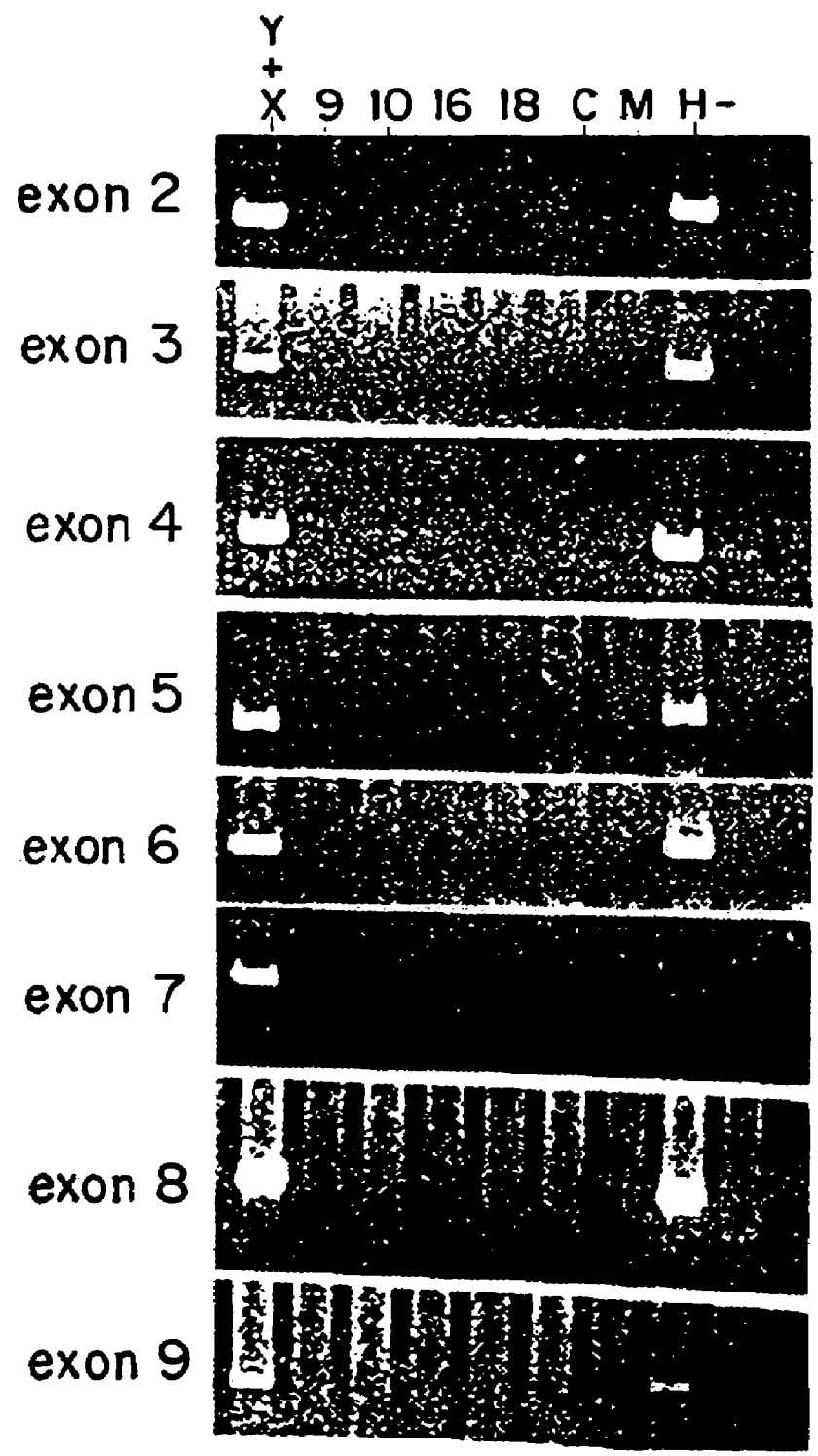
Figures 1, 14A:
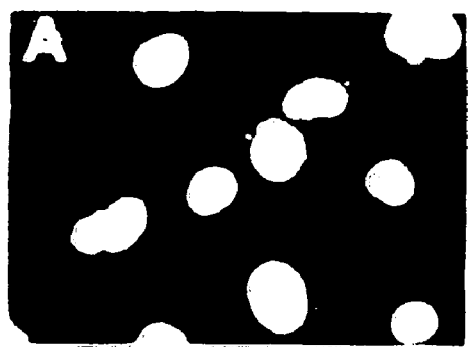
Figures 1, 14C:
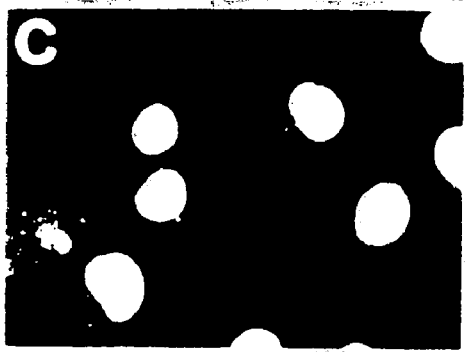
Figures 1, 14E:
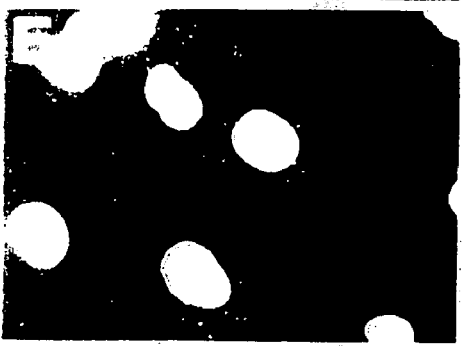
Figures 1, 14G:
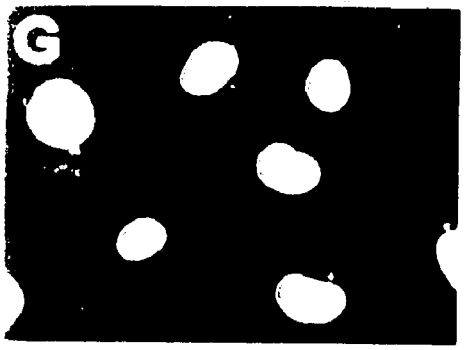
Figures 1, 14I:
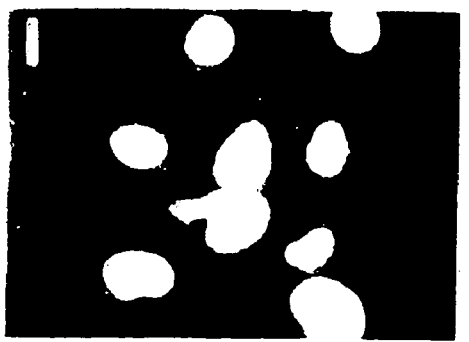
Figures 1, 14B:
Figures 1, 14D:
Figures 1, 14F:
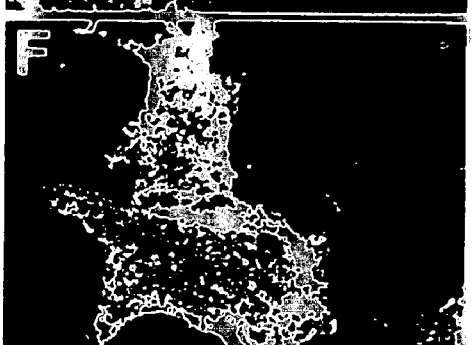
Figures 1, 14H:
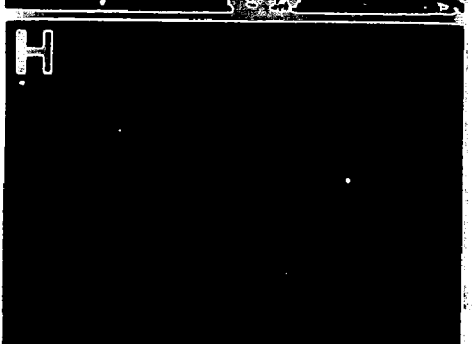
Figures 1, 14J:
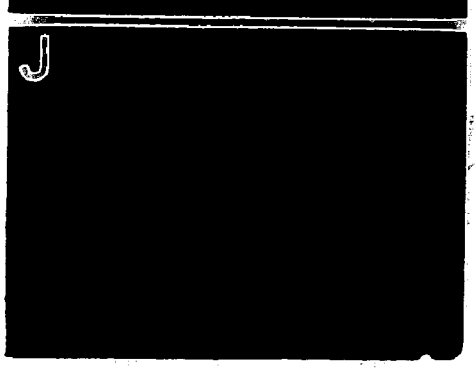
Figures 2, 14A:
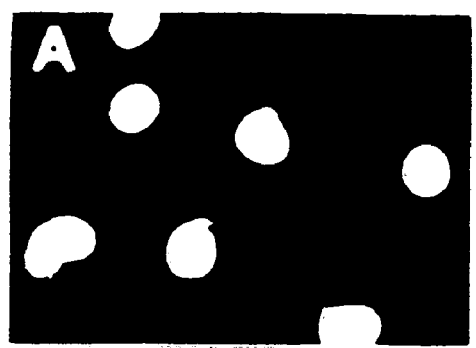
FIG. 2: Translated cDNA sequence of the wild type IL-9R precursor protein with Arg allele at codon 344 (nucleotides 1272-1274) and the 8 Ser/4 Asn repeats starting at codon 410 (nucleotides 1470-1472). The corresponding peptide (SEQ ID NO: 27) is also shown.
Figures 2, 14C:
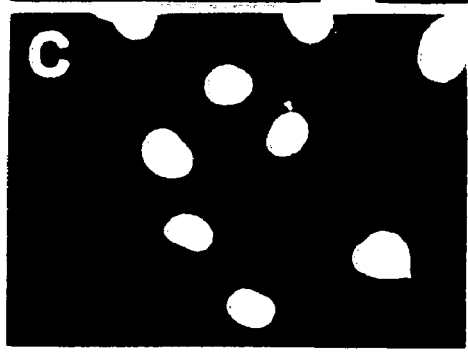
Figures 2, 14E:
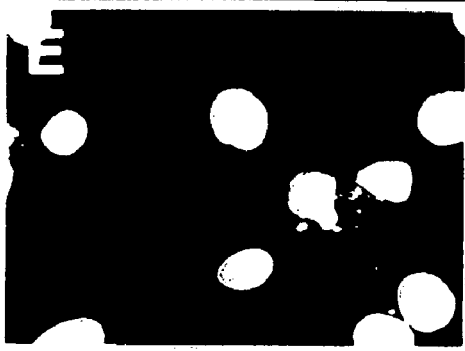
Figure 14G:
Figures 2, 14I:
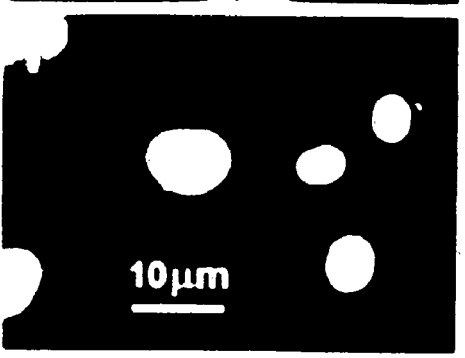
Figures 2, 14B:
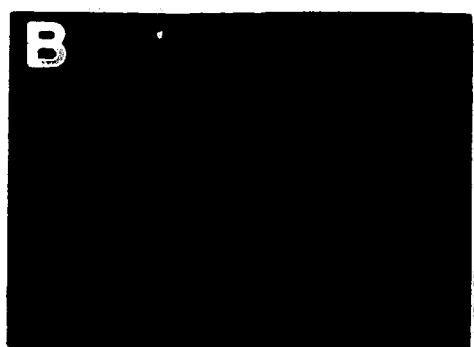
Figures 2, 14D:
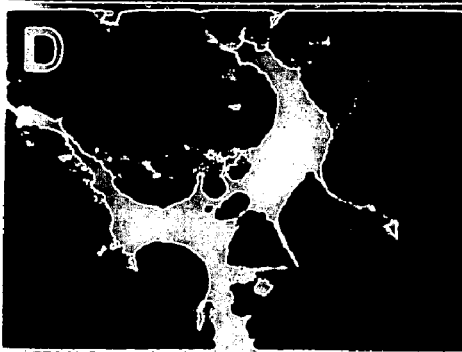
Figures 2, 14F:
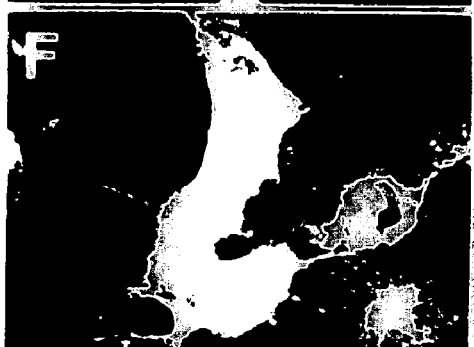
Figures 2, 14H:
Figures 2, 14J:
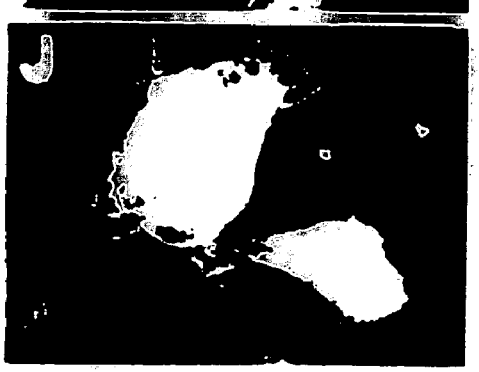
Figure 15A:
Figure 15B:
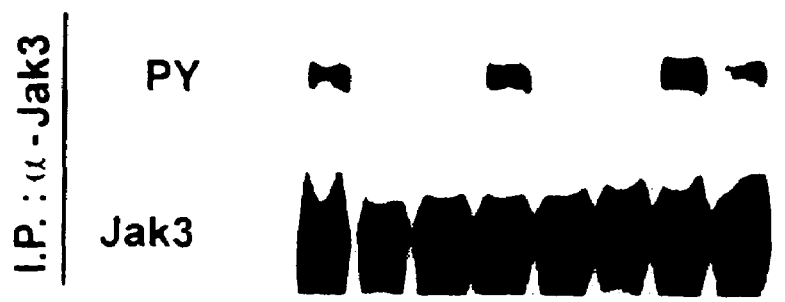
Figure 15C:
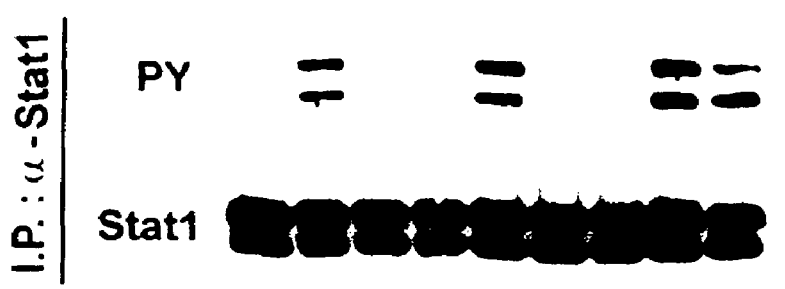
Figure 15D:
Figure 15E:
Figure 15F:
Figure 15G:
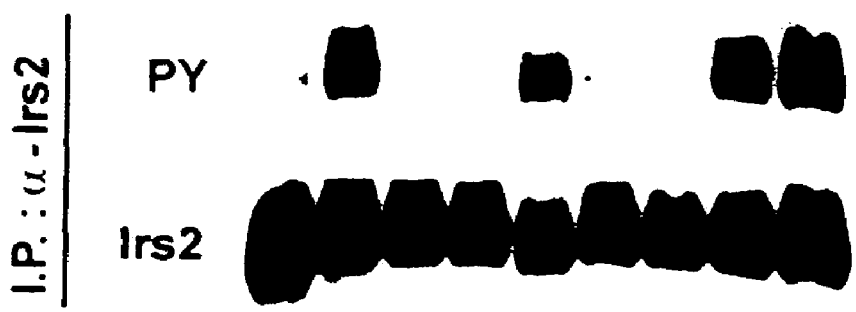

FIG. 13: XY specific amplimers for specific amplification of the IL-9 receptor gene. Pseudogenes on chromosomes 9, 10, 16, or 18 are not amplified by PCR. (M is mouse DNA, H is human DNA, and C is hamster DNA.)

FIG. 14: Immunoreactivity of an anti-human IL-9 receptor neutralizing antibody with wild type and Δ-Q receptors. Panel A): C0S7 cells were transiently transfected with the LXSN vector alone (A and B), wild type IL-9R (C and D), Wild type IL-9R with 9 Ser residues starting with codon 410 (E and F), Δ-Q 173 variant (G and H) and Δ-Q 173 with 9 Ser residues starting at codon 410 (I and J) and sequentially incubated with MAB290 and anti-mouse IgG Texas Red-conjugated antibody (B,D,F,H and J) as described (Example 8). DAPI staining (A,C,E,G and I) was included to visualize every cell in the photographed field. Panel B): as in A) except that cells were first fixed/permabilized and then incubated with a C-terminal specific antibody (sc698) followed by incubation with anti-rabbit IgG Texas Red-conjugated antibody. Bar=10 microns.

FIG. 15: Activation of members of Jak, Stat, and Irs families via different variants of the human IL-9 receptor. TS1 cells expressing either GH9, ΔQGR8, or ΔQGH9 were starved for 6 hours and then treated for 5 minutes without cytokine (-), with murine IL-9 (m), or with human IL-9 (h). Cell extracts were immunoprecipitated with various antibodies specific for different members of Jak, Stat and Irs families. Immunoblots were first reacted with an anti-phosphotyrosine antibody to detect only tyrosine-phosphorylated proteins and then stripped and reprobed with the same antibody used to immunoprecipitate each protein. GH9, ΔQGR8, ΔQGH9 are as indicated in FIG. 16.

Figure 16:
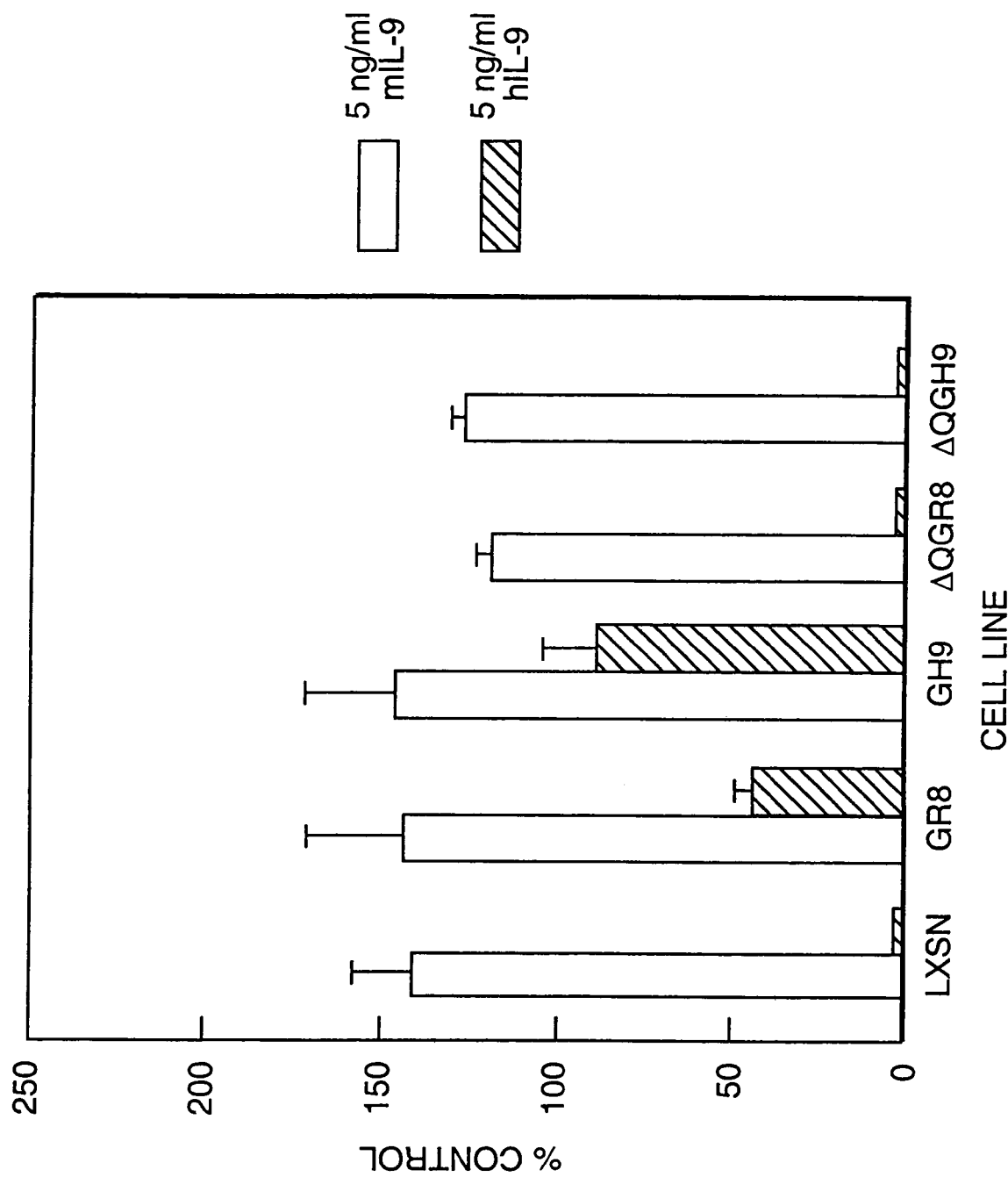

FIG. 16: Proliferation of TS1 cells expressing different forms of human IL-9 receptor. Cells were seeded in quadruplicate in 96-well plates (1000/well) and treated without cytokine or with murine or human IL-9 (5 ng/ml). A colorimetric assay was performed 7 days later to determine cell number, and the ratio between treated/untreated cells (% control) was calculated to assess growth rate. LxSN=cells transfected with the empty vector; GR8 is wild type IL-9R; GH9 is the His 344 variant with 9 Ser residues starting at codon 410; ΔQGR8 and ΔAQGH9 are the ΔQ173 variants on the wild type and the His 344+9—Ser background, respectively.

FIG. 17: Genomic DNA sequence of intron 5 of the IL-9R with a variation at nucleic acid 213 nt upstream from axon 6 where a T residue is changed to a C residue as indicated by the arrow.

DETAILED DESCRIPTION OF THE INVENTION

Applicants have resolved the needs in the art by elucidating an IL-9 pathway, and compositions that affect that pathway, which may be used in the treatment, diagnosis, and development of methods to' identify agents to prevent or treat atopic asthma and related disorders.

Asthma encompasses inflammatory disorders of the airways with reversible airflow obstruction. Atopic allergy refers to atopy, and related disorders including asthma, bronchial hyperresponsiveness (BHR), rhinitis, urticaria, allergic inflammatory disorders of the bowel, and various forms of eczema. Atopy is a hypersensitivity to environmental allergens expressed as the elevation of serum total IgE or abnormal skin test responses to allergens as compared to controls. BHR refers to bronchial hyperresponsiveness, a heightened bronchoconstrictor response to a variety of stimuli.

By analyzing the DNA of individuals that exhibit atopic allergy and asthma-related disorders, applicants have identified polymorphisms in the IL-9 receptor (IL-9R) gene that may correlate with the expression of asthma. The IL-9 receptor gene (also known as Asthma Associated Factor 2 or AAF2) refers to the genetic locus of interleukin-9 receptor, a cytokine receptor associated with a variety of functions involving the regulation of human myeloid and lymphoid systems. The human IL-9 receptor gene of the present invention is found in the subtelomeric region of the XY chromosomes.

By polymorphism, applicants mean a change in a specific DNA sequence, termed a "locus," from the prevailing sequence. In general, a locus is defined as polymorphic when artisans have identified two or more alleles encompassing that locus and the least common allele exists at a frequency of 1% or more.

Specific amplification of the authentic IL-9R (gene encoding for the biologically functional protein located in the XYq pseudoautosomal region) using standard primer design was not possible because IL-9R has four highly homologous (>90% nucleotide identity), non-processed pseudogenes at other loci in the human genome (chromosome 9, 10, 16, 18). Because of the high identity of these other genes, genomic PCR amplification using standard primer design resulted in co-amplification of all genes, thus making sequence analysis of the authentic gene equivocal. In order to study authentic IL-9R structure as it may relate to predisposition to disease such as asthma, discussed in this application, or other diseases such as cancer (Renauld, et al., *Oncogene*, 9:1327-1332, 1994; Gruss, et al., *Cancer Res.*, 52:1026-1031, 1992); applicants have designed specific amplimers. The specific primers were found to be authentic for IL-9R amplification with no amplification of the 4 pseudogenes. The primer sequences are shown in Example 2 and their specificity is demonstrated in FIG. 13.

Figure 1:
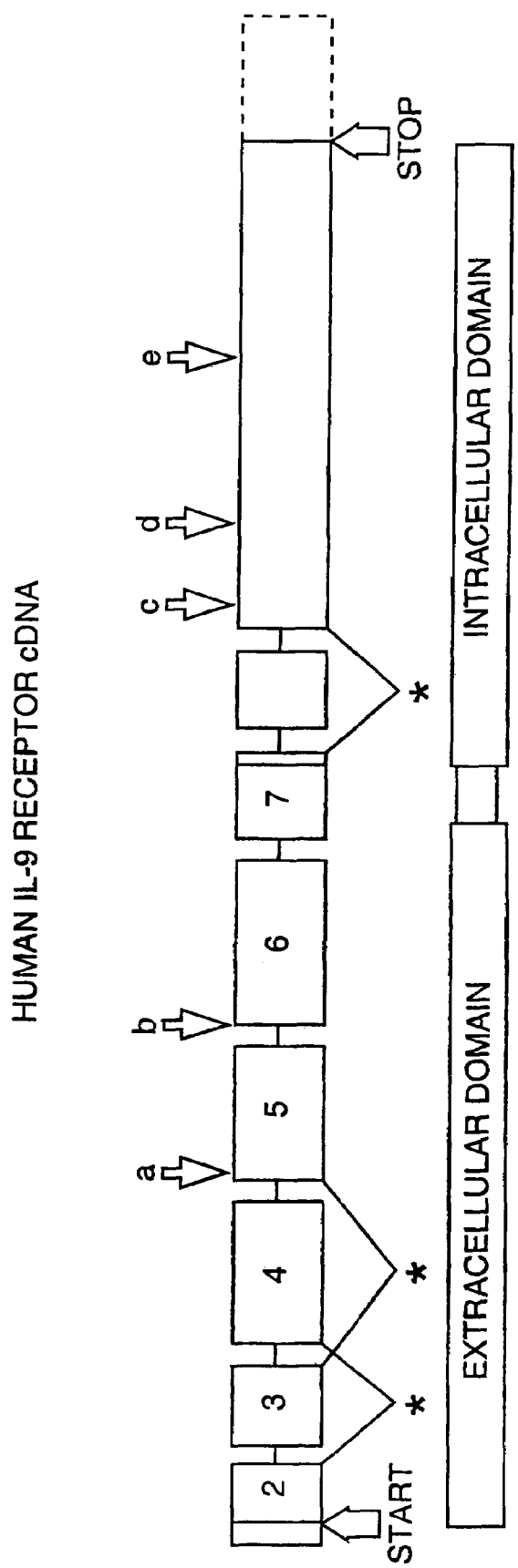
FIG. 1: Schematic representation of the human IL receptor cDNA. Boxes depict axon 2 to 9 encompassing the coding region (relative size in scale, except the 3' untranslated part of exon 9, outlined by dashed line). Transmembrane region is encoded by exon 7, intracellular domain by exon 8 and 9, and the extracellular by exon 2 to 6. Arrows indicate polymorphisms or aberrant splices affecting partial sequence of the exon; a) deletion of the first 5 or 29 nucleotides in axon 5; b) deletion of the first 3 nucleotides in exon 6 (codon 173); c) arg/gly polymorphism at codon 310; d) arg/his polymorphism at codon 344; e) polymorphism at codon 410+n consisting of either 8 or 9 serines;*) complete deletion of exon 3, 4 or 8.

Applicants have also amplified, by RT-PCR, the entire coding region of the IL-9 receptor cDNA using RNA extracted from PBMCs (peripheral blood mononuclear cells) purified from 50 donors. FIG. 1 illustrates the most frequent variations found in 50 Individuals analyzed. Exon 3, 4, 5, 6 and 8 were affected by aberrant splicing events in samples where full-length cDNAs could also be cloned. Some transcripts showed complete deletion of exon 3, which causes a frameshift creating a stop codon after a stretch of 79 unrelated residues. In the case of deletion of exon 4, a frameshift is also generated and the first codon in exon 5 is converted to a stop codon. In some other cDNAs, exon 5 presented partial deletion of the first 5 or 29 nucleotides, both deletions leading to frameshifts resulting in early stop codons within exon 5. Hence, in all instances, the putative truncated protein would lack most of the extracellular domain as well as all the transmembrane and cytoplasmic domains. If secreted, these forms might function as soluble receptors. Finally, the first three nucleotides of exon 6, corresponding to codon 173, were frequently found spliced out, resulting in deletion of the glutamine at this codon with no other changes in the remaining protein sequence. This splice variant is possibly related to a variant found in intron 5 of the genomic DNA (SEQ ID NO: 24) which would increase the frequency of the splice variant (FIG. 17 and Example 12).

Applicants have also found allelic variations limited to the coding sequence of exon 9. Polymorphisms involving codon 310 and 410 have been previously disclosed.[29,30] (Kermouni, A., et al., *Genomics*, 371-382 (1995)). Codon 310 encodes for either arginine or glycine, depending on whether the first nucleotide at that codon is an adenine or a guanidine, respectively. At codon 410 (from hereon termed "410+n") begins a stretch of either 8 or 9 AGC trinucleotides repeats which would be translated in 8 or 9 serines, respectively.

Applicants have found a new polymorphism at codon 344. Here, the second nucleotide is either adenine or guanidine, the two possible residues encoded by this codon being histidine or arginine, respectively. Moreover, a correspondence between codon 344 and 410+n was observed wherein arginine at codon 344 is consistently found with 8 serines at codon 410+n and histidine at codon 344 is found with 9 serines. The human IL-9 receptor cDNA originally cloned from a human megakaryobiastic leukemic cell line, Mole, presented 9 serines at codon 410+n and, unlike applicants' clones, an arginine at codon 344.[29] Another megakaryoblastic leukemic cell line UT-7 has been reported to carry the same arginine/9-serines allele.[30] Applicants cloned 18 cDNAs from Mole cell tine and found that 6 had 8 serines at codon 410+n and arginine at codon 344. The remaining ten clones presented the published sequence. Applicants also genotyped the human acute myelogenous leukemia cell line KG-1 and found that it was histidine/9-serines homozygous.

These DNA molecules and corresponding RNA are isolated using techniques that are standard in the art, such as Sambrook, et al., *Molecular Cloning: A Laboratory Manual*, 2d ed., Cold Spring Harbor Laboratory Press (1985). By isolated, applicants mean that the DNA is free of at least some of the contaminants associated with the nucleic acid or polypeptides occurring in a natural environment.

The invention also includes the proteins encoded by these nucleic acid sequences. The invention further includes fragments of the molecules. By fragments, applicants mean portions of the nucleic acid sequence that maintain the function of the full sequence. As would be known in the art, fragments result from deletions, additions, substitutions and/ or modifications.

The source of the IL-9 receptor variants of the invention is human. Alternatively, the DNA or fragment thereof may be synthesized using methods known in the art. It is also possible to produce the compound by genetic engineering techniques, by constructing DNA by any accepted technique, cloning the DNA in an expression vehicle and transfecting the vehicle into a cell which will express the compound. See, for example, the methods set forth in Sambrook, et al., *Molecular Cloning: A Laboratory Manual*, 2d ed., Cold Spring Harbor Laboratory Press (1985).

The demonstration of variant IL-9 receptor sequences which may be associated with atopic allergy and an asthma-like phenotype, and others which may be associated with the lack of an asthma-like phenotype, provides methods of diagnosing susceptibility to atopic asthma and related disorders. Certain variants can produce soluble receptors which can be used for treating these disorders.

A receptor is a soluble or membrane-bound component that recognizes and binds to molecules, and the IL-9 receptor of the invention is the component that recognizes and binds to IL-9. The functions of the IL-9 receptor consist of binding to IL-9 or an IL-9-like molecule and propagating its regulatory signal in specific cells.[29,30,34,35] Human IL-9 has been shown to cause phosphorylation of the IL-9 receptor itself and the activation of proteins of the Jak-Stat pathway, Jak1, Stat1, Stat3, Stat5, and Irs2, upon binding the human IL-9 receptor (Demoulin, J-B., et al., *Molecular and Cellular Biology*, p. 4710-4716, September 1996). Applicants have examined whether IL-9R or its variants showed any bias in the activation of these proteins and extended the analysis to Jak3 and Irs1, It was determined that all of the proteins of the pathway including Jak3 and Irs1 were phophoralated by IL-9R activation. It was also determined that IL-9R variants with changes at codons 310, 344 and 410+n provided the same up-regulation as wild type IL-91R. Therefore, one aspect of the invention is therapeutics for the treatment of atopic asthma which inhibit interactions in the Jak-Stat pathway.

Unlike the wild type receptor and the other tested variants, the ΔQ173 variant could not activate any proteins in the Jak-Stet pathway (FIG. 15). In addition, the ΔQ173 variant could not support cellular proliferation upon IL-9 stimulation (FIG. 16). Therefore, individuals who express the ΔQ173 variant are less likely to be susceptible to atopic asthma and related disorders. One aspect of the Invention, therefore, is therapeutics that increase the expression of the ΔQ173 splice variant for the treatment of atopic asthma and related disorders.

One diagnostic embodiment involves the recognition of variations in the DNA sequence of the IL-9 receptor gene or transcript. One method involves the use of a nucleic acid molecule (also known as a probe) having a sequence complementary to the IL-9 receptors of the invention under sufficient hybridizing conditions, as would be understood by those in the art. In one embodiment, the nucleic acid molecule will bind specifically to the codon for Arg344 of the mature IL-9 receptor protein, or to His344, and in another embodiment will bind to both Arg344 and to His344. In yet another embodiment, it will bind to the codon for Gin 173. These methods may also be used to recognize other variants of the IL-9 receptor. Another method of recognizing DNA sequence variation associated with these disorders is direct DNA sequence analysis by multiple methods well known in the art.[44] Another embodiment involves the detection of DNA sequence variation in the IL-9 receptor gene associated with these disorders.[40-44] These include the polymerase chain reaction, restriction fragment length polymorphism (RFLP) analysis, and single-stranded conformational analysis. In a preferred embodiment, applicants provide specifically for a method to recognize, on a genetic level, the polymorphism in IL-9 receptor associated with the His344 and Arg344 alleles using an ASO PCR. In other embodiments, the ligation chain reaction can be used to distinguish these alleles of IL-9 receptor genes. The present invention also includes methods for the Identification of antagonists of IL-9 and its receptor. Antagonists are compounds that are themselves devoid of pharmacological activity, but cause effects by preventing the action of an agonist. To identify an antagonist of the invention, one may test for competitive binding with a known agonist or for down-regulation of IL-9-like functions as described herein and in the cited literature.[2,22-35]

Specific assays may be used to screen for pharmaceuticals useful in treating atopic allergy based on IL-9 receptor's known role on the proliferation of T lymphocytes, IgE synthesis and release from mast cells.[29,30,33-35] Another assay involves the ability of human IL-9 receptor to specifically induce the rapid and transient tyrosine phosphorylation of multiple proteins in Mole cells.[34] Because this response is dependent upon the expression and activation of the IL-9 receptor, it represents a simple method or assay for the characterization of potentially valuable compounds. The tyrosine phosphorylation of Stat3 transcriptional factor appears to be specifically related to the functions of the IL-9 receptor,[35] and this response represents a simple method or assay for the characterization of compounds within the invention. Still another method to characterize the function of the IL-9 receptor involves the use of the well known murine TS1 clone transfected with a human receptor which can be used to assess human IL-9 function with a cellular proliferation assay.[29] These methods can be used to identify antagonists of the IL-9, receptor.

In a further embodiment, the invention includes the down-regulation of IL-9; expression or function by administering soluble IL-9 receptor molecules that bind IL-9. Applicants and Renauld, et al.[29] have shown the existence of a soluble form of the IL-9 receptor. This molecule can be used to prevent the binding of IL-9 to cell-bound receptor and act as an antagonist of IL-9. Soluble receptors have been used to bind cytokines or other ligands to regulate their function.[45] A soluble receptor is a form of a membrane-bound receptor that occurs in solution, or outside of the membrane. Soluble receptors may occur because the segment of the molecule which commonly associates with the membrane is absent. This segment is commonly referred to in the art as the transmembrane domain of the gene, or membrane-binding segment of the protein. Thus, in one embodiment of the invention, a soluble receptor may represent a fragment or an analog of a membrane-bound receptor.

Applicants have identified three splice variants of the human IL-9 receptor that result in the production of proteins that could act as soluble receptors. One splice variant resulted in the deletion of axon 4 which introduced a frame-shift resulting in a stop codon as the first codon of exon 5. This variant would produce a peptide of about 45 residues that contains an epitope reactive with antibodies that block the IL-9/IL-9R interaction. The other two variants contain deletions in exon 5 that will produce premature stop codons early in the axon, but, in these cases, without the deletion of exon 4. These variants would produce a protein of about 100 residues also containing the epitope recognized by blocking antibody.

Soluble IL-9 receptors may be used to screen for potential therapeutics, including antagonist useful in treating atopic asthma and related disorders. For example, screening for peptides and single-chain antibodies using phage display could be facilitated using a soluble receptor. Phage that bind to the soluble receptor can be isolated and the molecule identified by affinity capture of the receptor and bound phage. In addition, compound screenings for agents useful in treating atopic asthma and related disorders can incorporate a soluble receptor and ligand that bind in the absence of an antagonist. Detection of the ligand and receptor interaction occurs because of the proximity of these molecules. Antagonists are recognized by inhibiting these interactions.

In addition, the invention includes pharmaceutical compositions comprising the compounds of the invention together with a pharmaceutically acceptable carrier.

Pharmaceutically acceptable carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectionable solutions. Suitable pharmaceutical carriers are described in Martin, E. W., *Remington's Pharmaceutical Science*, specifically incorporated herein by reference.

The compounds used in the method of treatment of this invention may be administered systemically or topically, depending on such considerations as the condition to be treated, need for site-specific treatment, quantity of drug to be administered, and similar considerations.

Topical administration may be used. Any common topical formation such as a solution, suspension, gel, ointment, or salve and the like may be employed.

Preparation of such topical formulations are well described in the art of Pharmaceutical formulations as exemplified, for example, by *Remington's Pharmaceutical Science* Edition 17, Mack Publishing Company, Easton, Pa. For topical application, these compounds could also be administered as a powder or spray, particularly in aerosol form. In a preferred embodiment, the compounds of this invention may be administered by inhalation. For inhalation therapy, the compound may be in a solution useful for administration by metered dose inhalers, or in a form suitable for a dry powder inhaler.

The active ingredient may be administered in pharmaceutical compositions adapted for systemic administration. As is known, if a drug is to be administered systemically, it may be confected as a powder, pill, tablet or the like, or as a syrup or elixir for oral administration. For intravenous, intraperitoneal or intralesional administration, the compound will be prepared as a solution or suspension capable of being administered by injection. In certain cases, it may be useful to formulate these compounds in suppository form or as an extended release formulation for deposit under the skin or intermuscular injection.

An effective amount is that amount which will down-regulate the functions controlled by IL-9 receptor. A given effective amount will vary from condition to condition and in certain instances may vary with the severity of the condition being treated and the patient's susceptibility to treatment. Accordingly, a given effective amount will be best determined at the time and place through routine experimentation. It is anticipated, however, that in the treatment of asthma and related disorders in accordance with the present invention, a formulation containing between 0.001 and 5 percent by weight, preferably about 0.01 to 1%, will usually constitute a therapeutically effective amount. When administered systemically, an amount between 0.01 and 100 mg per kg body weight per day, but preferably about 0.1 to 10 mg/kg, will affect a therapeutic result in most instances.

Applicants also provide for a method to screen for the compounds that down-regulate the functions controlled by the IL-9 receptor. One may determine whether e functions expressed by IL-9 receptor are down-regulated using techniques standard in the art.[29,30,34,35] In a specific embodiment, applicants provide for a method of identifying compounds with functions comparable to IL-9. In one embodiment, the functions of IL-9 receptor may be assessed in vitro. As is known to lose in the art, human IL-9 receptor activation specifically induces the rapid and transient tyrosine phosphorylation of multiple proteins in cells responsive to IL-9. The tyrosine phosphorylation of Stat3 transcriptional factor appears to be specifically elated to the actions of the IL-9 pathway. Another method to characterize the unction of IL-9 and IL-9-like molecules depends on the "stable expression" of the IL-9 receptors in murine TS1 clones or TF1 clones, which do not normally express human receptor. These transfectants can be used to assess human IL-9 receptor function with a cellular proliferation assay.[29]

The invention also includes a simple screening assay for saturable and specific ligand binding based on cell lines that express the IL-9 receptor variants.[23,29] The IL-9 receptor is expressed in a wide variety of cell types, including K562, C616645, KG-1 transfected with the human IL-9 receptors, B cells, T cells, mast cells, HL60, HL60-clone 5, TS1 transfected with the human IL-9 receptors, 32D transfected with the human IL-9 receptors, neutrophils, megakaryocytes (UT-7 cells),[30] the human megakaryoblastic leukemia cell line Mo7e[34], TF1,[29] macrophages, eosinophiles, fetal thymocytes, the human kidney cell line 293,[30] and murine 320 and embryonic hippocampal progenitor cell lines.[23,29,30]

The practice of the present invention will employ the conventional terms and techniques of molecular biology, pharmacology, immunology, and biochemistry that are within the ordinary skill of those in the art. See, for example, Sambrook, et al., *Molecular Cloning: A Laboratory Manual*, 2d ed., Cold Spring Harbor Laboratory Press, or Ausubel, et al., *Current Protocols in Molecular Biology*, John Wiley & Sons, Inc.

Nonetheless, we offer the following basic background information. The body's genetic material, or DNA, is arranged on 46 chromosomes, which each comprises two arms joined by a centromere. Each chromosome is divided into segments designated p or q. The symbol p is used to identify the short arm of a chromosome, as measured from the centromere to the nearest telomere. The long arm of a chromosome is designated by the symbol q. Location on a chromosome is provided by the chromosome's number (i.e., chromosome 5) as well as the coordinates of the p or q region (i.e., q31-q33). In addition, the body bears the sex chromosomes, X and Y. During meiosis, the X and Y chromosomes exchange DNA sequence information in areas known as the pseudoautosomal regions.

DNA, deoxyribonucleic acid, consists of two complementary strands of nucleotides, which include the four different base compounds, adenine (A), thymine (T), cytosine (C), and guanine (G). A of one strand bonds with T of the other strand while C of one strand bonds to G of the other to form complementary "base pairs," each pair having one base in each strand. A sequential grouping of three nucleotides (a "codon") codes for one amino acid. Thus, for example, the three nucleotides CAG code for the amino acid Glutamine. The 20 naturally occurring amino acids, and their one-letter codes, are as follows:

| Alanine | Ala | A |
| Arginine | Arg | R |
| Asparagine | Asn | N |
| Aspartic Acid | Asp | D |
| Asparagine or Aspartic acid | Asx | B |
| Cysteine | Cys | C |
| Glutamine | Gin | Q |
| Glutamine Acid | Glu | E |
| Glutamine or Glutamic acid | Glx | Z |
| Glycins | Gly | G |
| Histidine | His | H |
| Isoleucine | Ile | I |
| Leucine | Leu | L |

-continued

| Lysine | Lys | K |
| Methionine | Met | M |
| Phenylalanine | Phe | F |
| Proline | Pro | P |
| Serine | Ser | S |
| Threonin | Thr | T |
| Tryptopan | Trp | W |
| Tyrosine | Tyr | Y |
| Valine | Val | V |

Amino acids comprise proteins. Amino acids may be hydrophilic, i.e., displaying an affinity for water, or hydrophobic, i.e., having an aversion to water. Thus, the amino acids designated as G, A, V, L, I, P, F, Y, W, C and M are hydrophobic and the amino acids designated as S, Q, K. R, H, D, E, N and T are hydrophilic. In general, the hydrophilic or hydrophobic nature of amino acids affects the folding of a peptide chain and, consequently, the three-dimensional structure of a protein.

DNA is related to protein as follows:

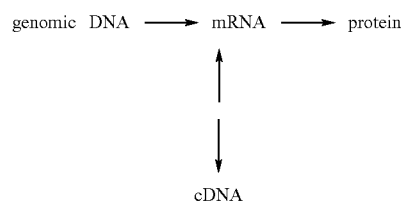

Genomic DNA comprises all the DNA sequences found in an organism's cell. It is "transcribed" into messenger RNA ("mRNA"). Complementary DNA ("cDNA") is a complementary copy of mRNA made by reverse transcription of mRNA. Unlike genomic DNA, both mRNA and cDNA contain only the protein-encoding or polypeptide-encoding regions of the DNA, the so-called "exons." Genomic DNA may also include "introns," which do not encode proteins.

In fact, eukaryotic genes are discontinuous with proteins encoded by them, consisting of exons interrupted by Introns. After transcription into RNA, the introns are removed by splicing to generate the mature messenger RNA (mRNA). The splice points between exons are typically determined by consensus sequences that act as signals for the splicing process. Splicing consists of a deletion of the intron from the primary RNA transcript and a joining or fusion of the ends of the remaining RNA on either side of the excised intron. Presence or absence of introns, the composition of introns, and number of introns per gene, may vary among strains of the same species, and among species having the same basic functional gene. Although, in most cases, introns are assumed to be nonessential and benign, their categorization is not absolute. For example, an intron of one gene can represent an axon of another. In some cases, alternate or different patterns of splicing can generate different proteins from the same single stretch of DNA. In fact, structural features of introns and the underlying splicing mechanisms form the basis for classification of different kinds of introns.

As to the exons, these can correspond to discrete domains or motifs as, for example, functional domains, folding regions, or structural elements of a protein; or to short polypeptide sequences, such as reverse turns, loops, glycosylation signals and other signal sequences, or unstructured polypeptide linker regions. The axon modules of the present combinatorial method can comprise nucleic acid sequences corresponding to naturally occurring axon sequences or naturally occurring axon sequences which have been mutated (e.g., point mutations, truncations, fusions).

Returning now to the manipulation of DNA, DNA can be cut, spliced, and otherwise manipulated using "restriction enzymes" that cut DNA at certain known sites and DNA ligases that join DNA. Such techniques are well known to those of ordinary skill in the art, as set forth in texts such as Sambrook, et al., *Molecular Cloning: A Laboratory Manual*, 2d ed.; Cold Spring Harbor Laboratory Press (1985) or Ausubel, et al., *Current Protocols in Molecular Biology*, John Wiley & Sons, Inc. (1994).

DNA of a specific size and sequence can then be inserted into a "replicon," which is any genetic element, such as a plasmid, cosmid, or virus, that is capable of replication under its own control. A "recombinant vector" or "expression vector" is a replicon into which a DNA segment is inserted so as to allow for expression of the DNA; i.e., production of the protein encoded by the DNA. Expression vectors may be constructed in the laboratory, obtained from other laboratories, or purchased from commercial sources.

The recombinant vector (known by various terms in the art) may be introduced into a host by a process generically known as "transformation:" Transformation means the transfer of an exogenous DNA segment by any of a number of methods, including infection, direct uptake, transduction, F-mating, microinjection, or electroporation into a host cell.

Unicellular host cells, known variously as recombinant host cells, cells, and cell culture, include bacteria, yeast, insect cells, plant cells, mammalian cells and human cells. In particularly preferred embodiments, the host cells include *E. coli, Pseudomonas, Bacillus, Streptomyces*, Yeast, CHO, R1-1, B-W, LH, COS-J, COS-7, BSC1, BSC40, BMT10, and S69 cells. Yeast cells especially include *Saccharorhyces, Pichia, Candida, Hansenula*, and *Torulopsis*.

As those skilled in the art recognize, the expression of the DNA segment by the host cell requires the appropriate regulatory sequences or elements. The regulatory sequences vary according to the host cell employed, but include, for example, in prokaryotes, a promoter, ribosomal binding site, and/or a transcription termination site. In eukaryotes, such regulatory sequences include a promoter and/or a transcription termination site. As those in the art well recognize, expression of the polypeptide may be enhanced, i.e., increased over the standard levels, by careful selection and placement of these regulatory sequences.

In other embodiments, promoters that may be used include the human cytomegalovirus (CMV) promoter, tetracycline-inducible promoter, simian virus (SV40) promoter, moloney murine leukemia virus long terminal repeat (LTR) promoter, glucocorticoid inducible murine mammary tumor virus (MMTV) promoter, herpes thymidine kinase promoter, murine and human-actin promoters, HTLV1 and HIV IL-9 5' flanking region, human and mouse IL-9 receptor 5' flanking region, bacterial tac promoter and *Drosophila* heat shock protein scaffold attachment region (SAR) enhancer elements.

The DNA may be expressed as a polypeptide of any length such as peptides, oligopeptides, and proteins. Polypeptides also include translational modifications such as glycosylations, acetylabons, phosphorylations, and the like.

Another molecular biologic technique of interest to the present invention is "linkage analysis." Linkage analysis is an analytic method used to identify the chromosome or chromosomal region that correlates with a trait or disorder.[47] Chromosomes are the basic units of inheritance on which genes are organized. In addition to genes, artisans have identified "DNA markers" on chromosomes. DNA markers are known sequences of DNA whose identity and sequence can be readily determined. Linkage analysis methodology has been applied to the mapping of disease genes, for example, genes relating to susceptibility to asthma, to specific chromosomes.[47,48]

Applicants wish to incorporate by reference all the references set forth above and below.

Other embodiments of the invention will be apparent to those skilled in the art from consideration of the specification and practice of the invention disclosed. It is intended that the specification and examples be considered exemplary only with a true scope of the invention being indicated by the claims.

Having provided this background information, applicants now describe preferred aspects of the invention.

EXAMPLE 1

Identification of IL-9 Receptor Transcript Polymorphisms

A population of 52 individuals was ascertained randomly with respect to asthma and atopy from the Philadelphia, Pa., area. Total serum IgE were assayed by enzyme-linked immunosorbent assay (ELISA, Genzyme, Cambridge, Mass.).

To assess the structural forms of the human IL-9 receptor cDNA, PBMCs from these 52 unrelated donors were isolated and cultured in the presence of PHA and PMA (described in Example 4). Previous data from applicants' laboratory demonstrated the kinetics of expression for IL-9 receptor message in primary cultures peak at day 6 after mitogen stimulation. Applicants cultured the cells, therefore, for 6 days at which time the cells were harvested and their RNA and DNA were isolated as described in Example 5.

RNAs were reverse transcribed and amplified by PCR using primers specific for full-length IL-9 receptor cDNA as described in Example 5. Amplification products from each individual were cloned into the TA PCR cloning vector and ten clones containing the expected inserts (as determined by digestion and gel electrophoresis) were sequenced in their entirety and analyzed for structural or sequence variation.

Seven major variants were identified from the above screen. These cDNAs represent a codon 173 deletion, an exon 4 deletion, two separate deletions in exon 5, an axon 8 deletion, and a full-length cDNA containing an ARG-to-HIS change at codon 344 of the mature protein. Additional variants exist on each of these genetic backgrounds. The Arg allele is associated with 8 Ser/4 Asn repeats and 7 Ser/4 Asn repeats; the His allele is associated with 9 Ser/4 Asn repeats, 9 Ser/3 Asn repeats, and 10 Ser/2 Asn. All of these variants are depicted in FIG. 1.

Variants were cloned into the eukaryotic expression vector pCEP4 (Ciontech) which contains a CMV promoter that drives the expression of the cloned cDNA followed by an SV40 polyadenylation signal. The vector also contains a hygromycin B resistance gene which is used for selection of eukaryotic cells containing the vector and presumably expressing the cloned cDNA under control of the CMV promoter. Recombinant plasmids were analyzed by sequence and those plasmids containing the correct cDNA inserts were transfected into eukaryotic recipient cells such as the Syrian hamster fibroblast TK-ts13, the human glioblastoma T98G, the human myeloid leukemia line TF-1 and the murine myeloid precursor cell line 32D as described in Example 3. Function was biologically assessed as a response to the IL-9 ligand in growth and/or apoptosis (Examples 7 and 10).

Figure 12:
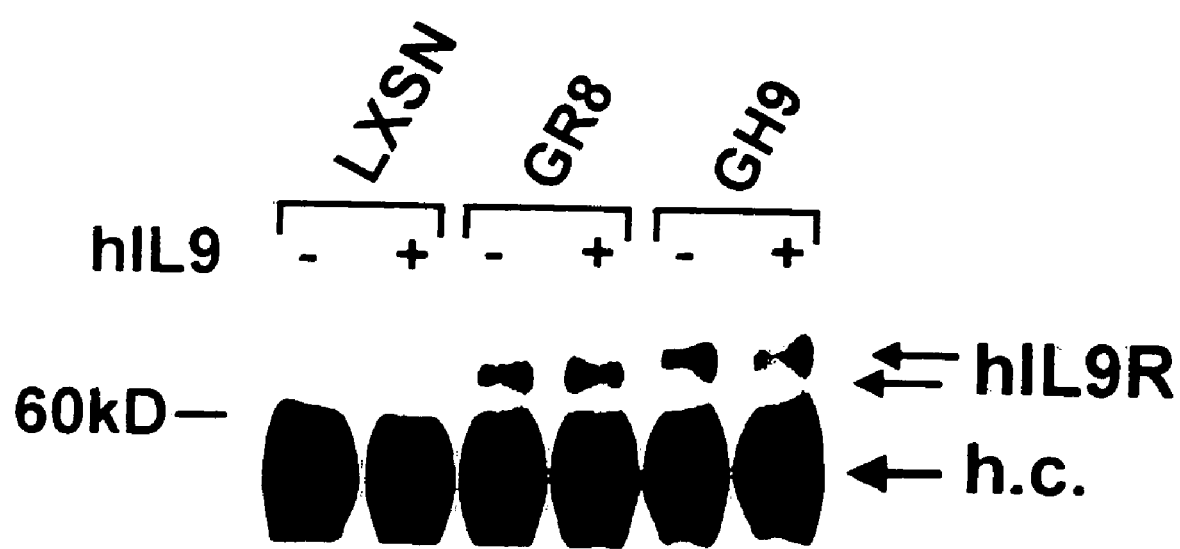
FIG. 12: Expression of human IL-9 receptor variants in TS1 cells showing differential mobility between the Arg 344 variant with 8 Ser/4 Asn repeats (GM) and His 344 variant with 9 ser/4 Asn repeats (GH9). A mobility shift is seen demonstrating differential post-translational modification of these two variant form of the IL-9 receptor.

Experiments in which the full-length IL-9 receptor cDNAs containing the ARG or HIS variants were performed are the TK-ts13 hamster fibroblasts or the human T98G glioblastoma cells. Cells were transfected and analyzed 48 hours later by Western blot and in situ staining using human specific carboxy terminal antibodies (Santa Cruz) (Example B). In situ analysis demonstrated that both forms of receptor appeared to be expressed in both the hamster and human lines (FIGS. 11 and 12). Interestingly, while Western blots of both forms appeared to be expressed at equal levels in both the human and hamster lines, a differential migration pattern appeared between the ARG and HIS receptor forms in the TS1 cell line (FIG. 12) which suggests a differential post-translational modification such as glycosylation, phosphorylation, etc. This biochemical difference may be the mechanism by which the altered function results in altered phenotype. The frequency of the various substitutions were used as an unbiased estimate of the prevalence of each variant in the general population. Genotype was compared to phenotype assessed by questionnaire. A diagnosis of allergy and asthma was determined by a physician reviewing the questionnaires. Individuals homozygous for the Arg344 alleles were significantly less likely to demonstrate evidence for allergy and asthma when compared to heterozygotes or homozygous His344 (FIG. 9).

EXAMPLE 2

Genomic—Analysis of the IL-9 Receptor Genes.

In order to perform genomic analyses of allergic and/or asthmatic individuals, the following strategy was designed to create PCR-specific primers for the authentic IL-9 receptor genes located on the X/Y pseudoautosomal regions and exclude the highly conserved IL-9 receptor pseudogenes located on chromosomes 9, 10, 16, and 18. First, sequence alignments were preformed between the two published pseudogenes and the genomic sequence of the IL-9 receptor genes. Primers were then initially designed in divergent regions between the authentic genes and the pseudogenes, and then analyzed by PCR using single chromosome-specific hybrids derived from Coreill DNA Repository (Camden, N.J.). If the primers only produce correct sized products from X and Y hybrids, they were then optimized for robust amplification. In several cases, primers directed to the divergent regions were not XY specific; therefore, applicants introduced additional base changes In the particular primer to increase the number of mismatches higher against the pseudogenes as compared to the IL-9 receptor gene sequence. Table 1 contains the sequence of the primers and optimal annealing temperatures for XY-specific amplification. The specificity of these primers for XY amplification are demonstrated in FIG. 13.

TABLE 1

X/Y Specific Amplimers of IL-9 Receptor

| EXON | SENSE PRIMER | ANTISENSE PRIMER | TEMP | SIZE |
|---|---|---|---|---|
| 2 | 5'-GCA GGT GGG GAC CCA TG -3' (SEQ ID NO: 8) | 5'- AGG CTT GAC ATC GGA CAA C-3' (SEQ ID NO: 9) | 68° | 300 bp |
| 3 | 5'- CTG GCC TGA AGT ACT TAC C-3' (SEQ ID NO: 10) | 5'- CTG CTT CAA TCC TGG GGA A -3' (SEQ ID NO: 11) | 62° | 222 bp |
| 4 | 5'- GTG AGT TCC CCA GGA TTG A-3' (SEQ ID NO: 12) | 5'- CAA GGC CCT GCT CCA AA -3' (SEQ ID NO: 13) | 64° | 335 bp |
| 5 | 5'- TGG GGC TTC AGC CTC ACA TG -3' (SEQ ID NO: 14) | 5'- TAT GTA GAG TGG GGA GTC TA -3' (SEQ ID NO: 15) | 62° | 259 bp |
| 6 | 5'- TGT ATT CTC GAG GGC TGA G -3' (SEQ ID NO: 16) | 5'- TGA GGT GAA CAG GGG AGA A -3' (SEQ ID NO: 17) | 62° | 337 bp |
| 7 | 5'- COG TGG GCC CTT CAT GT 3' (SEQ ID NO: 18) | 5'-'- ACA AGG GCG GCC TTT GAT 4 (SEQ ID NO: 19) | 60° | 262 bp |
| 8 | 5'- AGG GAC GAG GTG GGC GGA C -3' (SEQ ID NO: 20) | 5'- CCT GCC CCC CAT GTT CTT 3' (SEQ ID NO: 21) | 58° | 376 bp |
| 9 | 5'- ATG CTA CCT GAG CCC TTC C -3' (SEQ ID NO: 22) | 5'- GGA CAT GAT GCA TCT GGC G-3' (SEQ ID NO: 23) | 62° | 664 bp |

These primers represent a novel method for analyzing DNA sequence variation in these genes which can be used for diagnosis of susceptibility or resistance to atopic asthma and related disorders.

Using this technology, each exon was examined by DNA sequence analyses for individuals in applicants populations to detect sequence variation in the IL-9 receptor gene.[44] Sequence polymorphisms were distinguished from artifact by repeated analyses. An association of the receptor variants with the allergic phenotypes is set forth in FIG. 9. The sequence of the receptor alleles is set forth in FIGS. 1-8.

EXAMPLE 3

IL-9 Receptor Expression and Ligand Binding Assay

Purified recombinant IL-9 and compounds potentially resembling IL-9 in structure or function are fluorescently labeled to high specific activity by using commercially available techniques according to the supplier's recommendations (Pierce). Human Mo7e and murine 32D cells are grown and resuspended at 37° C. in 0.8 ml of Dulbecco's modified Eagle's medium supplemented with 10% (vol/vol) fetal bovine serum, 50 mM 2-mercaptoethanol, 0.55 mM L-arginine, 0.24 mM L-asparagine, and 1.25 mM L-glutamine or RPMI supplemented with 10% (vol/vol) fetal bovine serum, 50 mM 2-mercaptoethanol, 0.55 mM L-arginine, 0.24 mM L-asparagine, and 1.25 mM L-glutamine, respectively. TF1.1 (TF 1 cells lacking human IL-9 receptors), T98G, TK, and murine 32D cells, (Examples 7 and 10) were used as is or after transfection with the human IL-9 receptor constructs as described below. Plasmid DNA containing one of the full-length or truncated forms of IL-9 receptors were cloned into pCEP4 plasmid (Clontech) and purified by centrifugation through Qiagen columns (Qiagen). Plasmid DNA (50 µgrams) was added to the cells in 0.4 cm cuvettes just before electroporation. After a double electric pulse (750V/74 ohms/40 microfarads and 100V/74 ohms/2100 microfarads), the cells are immediately diluted in fresh medium supplemented with IL-9.

Stable transfected cells were generated after 14 days of selection with hygromycin B (400 µg/ml to 1.6 mg/ml). Hygromycin-resistant clones were analyzed for IL-9 receptor expression by Western blots and in situ staining as described in Example 8.

Cellular receptor binding is visualized directly in real time with fluorescence microscopy. Binding and internalization is followed over time in control cells (not transfected), and with cells transfected with each of the known IL-9 receptor variants. An excess of unlabeled ligand or blocking antibody is used in parallel experiments to demonstrate specific binding.

Soluble IL-9 receptor including amino acids 44 to 270 with or without a HA ditag is also incubated with different forms of human labeled recombinant IL-9. Varying amounts of FLAG-tagged (1131) ligand are incubated in PBS at, room temperature for 30 minutes with 0.5 µg of soluble receptor. EBC buffer (50 mM Tris pH 7.5; 0.1 M NaCl; 0.5% NP40) is added (300 µl) along with 1 µg of anti-HA antibody or anti-FLAG monoclonal antibody (IBI) and incubated for 1 hour on ice. Forty microliters of protein A sepharose solution were added to each sample and mixed for 1 hour at 4° C. Samples were centrifuged for 1 minute 11,000×G and pellets were washed 4 times with 500 µl of EBC. Pellets were dissolved in 26 pi of 2×SDS buffer, boiled for 4 minutes, and electrophoresed through an 18% SOS polyacrylamide gel. Western blots were probed with an anti-IL-9 receptor antibody (Santa Cruz Inc.) or anti-FLAG monoclonal antibody (IBI) against FLAG-tagged rh1L-9. Therapeutic candidates are assessed by measuring the antagonism of ligand binding. Receptor expression is shown in FIGS. 11 and 14.

EXAMPLE 4

Cell Isolation and Culture

Human peripheral blood mononuclear cells (PBMC) were isolated from healthy donors by density gradient centrifugation using endotoxin tested Ficoll-Paque PLUS according to the manufacturer (Phermacia Biotech, AB Uppsala Sweden). PBMC ($5\times10^6$), mouse spleen cells ($5\times10^6$), or $5\times108$ Mole cells were cultured in 7 ml of RPMI-1640 (Bethesda Research Labs (BRL), Bethesda, Md.) supplemented to a final concentration of 10% with either isogenic human serum or heat-inactivated FBS. Cells were cultured for 24 hm at 37° C. either unstimulated, or stimulated with either PMA 5 Ng/mV PHA 5 µg/ml, or PHA 5 µg/ml and rhIL2 50 ng/ml (R&D Systems, Minneapolis, Minn.).

EXAMPLE 5

DNA & RNA Isolations, rtPCR, Cloning, and Sequencing of PCR Products

Cytoplasmic RNA and genomic DNA were extracted after 6 days of mitogen stimulation from cultured PBMCs, as described by Nicolaides and Stoeckert.[46] One µg of RNA from each source was denatured for >10 minutes at 70° C. and then reverse transcribed(V+) into cDNA using 2.5 units of Superscript II reverse transcriptase. (GIBCO, BRL), 1U/I RNAse Inhibitor, 2.5 mM oligo d(T)16 primer, 1 mM each of dATP, dCTP, dGTP, dTTP, 50 mM KCl, 10 mM Tris-HCL, pH 7.0, 25 mM $MgCl_2$ at 37° C. for one hour. A mock reverse transcription reaction was used as a negative control.

One-twentieth of the rt reaction was used in PCR (50 µl) containing 6.7 mM $MgCl_2$, 16.6 mM $(NH_4)_2SO_4$, 67 mM Tris-HCL, pH 8.8, 10 mM 2-mercaptoethanol, 6% DMSO, 1.25 mM of each dNTP, 2.5U Amplitaq DNA polymerase, and 300 ng of each of the oligonucleotides representing human cDNA IL-9 exon 2 (forward 5'-GCT GGA CCT TGG AGA GTG-3') (SEQ ID NO: 25) and exon 9 (reverse 5'-GTC TCA GAC AAG GGC TCC AG-3') (SEQ ID NO: 26). The reaction mixture was subjected to the following PCR conditions: 120 seconds at 95° C., then 35 cycles at: 30 seconds at 94° C.; 90 seconds at 58° C.; 90 seconds at 72° C. Finally, the reaction mixture was cycled one time for 15 minutes at 72° C. for extension.

PCR products representing hIL-9 receptor cDNA were subjected to gel electrophoresis through 1.5% agarose gels and visualized using ethidium bromide staining. Products of a mock reverse transcriptate reaction, in which $H_2O$ was substituted for RNA, ware used as a negative control amplification in all experiments.

PCR products were subcloned into the TA Cloning vector (Invitrogen, San Diego, Calif.). Amplification of the human cDNA gave a 1614 by product. Plasmids containing hIL-9 receptor cDNA inserts were isolated by conventional techniques (Sambrook, J., et al. (1989) Molecular Cloning: A Laboratory Manual Cold Spring Harbor Laboratory Press, New York). After amplification the DNA sequence including and surrounding each insert was analyzed by sequencing (Sanger et al., 1977, Proc. Nati. Acad. Sci. USA 74:5463) using fluorescent dideoxyterminators and on an automated sequencer (ABI 377, Perkin Elmer) for determination of PCR-induced or cloning-induced errors. hIL9 receptor cDNA inserts without cloning and/or polymerase-induced sequence errors were subcloned into expression vectors.

EXAMPLE 6

Figure 10:
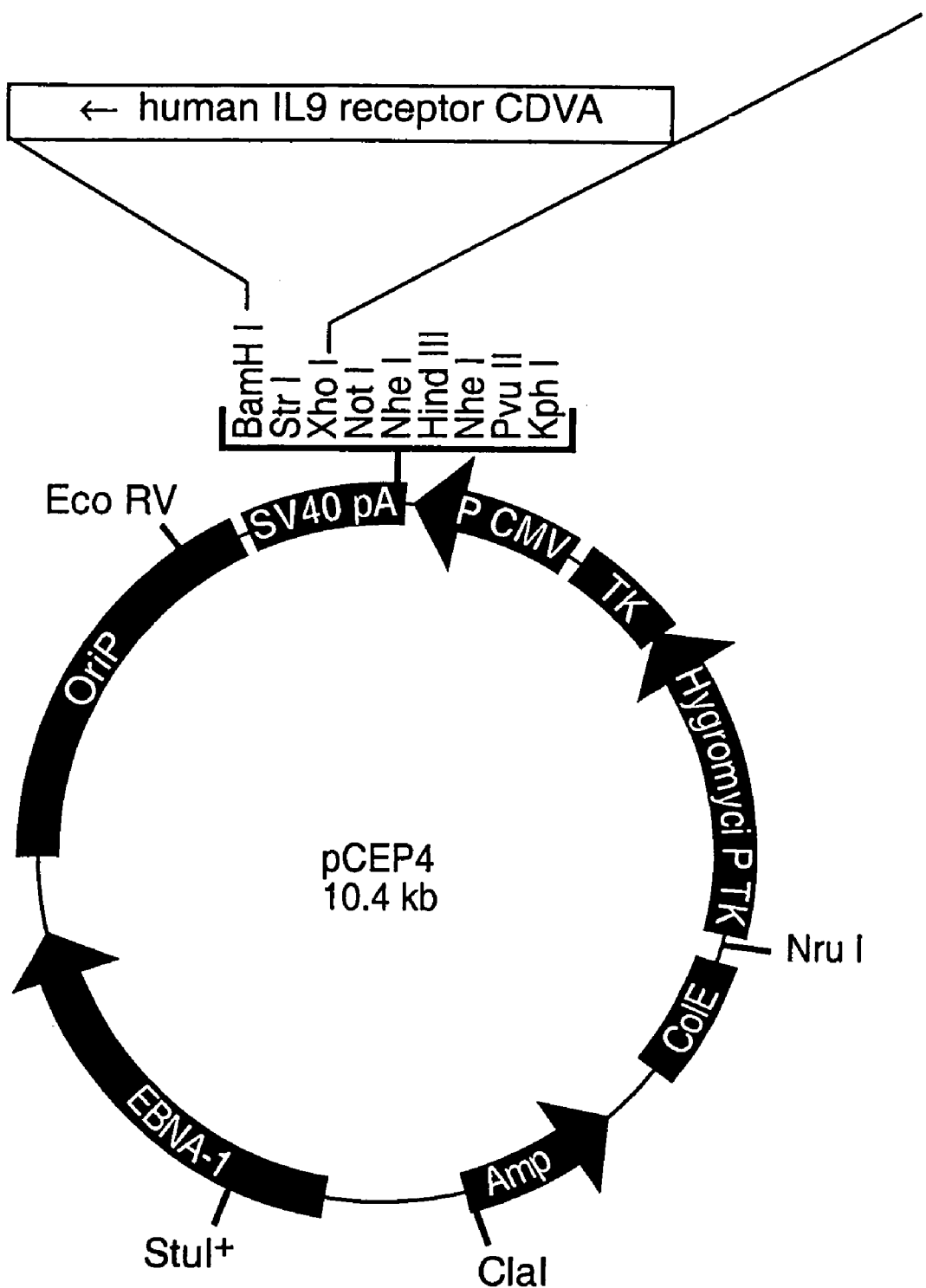
FIG. 10: Map of the expression construct of the IL-9 receptor.

Cloning and Expression of IL-9 Receptor Constructs In Vitro hIL-9 receptors were subcloned into the episomal eukaryotic expression vector pCEP4 nlontech). Inserts were cloned as BamH1-Xhol fragments into the pCEP4 polylinker in the sense orientation to the CMV promoter using standard techniques (FIG. 10). Constructs were expressed in cellular hosts as described.

EXAMPLE 7

Cellular Assays Using (Mo7e, 32D, TF1.1 TK ts13, and T98G

Cell lines were used to assess the function of variant IL-9 receptors and for the screening of compounds potentially useful in the treatment of atopic asthma. Compounds were tested for their ability to antagonize the anti-apoptotic or baseline proliferative response elicited by IL-9. Once a baseline anti-apoptotic or proliferative response was established in a given cell line, a statistically significant loss of response in assays repeated three times in triplicate was considered evidence for antagonism. A true antagonistic response was differentiated from cellular toxicity by direct observation, trypan blue staining (a technique well known to one of normal skill in the art), or loss of acid phosphatase activity. Specificity of antagonism is assessed for each compound by evaluating whether the activity is demonstrated against other proliferative agents such as interleukin 3 or interleukin 4.

Recombinant IL-9 and compounds potentially resembling IL-9 in structure or function were purified and prepared for use in the appropriate media. Putative agonists and antagonists were prepared in water, saline, or DMSO and water. Cells were used as is or after transfection with the IL-9 receptor constructs as described in Example 3. After 24 hrs of deprivation from growth factors, the cells were incubated without (control) or with variable amounts of purified IL-9 and compounds potentially resembling IL-9 in structure or function.

Cell proliferation was assayed using the Abacus Cell Proliferation Kit (Clontech, Palo Alto, Calif.) which determines the amount of intracellular acid phosphatase present as an indication of cell number. The substrate p-nitrophenol phosphate (pNPP) was converted by acid phosphatase to p-nitrophenol, which was measured as an indicator of enzyme concentration. pNPP was added to each well and incubated at 37° C. for one hour. 1 N sodium hydroxide was then added to stop the enzymatic reaction, and the amount of p-nitrophenol was quantified using a Dynatech 2000 plate reader (Dynatech Laboratories, Chantilly, Va.) at 410 nm wavelength. Standard curves that compare cell number with optical absorbance were used to determine the linear range of the assay. Assay results were only used when absorbance measurements are within the linear range of the assay. Briefly, the assays were run with quadruplicate samples of cells in flat-bottom µtiter plates (150 or 200 microliter wells) With or without ligand for 72 to 96 hours at 37 degrees C. Acid phosphatase was used as a measure of the number of cells present. All experiments are repeated at least-twice.

Apoptosis was assayed using the Annexin V kit as described by the supplier (Clontech) which determines dexamethesone-induced apoptosis by recognizing extracellular phosphatidyiserine, an early marker for apoptosis. Apoptotic cell number was scored by fluorescence microscopy as a percentage of Annexin V stained cells.

The Mo7e line is a human megakaryoblastic cell line, cultured in RPMI 1640 (GIBCO/BRL, Gaithersburg, Md.), 20% Fetal Bovine Serum (Hyclone) and 10 ng/ml IL-3 (R&D Systems, Minneapolis, Minn.). The T98G line is a human glioblastoma cell line grown in RPMI 1640 (GIBCO/BRL). The hamster fibroblast TK-ts13 line was also used as well as the murine 32D cell line, a murine myeloid precursor line, and both were cultured in RPMI 1640 (GIBCO/BRL) containing 10% fetal bovine serum (Hyclone) in addition 1 ng/ml m IL-3 was used with the 32 D cell lines. TF1.1 is a human myeloid leukemia line known to express the IL-2 receptor gamma subunit (confirmed by Western blots and rtPCR), but, in comparison to its predecessor (TF1), it no longer bears IL-9 receptor by rtPCR, immunostaining, and Western blot analyses. TF1.1 is cultured in RPMI 1640 (GIBCO/BRL) and 10% Fetal bovine serum (Hyclone). All the cell lines respond to multiple cytokines including IL-9. The cell lines were fed and reseeded at $2\times10^5$ cells/ml every 72 hours.

The cells were centrifuged for 10 minutes at 2000 rpm and resuspended in RPMI 1640 with 0.5% Bovine Serum Albumin (GIBCO/BRL, Gaithersburg, Md.) and were counted using a hemocytometer and diluted to a concentration of $1\times10^5$ cells/ml and plated in a 96-well microtiter plate. Each well contained 0.15 or 0.2 ml, giving a final concentration of 10 to 50 thousand cells per well depending on the cell. Mole cells were stimulated with 50 ng/ml Stem Cell Factor (SCF) (R&D Systems, Minneapolis, Minn.) alone, 50 ng/ml SCF plus 50 ng/ml IL-3 (R&D Systems, Minneapolis, Minn.), or 50 ng/ml SCF plus 50 ng/ml IL-9. A control was included which contained cells and basal media only, Serial dilutions of test compounds (i.e., recombinant IL-9 proteins, peptides, small molecules) were added to each test condition in triplicate. TF1.1 cells that were not transfected with IL-9 receptors were used as an independent control for response and nonspecific cytotoxicity. Cultures were incubated for 72-96 hours at 37° C. in 5% $CO_2$.

EXAMPLE 8

In Situ & Western Analysis of Exogenous IL-9 Receptor in Transfected Cell Lines

In situ staining of the IL-9 receptor was carried out as follows. Cells were grown on coverslips for 24 hours and then coverslips containing the adherent cells were washed twice in phosphate buffered saline solution containing calcium and magnesium(PBS) (Gibco/BRL). For Intracellular staining of the IL-9 receptor, the cells were fixed in 4% paraformaldehyde/PBS plus 0.1% triton-X for 15 minutes at room temperature before treatment with anti-human IL-9 receptor antibody; for extracellular staining, cells were treated with antibody before fixation. The cells were then washed twice in PBS and blocked with 7.5°/a BSA in $dH_2O$ for 30 minutes at room temperature. PBS washed cells were then incubated with a 10 µg/ml solution of anti-human IL-9 receptor (polyclonal antibody directed against the carboxy terminus of the IL-9 receptor) in 1% BSA/PBS for 1 hour at room temperature. Cells were washed three times in PBS and then incubated in 10 µg/ml solution of an anti-rabbit rhodamine-conjugated antibody in 1% BSA/PBS for 30 minutes at room temperature. Cells were then washed three times in PBS and counter-stained using 1 µg/ml DAPI for 1 minute at room temperature. Cells were washed three times in $dH_2O$ and fixed to a microscope slide and analyzed by fluorescence microscopy. The results for the transferred COST cells are shown in FIG. 14.

Western blots were performed on protein lysates obtained from direct lysis of cell extracts in 0.5% lysis buffer (Tris 50 mM, NaCl 150 mM, NP40), 1 mM DTT and protease inhibitors) and boiled for 5 minutes, Samples were electrophoresed on 4-20% tris-glycine SDS gels (Novex) in trisglycine running buffer. Proteins were then transferred to nitrocellulose by electroblot using the Trans Blot II apparatus (Bio Red). After transfer, the membrane was blocked in TBS-T ((20 mM Tris, 137 mM NaCl, pH 7.6) plus 0.05% Tween 20) plus 5% blotto for 1 hour room temperature. Blots were then probed using a polyclonal antibody directed to the carboxy terminus of the IL-9 receptor (1 µg/ml) in TBS-T for 1 hour. Blots were then washed three times in TBS-T for 10 minutes and probed using a secondary anti-rabbit-horse radish peroxidase conjugated antibody (1:10,000) in TBS-T for 30 minutes. Blots were washed as above and then incubated with Luminol/enhancer solution (Pierce), a chemiluminescent substrate, for 5 minutes at room temperature and then exposed to film for 1-60 seconds. See FIGS. 11 and 12.

EXAMPLE 9

Methods for the Authentic IL-9R Genomic Am$^p$lification

Specific amplification of the authentic IL-9R (gene encoding for the biologically functional protein located in the XYq pseudoautosomal region) using standard primer design was not possible because IL-9R has four highly homologous (>90% nucleotide identity), nonprooessed pseudogenes at other loci in the human genome (chromosome 9, 10, 16, 18). Because of the high identity of these other genes, genomic PCR amplification using standard primer design resulted in co-amplification of all genes, thus making sequence analysis of the authentic gene equivocal. In order to study authentic IL-9R structure as it may relate to predisposition to disease such as asthma, discussed in this application, or other diseases such as cancer (Renauld, et al., *Oncogene*, 9:1327-1332,1 994; Gruss, et al., *Cancer Res.*, 52:1026-1031,1992), specific amplimers were designed as follows:

Sequences of the IL-9R pseudogene and authentic genes were aligned using Mac Vector software. Intronic sequences surrounding each exon were then inspected for regions of diversity between the authentic gene and pseudogenes. Primers were then designed against these regions, and used to PCR amplify human/rodent hybrid DNAs containing individual human chromosomes. Products were run on 3% agarose gels and analyzed for authentic IL-9R amplification with no amplification of the 4 pseudogenes. Specific PCR amplification conditions were also optimized by varying annealing temperature and buffer conditions (DMSO content 5-10%). In cases where amplification of pseudogenes still occurred, nucleotide changes were entered into primer sequences to cause greater divergence from the pseudogenes as compared to the authentic gene, Primer sequences are shown In Example 2 and their specificity is demonstrated in FIG. 13.

EXAMPLE 10

Cell Proliferation Assay and Cytokine Stimulation

To determine growth response of TS1 cells expressing various forms of human IL-9 receptor, cells were washed with PBS and resuspended in D-MEM, 10% fetal bovine serum. $10^3$ cells per well were seeded in triplicate in 96-well microplates and, where appropriate, recombinant human IL-9 or marine IL-9 (R&D Systems, Minneapolis, Minn.) was added at a final concentration of 5 ng/ml. Cell proliferation was evaluated after 7 days using an acid phosphatase assay. Briefly, 50 µl of a buffer containing 0.1 M sodium acetate (pH 5.5), 0.1% Triton X-100 and 10 mM p-nitrophenyl phosphate (Sigma 104 phosphatase substrate) was added per well, The plate was incubated for 1-½ hours at room temperature, the reaction stopped with 10 µl/well of 1 N sodium hydroxide and the absorbance was read on a Dynatech Model MR600 at 410 nm, To analyze tyrosine-phosphorylation of proteins of the signal transduction cascade upon cytokine stimulation, TS1 cells expressing various forms of human IL-9 receptor were washed with PBS, resuspended in D-MEM, 0.5% bovine serum albumin, and incubated for 6 hours at 37° C. Successively, $20 \times 10^8$ cells were treated for 5 minutes with either human IL-9 or murine IL-9 (100 ng/ml) and immediately washed in cold PBS. Cells were lysed in RIPA buffer as described in Example 11.

EXAMPLE 11

Immunoprecipitations, Immunoblotting and Antibodies

Typically, $20\text{-}50 \times 10^6$ cells were lysed in 1 ml of RIPA buffer (PBS containing 1% NP40, 0.5% sodium deoxycholate, 0.1% SIDS, 1 mM PMSF, 50 mM sodium fluoride, 1 nM sodium orthovanadate, and 1× "Complete" protease inhibitors mixture, Cat. No. 1697498 Boehringer Mannheim) and Incubated for 45 minutes on ice. Lysates were centrifuged for 20 minutes In an Eppendorf microcentrifuge and the supernatant recovered and transferred to a fresh tube. For Immunopreeipkations, 1-5 µg of the antibody were added to the lysate and incubated overnight at 4° C. 20 ml of Protein A+G agarose-conjugated beads were added for 2 hrs followed by four washings using RIPA buffer: Beads were resuspended in Laemmli buffer and boiled for 3 minutes before electrophoresis. Proteins were transferred onto Immobiiion-P membrane (Millipore) and detected using a horseradish peroxidase-conjugated secondary antibody followed by a chemiluminescence detection assay (Pierce). Specific antibodies for murine and human IL-9 receptor (sc698), murine Jak1, irs1, Irs2, Stat1, Stat2, Stat3, Stat4, Stat5, and phosphotyrosine (PY) were purchased from Santa Cruz (Santa Cruz, Calif.). Anti-Jak3 and monoclonal anti-human IL-9 receptor MAS290 were purchased from Upstate Biotechnology and R&D Systems, respectively. FIG. 15 demonstrates the activation of members of the Jak family via different variants of the human IL-9 receptor.

EXAMPLE 12

Identification of IL-9 Receptor Genomic Polymorphisms

Genomic DNAs were isolated from PBMCs of volunteer donors as described (Nicolaides and Stoecker, Biotechniques 8:154-156, 1990). Sequence analysis of intron 5 of the human IL-9R gene was performed by PCR using primers of sequence ID NO 14 and sequence ID NO 17 which resulted in a product with the approximated molecular size of 1243 basepairs, Amplifications were carried out at 94° C. for 30 seconds, 62° C. for 1.5 minutes, 72° C. for 1.5 minutes for 35 cycles in buffers described previously (Nicholaides et al., Genomics 30:195-206,1995). Products were then purified and sequenced using a standard sequence protocol. Inspection of the sequences from intron 5 in multiple individuals found a nucleotide change at −213 nt upstream of axon 6 sequences which resulted in a thymidine (published sequence) to a cytosine nucleotide change. An example of this change is shown in FIG. 17.

While the invention has been described and illustrated herein by references to various specific materials, procedures and examples, it is understood that the invention is not restricted to the particular material combinations of material, and procedures selected for that purpose. Numerous variations of such details can be implied as will be appreciated by those skilled in the art.

REFERENCES

1. Gergen P J, and Weiss K B: The increasing problem of asthma in the United States. *Am Rev Respir Dis* 146:823-824, 1992.
2. Goodman and Gilman's *The Phannacologic Basis of Therapeutics*, Seventh Edition, MacMillan Publishing Company, N.Y. USA, 1985.
3. Burrows B, Martinez F D, Halonen M, Barbee R A, and Cline M G: Association of asthma with serum IgE levels and skin-test reactivity to allergens, *New Eng J Med* 320:271-277, 1989.
4. Clifford R D, Pugsley A, Radford M, and Holgate S T: Symptoms, atopy, and bronchial response to methacholine in parents with asthma and their children. *Arch Dis in Childhood* 62:66-73, 1987.
5. Gergen P J: The association of allergen skin test reactivity and respiratory disease among whites in the U.S. population. *Arch Intern Med* 151:487-492, 1991.

6. Burrows B, Sears M R, Flannery E M, Herbison G P, and Holdaway M D: Relationship of bronchial responsiveness assessed by methacholine to serum IgE, lung function, symptoms, and diagnoses in 11-year-old New Zealand children. *J Allergy Clin Immunol* 90:376-385,1992.
7. Johannson SGO, Bennich H H, and Berg T: The clinical significance of *Prog Clin Immunol* 1:1-25, 1972.
8. Sears M R, Burrows B, Flannery E M, Herbison G P, Hewitt C J, and Holdaway M D: Relation between airway responsiveness and serum IgE in children with asthma and in apparently normal children *New Engl. J. Med* 325 (15): 1067-71, 1991.
9. Halonen M, Stem D, Taussig L M, Wright A, Ray C G, and Martinez F D: The predictive relationship between serum IgE levels at birth and subsequent incidences of lower respiratory illnesses and eczema in infants. *Am Rev Respir Dis* 146:666-670, 1992.
10. Marsh D G, Meyers D A, and Bias W B: The epidemiology and genetics of atopic allergy. *New Eng J Med* 305:1551-1559,1982.
11. Hopp R J, Bewtra A K, Biven R, Nair N M, Townley R G. Bronchial reactivity pattern in nonasthmatic parents of asthmatics. *Ann Allergy* 1988;61: 164-186.
12. Hopp R J, Townley R G, Biven R E, Bewtra A K, Nair N M. The presence of airway reactivity before the development of asthma. *Am Rev Respir Dis* 1990;141:2-8.
13. Ackerman V, Marini M, Vittori E, et al. Detection of cytokines and their cell sources in bronchial biopsy specimens from asthmatic patients: relationship to atopic status, symptoms, and level of airway hyperresponsiveness. *Chest* 1994; 105:687-696.
14. Hamid G, Azzawl M, Ying S, et al. Expression of mRNA for interleukin-5 in mucosal bronchial biopsies from asthma. *J Clin Invest* 1991;87:1541-1546.
15. Djukanovic R, Roche W R, Wilson J W, et al. Mucosal inflammation in asthma. *Am Rev Respir Dis* 1990;142: 434-57.
16. Robinson D S, Hamid Q, Ying S, et al. Predominant TH2-like bronchoalveolar T lymphocyte population in atopic asthma. *N Engl J Med* 1992;326:298-304.
17. Robinson D S, Hamid Q. Ying S, et al. Prednisolone treatment in asthma is associated with modulation of bronchoalveolar lavage cell interleukin-4, interleukin-5, and interferon-_cytokine gene expression. *Am Rev Respir Dis* 1993; 148: 401-406.
18. Robinson D S, Ying S, Bentley A, et al. Relationship among numbers of bronchoalveolar lavage cells expressing messenger ribonucleic acid for cytokines, asthma symptoms, and airway methacholine responsiveness in atopic asthma. *Allergy Clin Immunol* 1993;92:397403.
19. O'Connor G T, Sparrow D, and Weiss S T: The role of allergy and nonspecific BHR in the pathogenesis of COPD. *Am Rev Respir Dis* 140:225-252, 1989.
20. Cogswell J J, Halliday D F, and Alexander J R: Respiratory Infections In the first year of life in children at the risk of developing atopy. *Brit Med J* 284:1011-1013, 1982.
21. Boushey H A, Holtzman M J, Sheller J R, And Nadel J A: BHR. *Am Rev Res it Dis* 121:389413,1980.
22. Renauld, J-C, Houssiau, F, Druez, C. Interleukin-9. *Int Rev Exp Pathology* 1993;34A: 99-109.
23. Renauld, J-C, Kermouni, A, Vink, A, Louahed, J, Van Snick, J. Interleukin-9 and its receptor: involvement In mast cell differentiation and T cell oncogenesis. *J Leukoc Biol* 1995;57:353-360.
24. Hultner, L, Moeller, J, Schmitt, E, Jager, G, Reisbach, G, Ring, J. Dormer, P. Thiol-sensitive mast cell lines derived from mouse bone marrow respond to a mast cell growth-enhancing activity d'fferent from both IL-3 and IL-4. *J Immunol* 1989; 142:3440-3448.
25. Dugas, B, Renauld, J-C, Pene, J, Bonnefoy, J, Peti-Frere, C. Braquet, P, Bousquet, J, Van Snick, J, Mencia-Huerta, J M. Interleukin-9 potentiates the interleukin-4-induced immunoglobulin (IgG, IgM and IgE) production by normal human B lymphocytes. *Eur J Immunol* 1993:23: 1687-1692.
26. Petit-Frere, C, Dugas, B, Braquet, P, Mencia-Huerta, J M. Interleukin-9 potentiates the interleukin-4-induced IgE and IgG1 release from murine B lymphocytes. *Immunology* 1993;79:146-151.
27. Behnke, J M, Wahid, F N, Grencis, R K, Else, K J, Ben-Smith, A W, Goyal, P K. Immunological relationships during primary infection with Heligmosomoides polygyrus (Nematospiroides dubius): downregulation of specific cytokine secretion (IL-9 and IL-10) correlates with poor mastocytosis and chronic survival of adult worms. *Parasite Immunol* 1993;15:415-421.
28. Gessner, A, Blum, H, Rollinghoff, M. Differential regulation of IL-9 expression after infection with Leischmania major in susceptible and resistant mice. *Immunobiology* 1993;189:419-435.
29. Renauld J-C, Druez C, Kermouni A, et al. Expression cloning of the murine and human interleukin 9 receptor cDNAs. *Proc Natl Aced Sci* 89:5690-5694(1992).
30. Chang M-S, Engel G, Benedict C et al, Isolation and characterization of the Human interleukin-9 receptor gene. *Blood* 83:3199-3205(1994).
31. Renauld J-C, Goethals A, Houssiau F, et al. Human P401IL-9. Expression in activated C04+T cells, Genomic Organization, and Comparison with the Mouse Gene. *J Immunol* 144:4235-4241(1990).
32. Kelleher K, Bean K, Clark S C, et al. Human interleukin-9: genomic sequence, chromosomal location, and sequences essential for its expression in human T-cell leukemia virus (HTLV-1-transformed human T cells. *Blood* 77:1436-1441(1991).
33. Houssiau F A, Schandene L, Stevens M, et al. A cascade of cytokines is responsible for IL-9 expression in human T cells. Involvement of IL-2, IL-4, and IL-10. *J of Immunol.* 154:2624-2630(1995).
34. Miyazawa K, Hendrie P C, Kim Y-J, et al. Recombinant human interleukin-9 induces protein tyrosine phosphorylation and synergizes with steel factor to stimulate proliferation of the human factor-dependent cell line, Mo7e, *Blood* 80: 1685-1692(19992).
35. Yin T, Tsang M L-S, Yang Y-C. JAM kinase forms complexes with interleukin4 receptor and 4PS/insulin receptor substrate-1 -like protein and is activated by interleukin4 and Interleukin-9 in T lymphocytes. *J Biol Chem* 269:26614-26617(1994).
36. Zav'yalov V P, Navolotskaya E V, Isaev I S, et al. Nonapeptide corresponding to the sequence 27-35 of the mature human IL-2 efficiently competes with rIL-2 for binding to thymocyte receptors. *Immunol Lett* 31:285-288 (1992).
37. Chu J W, and Sharom F J. Glycophorin A interacts with intedeukin-2 and inhibits interleukin-2-dependent T-lymphocyte proliferation. *Cell Immunol* 145:223-239(1992).
38. Alexander A G, Barnes N C, Kay A B. Trial of cyclosporin in corticosteroid-dependent chronic severe asthma Lapp 339:324-328(1992).
39. Morely J. Cyclosporin A in asthma therapy: a pharmacological rationale. *I Autoimmun* 5 Suppl A:265-269 (1992).

40. Sheffield V C, Beck J S, Kwitek A E, Sandstrom D W, and Stone E M: The sensitivity of single-strand conformation polymorphism analysis for the detection of single base substitutions. *Genomics* 16:325-332, 1993.
41. Orita M, Suzuki Y, Sekiya T, and Hayashi K: Rapid and sensitive detection of point mutations and DNA polymorphisms using the polymerase chain reaction. *Genomics* 5:874-9,1989.
42. Sarkar G, Yoon H-S, and Sommer S S: Dideoxy fingerprint (ddF): A rapid and efficient screen for the presence of mutations. *Genomics* 13:441-443, 1992.
43. Cotton R G: Detection of single base changes in nucleic acids. *Biochemical Journal* 263(1): 1-10; 1989.
44. Schwengel D, Nouri N, Meyers D, and Levitt R C: Linkage mapping of the human thromboxane A2 receptor (TBXA2R) to chromosome 19p13.3 using transcribed 3' untransiated DNA sequence polymorphisms. *Genomics* 18:212-215, 1993.
45. *Cytokine Handbook*, Angus Thomson (1994).
46. Nicolaides, N. C. and Stoecker, C. J. A simple, efficient method for the separate isolation of RNA and DNA from the same cells, *Biotechniques* 1996;8:154-156.
47. Ott J. *Analysis of Human Genetic Linkage*. Baltimore, Md.: The Johns Hopkins University Press, 1991.
48. Meyers D A, Postma D S, Panhuysen C I M, et al. Evidence for a locus regulating total serum IgE levels mapping to chromosome 5. *Genomics* 1994;23:484 470.41.

What is claimed is:

1. An isolated nucleic acid molecule comprising the nucleotide sequence encoding human interleukin-9 receptor wherein nucleic acids 613-617 of the wild-type human interleukin-9 receptor nucleotide sequence (SEQ ID NO: 1) have been deleted.

2. The isolated nucleic acid molecule of claim 1 wherein the nucleotide sequence comprises SEQ ID NO: 7.

3. The isolated nucleic acid molecule of claim 1 wherein the nucleotide sequence consists of SEQ ID NO: 7.

4. The isolated nucleic acid molecule of claim 1 wherein the nucleic acid molecule is operably linked to one or more expression control elements.

5. An isolated vector comprising the isolated nucleic acid molecule of claim 1.

6. A host cell line comprising the vector of claim 5.

7. The host cell line of claim 6 wherein the host cell is stably transformed with the vector.

8. The host cell line of claim 6, wherein said host is selected from the group consisting of prokaryotic host cells and eukaryotic host cells.

9. A method for producing a polypeptide comprising culturing the host cell line of claim 6 under conditions in which the polypeptide encoded by the nucleic acid molecule is expressed and isolating the polypeptide.

10. An isolated nucleic acid molecule comprising a nucleotide sequence encoding the amino acid sequence of SEQ ID NO: 33.

11. The isolated nucleic acid molecule of claim 10 wherein the nucleotide sequence comprises SEQ ID NO: 7.

12. The isolated nucleic acid molecule of claim 10 wherein the nucleotide sequence consists of SEQ ID NO: 7.

13. The isolated nucleic acid molecule of claim 10 wherein the nucleic acid molecule is operably linked to one or more expression control elements.

14. An isolated vector comprising the isolated nucleic acid molecule of claim 10.

15. A host cell line comprising the vector of claim 6.

16. The host cell line of claim 15 wherein the host cell is stably transformed with the vector.

17. The host cell line of claim 15 wherein said host is selected from the group consisting of prokaryotic host cells and eukaryotic host cells.

18. A method for producing a polypeptide comprising culturing the host cell line of claim 15 under conditions in which the polypeptide encoded by the nucleic acid molecule is expressed and isolating the polypeptide.

* * * * *